US008435954B2

(12) United States Patent
Ong et al.

(10) Patent No.: US 8,435,954 B2
(45) Date of Patent: May 7, 2013

(54) AZAPEPTIDES AS CD36 BINDING COMPOUNDS

(75) Inventors: Huy Ong, Ville Mont-Royal (CA); Sylvain Chemtob, Côte St-Luc (CA); William Lubell, Montreal (CA); Florian Sennlaub, Paris (FR); Damien Boeglin, Ostwald (FR); Caroline Proulx, Montreal (CA); Zohreh Sajjadi, Guilderland, NY (US); David Sabatino, Montreal (CA)

(73) Assignees: Valorisation-Recherche, Limited Partnership, Montreal (CA); Valorisation HSJ, Limited Partnership, Montreal (CA)

( * ) Notice: Subject to any disclaimer, the term of this patent is extended or adjusted under 35 U.S.C. 154(b) by 485 days.

(21) Appl. No.: 12/452,114

(22) PCT Filed: Jun. 18, 2008

(86) PCT No.: PCT/CA2008/001162
§ 371 (c)(1),
(2), (4) Date: Apr. 26, 2010

(87) PCT Pub. No.: WO2008/154738
PCT Pub. Date: Dec. 24, 2008

(65) Prior Publication Data
US 2010/0210566 A1 Aug. 19, 2010

Related U.S. Application Data

(60) Provisional application No. 60/944,712, filed on Jun. 18, 2007.

(51) Int. Cl.
*A61K 38/08* (2006.01)
*C07K 7/02* (2006.01)

(52) U.S. Cl.
USPC ........................................ 514/21.8; 530/323

(58) Field of Classification Search ................ 514/21.8; 530/323
See application file for complete search history.

(56) References Cited

FOREIGN PATENT DOCUMENTS

| CA | 2 399 548 | 2/2004 |
|---|---|---|
| CA | 2399548 | 2/2004 |
| WO | 2004/017986 | 3/2004 |
| WO | WO 2004/017986 | 3/2004 |

OTHER PUBLICATIONS

International Search Report PCT/CA2008/001162 mailed Sep. 10, 2008.
Written Opinion of the International Searching Authority for PCT/CA2008/001162 mailed Sep. 10, 2008.
Boeglin et al, "Aza-amino acid scanning of secondary structure suited for solid-phase peptide synthesis with Fmoc chemistry and aza-amino acids with heteroatomic side chains", (2005), J. Comb. Chem., vol. 7, pp. 864-878.
Demers et al., "Identification of the growth hormone-releasing peptide binding site in CD36: a photoaffinity cross-linking study", (2004), Biochem. J., vol. 382, pp. 417-424.
Febbraio et al., "CD36: a class B scavenger receptor involved in angiogenesis, atherosclerosis, inflammation and lipid metabolism", (2001), J. Clin. Invest., Vo. 108(6), pp. 785-791.
Andersen et al., "Alternative promoter usage of the membrane glycoprotein CD36", (Mar. 3, 2006), BMC Molecular Biology 2006, vol. 7, p. 8.
Mwailambo et al., "Activation of CD36 inhibits and induces regression of inflammatory corneal neovascularization", (Oct. 2006), vol. 47(10), pp. 4356-4364.
Morley et al., Journal of General Microbiology, (1983), vol. 129(12), pp. 3701-3702.
Adams, J.H.; et al. A Reinvestigation of the Preparation, Properties, and Applications of Aminomethyl and 4-Methylbenzhydrylamine Polystyrene Resins. *J. Org. Chem.* 1998, 63, 3706-3716.
Ambati J, Ambati BK, Yoo SH et al. Age-related macular degeneration:etiology, pathogenesis, and therapeutic strategies.*Surv Opthalmo*. 2003;48:2572-93.
Amburad N, Harmon C, Ibrahimi A. Membrane transport of long chain fatty acids: evidence for a facilitated process. *J.lipid Res1998*; 39: 2309-2318.
Andersen et al., Alternative promoter usage of the membrane of glycoprotein CD36, *Molecular Biology*, 2006, 7:8.
Arrowsmith, J. E.; Cook, M. J.; Hardstone, D. J. Reactions of anions of N-benzylidenebenzylamines and related compounds. A simple route to α-substituted benzylamines. *J. Chem. Soc., Perkin Trans, 1* 1979, 2364-2368.
Asai, T.; Aoyama, T.; Shioiri, T. New methods and reagents in organic synthesis. 7. α-Alkylation of benzylamine under phase-transfer catalyzed conditions. *Synthesis* 1980, 811-812.
Augustin AJ, Schmidt —Erfurth U. Verteporfin therapy combined with intravitreal triamcinolone in all types of choroidal neovascularisation due to age-related macular degeneration. *Ophthalmology 2006*; 113:14-22.
Avallone R, Demers A, Rodrigue-Way A et al. A growth hormone-releasing peptide that binds scavenger receptor CD36 and ghrelin receptor upregulates ABC sterol transporters and cholesterol efflux in macrophages through PPARγ-dependent pathway. *Mol. Endocrinol 2006*, 20(12):3165-3178.
Bodart V, Febbraio M, Demers A. et al. CD36 mediates the cardio-vascular action of growth hormone-releasing peptides in the heart. *Circ. Res 2002*; 90:844-849.
Boeglin, D.; Lubell, W. D. Aza-Amino Acid Scanning of Secondary Structure Suited for Solid-Phase Peptide Synthesis with Fmoc Chemistry and Aza-Amino Acids with Heteroatomic Side chain. *J. Comb. Chem 2005*; 7(6); 864-868.
Boeglin, D.; Xiang, Z.; Sorenson, N.B et al. Aza-scan of the Potent Melanocortin Receptor Agonist. *Chem. Biol. Drug. Des. 2006*; 67: 275-283.
Bowers, C. Y.; Momany, F. A.; Reynolds, G. A.; Hong, A.; Newlander, K. On the in vitro and in vivo activity of a new synthetic hexapeptide that acts on the pituitary to specifically release growth hormone. *Endocrinology 1984*, 114, 1537-1545.

(Continued)

*Primary Examiner* — Robert A Wax
*Assistant Examiner* — Jessica Worsham
(74) *Attorney, Agent, or Firm* — Nixon & Vanderhye P.C.

(57) ABSTRACT

An azapeptide derivative of growth hormone releasing peptide (GHRP) of Formula I: A-(Xaa)$_a$-N(R$^A$)—N(R$^B$)—C(O)-(Xaa')$_b$-B which binds to CD 36.

2 Claims, 4 Drawing Sheets

OTHER PUBLICATIONS

Bowers CY. Growth hormone-releasing peptides .*Cell Mol Life Sci. 1998*; 93: 1316-1329.

Bradamante, S.; Ferraccioli, R.; Pagani, G. A. The reaction of sodium 1,3-diphenyl-2-azapropenide with 1,2-epoxycyclohexane. *J. Chem. Soc., Perkin Tram. 1, 3*, 1987, 515-518.

Campochiaro PA. Retinal and choroidal neovascularisation. *J cell Physiol 2000*; 97: 10242-10247.

Chang, C.D.; Meienhofer, J. Solid-phase peptide synthesis using mild base cleavage of N alpha-fluorenylmethyloxycarbonylamino acids, exemplified by a synthesis of dihydrosomatostatin. *Int. J. Pept. Protein Res.* 1978, 11, 246.

De Gennaro-Colonna V, Rossoni G, Bernareggi M et al. Cardiac ischemia and impairment of vascular endothelium function in hearts from growth hormone-deficient rats: protection by hexarelin. *Eur J Pharmacol.* 1997; 334: 201-207.

De Jong P. Age related macular degeneration. *New Engl.J. Med.* 2006: 355:1474-1485.

Demers A, Mc Nicoll N, Febbraio M et al. Identification of the growth hormone-releasing peptide binding site in CD36: a photoaffinity cross linking study. *BiochemJ 2004*; 381: 417-24.

Diez, E.; Lopez, A. M.; Pareja, C.; Martin, E.; Fernandez, R.; Lassaletta, J. M. Direct synthesis of dithioketals from N,N-dialkylhydrazones. *Tetrahedron Lett.* 1998, 39, 7955-7958.

Dithmar S, Curcio CA, Le NA et al. Ultrastructural changes in Bruch's membrane of apolipoprotein E-deficient mice. *Investigative Opthalmology &visual Science 2000*; 41 : 2035-2042.

Duthaler, R. O. Recent developments in the stereoselective synthesis of α-amino acids. *Tetrahedron* 1994, 50, 1539-1650.

Endemann G, Stanton LW, Madden S et al..CD36 is a receptor for oxidized low density lipoprotein. *J. Biol. Chem 1993*; 268: 11811-11816.

Enders, D.; Wortmann, L.; Peters, R. Recovery of Carbonyl Compounds from N,N-Dialkylhydrazones. *Acc. Chem. Res.* 2000, 33, 157-169.

Ershov A and Bazan NG. Induction of cyclooxygenase-2 gene expression in retinal pigment epithelium cells by photoreceptor rod outer segment phagocytosis and growth factors. *J Neurosci Res*; 1999 58:254-261.

Eye study group. Preclinical and phase 1A clinical evaluation of an anti-VEGF pegylated aptamer (EYE001) for the.treatment of exudative age-related macular degeneration .*Retina 2002*; 22: 143-152.

Falb, E.; Yechezkel, T.; Salitra, Y.; Gilon, C. In situ generation of Fmoc-amino acid chlorides using bis-(trichloromethyl)carbonate and its utilization for difficult couplings in solid-phase peptide synthesis. *J. Pept. Res.* 1999, 53, 507-517.

Febbraio et al., CD36: a class B scavenger receptor involved in angiogenesis , artherosclerosis, inflammation and lipid metabolism, 2001, *J. Clin. Invest.*, 108(6):785-791.

Fehrentz, J. A.; Martinez, J.; Boeglin, D.; Guerlavais, V.; Deghenghi, R. I. Growth hormone secretagogues: past, present and future. *Drugs* 2002, 5, 804-814.

Finnemann SC, Bonilha VL, Marmostein AD et al. Phagocytosis of rod outer segments by retinal pigment pigment epithelium. Proc Natl Acad Sci USA 1997; 94:12932-12937.

Friedman E. The role of the atherosclerotic process in the pathogenesis of age-related macular degeneration .*Am J Opthalmol 2000*; 130: 658-663.

Gante, J. Azapeptides. *Synthesis* 1989, 405.

Gibson, C.; Goodman S.L.; Hahn, D.; Hölzemann, G.; Kessler, H. Novel Solid-Phase Synthesis of Azapeptides and Azapeptoides via Fmoc-Strategy and Its Application in the Synthesis of RGF-Mimetics. *J. Org.Chem.*, 1999, 64, 7388-7394.

Gray, C. J.; Quibell, M.; Bagget, N.; Hammerle, T. Incorporation of azaglutamine residues into peptides synthesized by the ultra-high load solid (gel)-phase technique. *Int. J Pept. Protein Res.* 1992, 40, 351-362.

Green WR and Key NN. Senile macular degeneration: a histopathologic study. *Trans Am Opthalmol soc 1977*; 75: 180-254.

Hart, T. W.; Guillochon, D.; Perrier, G.; Sharp, B. W.; Toft, M. P.; Vacher, B.; Walsh, R. J. A. The synthesis of RP 66471. A potent potassium channel opener. *Tetrahedron Lett.* 1992, 33, 7211-7214.

Hood JD, Cheresh DA. Building a better Trap. *Proc Natl Acad. Sci USA 2003*; 100: 8624-8625.

Howard AD, Feighner SD, Cully DF et al. A receptor in pituitary and hypothalamus that functions in growth hormone release. *Science* 1996:273: 974-977.

Ishibashi T, Miki K, Sorgente N et al. Effects of intravitreal administration of steroids on experimental subretinal neovascularization in the subhuman primate .*Arch Opthalmol 1985*; 103: 708-711.

Jimenez B, Volpert OV, Crawford SE et al. Signals leading to apoptosis—dependent inhibition of neovascularization by thrombospondin1. *Nat med 2000*; 6: 41-48.

Jonas JB, Degenring RF, Kreissig I et al. Intraocular pressure elevation after intravitreal triamcinolone acetonide injection. *Opthalmology 2005*; 112: 593-598.

Kaiser, E.; Colescott, R. L.; Bassinger, C. D.; Cook, P. I. Color test for detection of free terminal amino groups in the solid-phase synthesis of peptides. *Anal. Biochem.* 1970, 34, 595-598.

Korbonits, M.; Goldstone, A. P.; Guerguiev, M.; Grossman, A. B. Ghrelin—a hormone with multiple functions. *Front Neuroendocrinol.* 2004, 25, 27-68.

Krzystolik MG, Afshari MA, Adamis AP et al. Prevention of experimental choroidal neovascularization with intravitreal anti-vascular endothelial growth factor antibody fragments. *Arch Opthalmol 2002*; 120: 338-346.

Liley, M.; Johnson, T. Solid-phase synthesis of azapeptides utilizing reversible amide bond protection to prevent hydantoin formation. *Tetrahedron Lett.* 2000, 41, 3983-3985.

Lubell, W.D.; Blankenship, J.W.; Fridkin, G.; Kaul, R. Product class 11: Peptides. Science of Synthesis 2005, 21, 713-809.

Marleau S, Harb D, Bujold K et al. EP 80317, a ligand of the CD36 scavenger receptor, protects apolipoproteinE-deficient mice from developing atherosclerotic lesions. *FASEB J 2005*; 19:1869-1871.

Meienhofer, J.; Waki, M.; Heimer, E. D.; Lambros, T. J.; Makofske, R. C.; Chang, C. D. Solid phase synthesis without repetitive acidolysis. Preparation of leucyl-alanyl-glycyl-valine using 9-fluorenylmethyloxycarbonylamino acids. *Int. J. Pept. Protein Res.* 1979, 13,35-42.

Melendez, R. E.; Lubell, W. D. Aza-Amino Acid Scan for Rapid Identification of Secondary Structure Based onN-Boc-Aza1-Dipeptides in Peptide Synthesis. *J. Am. Chem. Soc.* 2004; 126: 6759-6764.

Mino, T.; Yamashita, M. Synthesis of 2-alkyl-2-methyl-3-butenonitriles via alkylation of 2-methyl-2-butenal N,N-dimethylhydrazone. *J. Org. Chem.* 1996, 61, 1159-1160.

Morley et al., Antibacterial activity and uptake into Escherichia coli of backbone-modified analogues of small peptides, *Journal of General Microbiology*, 129(12):3701-3708, Dec. 1983.

Motohiro K, Kazuhito Y, Noriaki K et al. Scavenger receptors for oxidized lipoprotein in age-related macular degeneration *Invest. Opthalmol.Vis.Sci.2007*; 48: 1801-1807.

Mousseaux D, Le Gallic,Ryan J et al. Regulation of ERK1/2 activity by ghrelin activated growth hormone secretagogue receptor R1A involves a PLC/PKC epsilon pathway. *Brit J Pharmacol.* 2006; 148: 350-365.

Murphy JE, Tedbury PR, Homer-Vannasinkam S et al. Biochemistry and cell biology of mammalian scavenger receptors. *Atherosclerosis 2005*; 182:1-15.

Mwaikambo et al., Activation ofCD36 Inhibits and Induces Regression of Inflammatory Corneal Neovascularization, Invest. Ophthalmol. Vis. Sei., Oct. 2006, vol. 47(10), p. 4356-4364.

Nakamura, E.; Kubota, K.; Sakata, G. Addition of Zincated Hydrazone to Vinyl Grignard Reagent. Ketone Synthesis by One-Pot Assembly of Four Components. *J. Am. Chem. Soc.* 1997, 119, 5457-5458.

O'Donnell, M.J.; et. al. Acidities of glycine Schiff bases and alkylation of their conjugate bases *J. Am. Chem. Soc.* 1988, 110, 8520-8525.

O'Donnell, M.J.; Delgado, F.; Hostettler, C.; Schwesinger, R. An efficient homogeneous catalytic enantioselective synthesis of α-amino acid derivatives. *Tetrahedron Lett.* 1998, 39, 8775-8778.

Pietsch A, weber C, Goretzski M et al. N-3 but not N-6 fatty acids reduce the expression of the combined adhesion and scavenger receptor CD36 in human monocytic cells. *Cell Biochem Funct. 1995*; 13: 211-216.

Quibell, M.; Turnell, W. G.; Johnson, T. Synthesis of azapeptides by the Fmoc/tert-butyl/polyamide technique. *J. Chem. Soc.,Perkin Trans. 1* 1993, 2843-2849.

Rakoczy E. , P., Yu, M.J., Nusinowitz, S., Chang, B., and Heckenlively, J.R. 2006. Mouse models of age-related macular degeneration. *Exp Eye Res* 82:741-752.

Rattner A, Nathans J. Macular degeneration: recent advances and therapeutic opportunities. *Nature Reviews Neuroscienc. 2006*; 7:860-872.

Rink, H. Solid-phase synthesis of protected peptide fragments using a trialkoxy-diphenyl-methylester resin. *Tetrahedron Lett.* 1987, 28, 3787-3790.

Roth F, Bindewald A, Holz FG. Keypathophysiologic pathways in age-related macular disease.*Graefes Arch Clin Exp Opthalmo 2004*; 242:710-716.

Rudolf M, Ivandic B, Winkler J et al. Accumulation of lipid particles in Bruch's membrane of LDL receptor knockout mice as a model of age—related macular degeneration. *Opthalmoloe 2004*; 101:715-719.

Saishin Y, Silva RL, Callahan K et al. Periocular injection of microspheres containing PKC412 inhibits choroidal neovascularisation in a porcine model .*Invest. Opthalmol . Vis.Sci. 2003*; 44:4989-4993.

Sarks SH. Ageing and degeneration in the macular region: a clinicopathological study. *Brit J opthalmol 1976*; 60:324-341.

Shen J, Samul R, Silva RL et al. Suppression of ocular neovascularization with SiRNA targeting VEGF receptor. *Gene Ther 2005*; 13:225-234.

Shima DT, AdamisAP, Ferrara N et al. Hypoxic induction of endothelial cell growth factors in retinal cells: identification and characterization of vascular endothelial growth factor (VEGF) as the mitogen. *Mol Med 1995*; 1: 182-193.

Slakter JS. Anecortave acetate as monotherapy for treatment of subfoveal neovascularisation in age-related macular degeneration: twelve-month clinical outcomes. *Opthalmology 2003*; 110:2372-2383.

Sturino, C.F.; Fallis, A.G. Samarium(II) Iodide Induced Radical Cyclizations of Halo- and Carbonylhydrazones. *J. Am. Chem. Soc.* 1994, 116, 7447-7448.

Takeda A, Hata Y, Shiose S et al. Suppression of experimental choroidal neovascularization utilizing KDR selective receptor tyrosine kinase inhibitor . *Graefes Arch.Clin. exp.Opthalmol 2003*; 241:1122-1129.

Tolentino MJ, Brucker AJ, Fosnot J et al. Intravitreal injection of vascular endothelial growth factor small interfering RNA inhibits growth and leakage in a non human primate laser-induced model of choroidal neovascularisation . *Retina 2004*;24 :660.

Torrini, I.; Zecchini, G. P.; Paradisi, M. P.; Mastropietro, G.; Lucente, G.; Gavuzzo, E.; Mazza, F. Topographically constrained aromatic $\alpha$-aza-amino acids. Part 2. New azaTic-containing peptides: synthesis, conformation, and intramolecular NH-N interaction. *Tetrahedron* 1999, 55, 2077-2090.

Vingerling Jr., Dielemans I, Bots MI et al. Age-related macular degeneration is associated with atherosclerosis. The Rotterdam study. *Am J Epidemiol 1995*; 142: 404-409.

Wheelan J. First clinical data on RNAi. *Drug discov Today 2005*;10:1014-15.

Wieczerzak, E.; Drabik, P.; Lankiewicz, L.; Oldziej, S.; Grzonka, Z.; Abrahamson, M.; Grubb, A.; Bromme, D. Azapeptides Structurally Based upon Inhibitory Sites of Cystatins as Potent and Selective Inhibitors of Cysteine Proteases. *J. Med. Chem.* 2002, 45, 4202-4211.

Wilson, R.D.; Watson, S.P; Richards, S.A. Solid phase synthesis of 5-aminopyrazoles and derivatives. Part II. *Tetrahedron Lett.* 1998, 39, 2827-2830.

Yang, J.; Song, H.; Xiao, X.; Wang, J.; Qin; Y. Biomimetic approach to perophoramidine and communesin via an intramolecular cyclopropanation reaction. *Org. Lett.* 2006, 8(10), 2187-2190.

Supplementary European Search Report dated Jan. 28, 2011 issued in connection with EP 08 77 2825.

International Search Report and Written Opinion dated Sep. 10, 2008 issued connection with PCT/CA2008/001162.

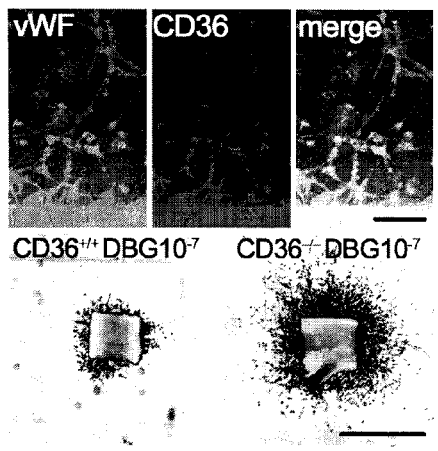
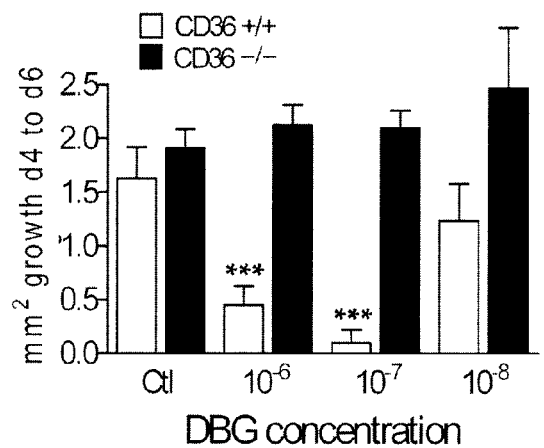
Figure 1a
Figure 1b
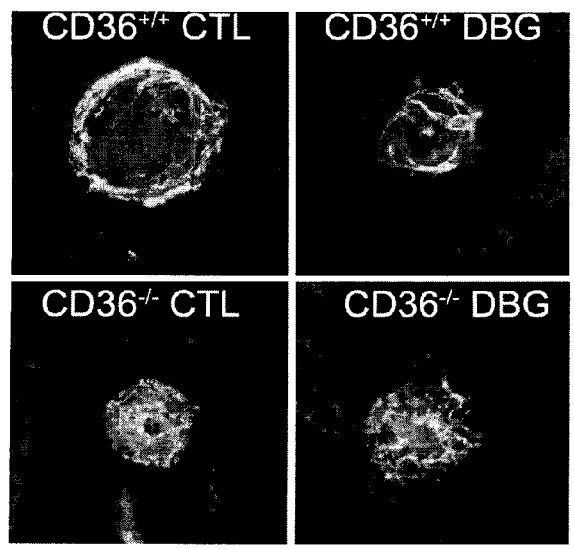
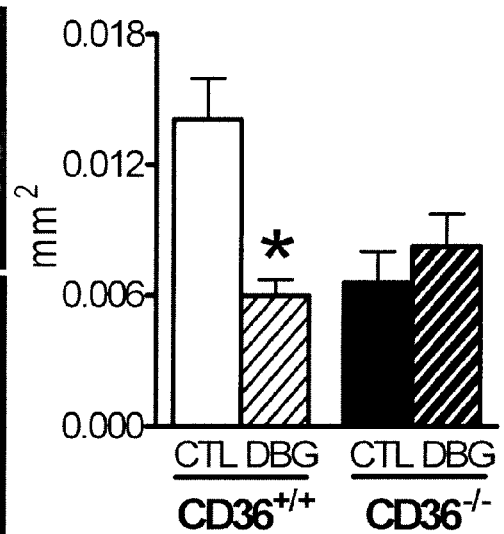
Figure 2a
Figure 2b

2ai : -NH-(Xaa)n = D-Phe-Lys(NBoc)

2bi : -NH-(Xaa)n = Trp(NBoc)-D-Phe-Lys(NBoc)

Abbreviations –NH-(Xaa)n refers to supported dipeptide [D-Phe-Lys] and tripeptide [Trp-D-Phe-Lys] start sequences.

Abbreviations –NH-(Xaa)n refers to either dipeptide [D-Phe-Lys] or tripeptide [Trp-D-Phe-Lys] start sequences, bound to commercially available NovaPEG Rink Amide resin™, and R-X refers to alkyl, aryl or heteroaryl chlorides, bromides and iodides as electrophiles.

Abbreviations –NH-(Xaa)n refer to either dipeptide [D-Phe-Lys] or tripeptide [Trp-D-Phe-Lys] start sequences bound to commercially available NovaPEG Rink Amide resin, and R refers to alkyl, aryl and heteroaryl side-chains as represented in structures 7ai – 7gi

AZAPEPTIDES AS CD36 BINDING COMPOUNDS

CROSS-REFERENCE TO RELATED APPLICATIONS

This application is a National Entry Application of PCT application no. PCT/CA2008/001162 filed on Jun. 18, 2008, and published in English under PCT Article 21(2). This application further claims the benefit of U.S. provisional application No. 60/944,712, filed on Jun. 18, 2007. All documents above are incorporated herein in their entirety by reference.

FIELD OF INVENTION

The present invention concerns azapeptides as CD36 binding compounds, and methods of making said azapeptides.

BACKGROUND OF THE INVENTION

Age-related macular degeneration (AMD) is one of the leading causes of irreversible vision loss in the western world accounting for 75% of legal blindness of the population of age 50 and older in developed countries (1). The prevalence of AMD which is of 0.05% before 50 years old, rises to 11.8% after 80 years of age and is expected to double in the coming decades because of the projected increase in aging populations (2, 3).

The causes of AMD are poorly understood, but it is agreed that the progressive decline of vision in AMD results from the dysfunction of the central retina principally its underlying elements, the retinal pigment epithelium (RPE), the Bruch membrane (BM), the choriocapillaris and degeneration of the photoreceptors (4). Other than age, few predisposing factors have been clearly identified; these include light, cigarette smoking, possibly hypertension and atherosclerosis (5). In this context, despite their specific characteristics an analogy between deposits found in AMD and atherosclerosis has been proposed (6).

Early AMD is characterized by focal or diffuse sub-RPE debris in BM (Drusen and basal deposits respectively), changes in RPE pigmentation and by thinning and obliteration of the choriocapillary layer (4). Two clinical forms of late AMD are identified: the non-exudative form characterized by geographic atrophy of RPE and choroid (geographic atrophy, GA) and the exudative form, which also includes choroidal neovascularisation (CNV) (7). Although the non-exudative form is disabling due to patchy defects in the central visual field, it is the choroidal neovascularisation of the exudative form that leads to blindness via its leaky vessels that prone to subretinal exsudations and hemorraghes (1) leading to the destruction of macular photoreceptors. The clinical features common for both types of AMD include the deposition of amorphous white deposits of phospholipids and oxidized lipoproteins (drusen), and inflammatory mediators that develop between the RPE and the BM as well as the hypo/hyperpigmentation of the RPE.

Although the underlying pathogenesis and its sequence that leads to AMD is not yet defined, the key pathophysiological steps have been summarized as 1) impaired transport between the RPE and the choriocapillaris leads to debris accumulation in the interposed BM, 2) deposition of drusen leads to RPE and photoreceptor degeneration, and 3) deregulation of the balance of pro- and anti-angiogenic factors leading to choroidal involution or neovascularisation (CNV). As CNV is a key factor in preserving vision in the aged population, the development of therapeutic agents that impairs CNV has been considered for the treatment of AMD (8).

The development of CNV in AMD has been thought to be induced by the hypoxia due to the reduced diffusion of oxygen and nutrients from the choroid to the retinal pigment epithelium (RPE) following the thickening of Bruchs membrane resulting from the deposit of lipid and protein material (9). This hypoxia conjugated with the choroid hypoperfusion induces a significant upregulation of the expression of VEGFs and VEGFRs in the RPE cells as well as in the endothelial cells of the choriocapillaris (10, 11) promoting therefore angiogenesis in age related macular degeneration.

The treatment strategies in AMD are mainly targeted to inhibit the ocular neovascularisation by blocking the expression or the activity of VEGFs and its receptors.

The blocking the expression of VEGF and its receptor has been approached by the silencing RNA technology. Silencing VEGF using SiRNA technique has been proposed by Acuity Pharmaceuticals in the development of Cand 5 (12). Intravitreal injection of Cand 5 was found to inhibit the neovascular growth without systemic toxicity.

The same approach of the siRNA technique to downregulate the expression of VEGFR-1 following the intravitreal and periocular injections of Sirna-027 has been proposed by SIRNA therapeutics (13). It was found effective in reducing choroidal and retinal neovascularisation (14). However, the long-term effect of SiRNA approaches remains to be documented.

The most frequent antiangiogenesis approach in the treatment of AMD consists of the inhibition of VEGF binding using specific aptamer, anti-VEGF antibodies or sVEGFRs.

The first development of aptamer (Pegaptanib), a covalent conjugate of an oligonucleotide and PEG that binds to the extracellular isoforms of VEGF was initiated for the treatment of neovascular AMD. Although this innovative approach appears highly promising, it does not reduce the CNV development and is unable to improve overall vision (15).

The anti VEGF therapy using the recombinant humanized Fab derived from the anti-VEGF murine monoclonal antibody (Ranibizumab) or the full-length anti-VEGF monoclonal humanised antibody (Bevacizumab) has been reported to be effective in preventing the formation of CNV (16) with a significant decrease in central retinal thickness. Although, the therapy using antibodies against VEGF which inhibits all VEGF isoforms has a drawback since VEGF is also a survival factor for neuronal cells and a fundamental requisite for the maintenance of the fenestration of the choriocapillaris which is necessary for the physiological function of the choroid itself, the retinal pigment epithelium and the outer retina. The chronic inhibition of VEGF could lead to the atrophy of these tissues.

The development of a fusion protein featuring a higher binding affinity to VEGF which combines extracellular domains of VEGFR-1 and 2 to The Fc portion on IgG1 (VEGF-TRAP) has been shown to inhibit CNV following its systemic administration. However, the adverse effect of hypertensive crisis following systemic administration of this ligand prevented further exploration in the treatment of AMD (17).

Blocking VEGF activity by interfering with its signalling pathways has been explored. Effectively, VEGF binding to its receptors leads to the phosphorylation of cytoplasmic signalling proteins such as PI3 kinase, MAP kinase and PKC. The selective inhibition of isoforms of PKC by SU 5416 (18) (a VEGF inhibitor) or PKC412 (19) reduces CNV development with less angiographic leakage. However, systemic adverse reactions such as nausea and hepatic toxicity have been reported.

The inhibition of the cellular effect of VEGF with the use of intravitreal steroids has been considered for the treatment of neovascular AMD and exudative retinal diseases. Triamcinolone acetonide has been shown to feature angiostatic effect in animal models with CNV (20). The combination of intravitreal steroid treatment with photodynamic therapy appears to give better vision outcomes (21). However, the major disadvantages of such treatment consist of the rise of intraocular pressure with the progression of cataracts (22). The new generation of modified steroids (cortesines) such as Anecortave acetate, which is devoid of glucocorticoid and mineralocorticoid activities responsible for the steroid-associated adverse effects is in evaluation for the prevention of AMD development (23).

Thus, there is still a need to develop antiangiogenic strategies to stop the neovascular growth and leakage in the treatment of AMD. Recent reports have shown that the accumulation of oxidized lipoproteins in the RPE cells and Bruchs membrane, which is consistent with the accumulation of cholesterol esters and phospholipid-containing debris in the Bruchs membrane, is paralleled with that of macrophages in the AMD lesions (24). The macrophages express scavenger receptors and may accumulate for the uptake of oxidized lipoproteins. Suppressing the macrophage accumulation by controlling macrophage responses to oxidative lipoproteins and phospholipid oxidation might be complementary for the treatment of AMD (24).

Among the seven families known of scavenger receptors, CD36 a type B scavenger receptor has been shown to be involved in multiple functions: (1) cellular energy uptake as a long chain fatty acid (LCFA) receptor (25), (2) clearance of oxidized low density lipoprotein (oxLDL) (26), (3) phagocytosis of retinal outer segments (ROS) for the recycling of spent photoreceptor disks (27), (4) mediation of the antiangiogenic effect of thrombospondin-1 (28). Interestingly, CD36 was found expressed in RPE, microvascular endothelial cells and in microglia (29) which are major cell types in AMD as well as in macrophages found in CNV membranes (24). Its expression could be upregulated by oxLDL and by other oxidative and oxidation-prone products including docosahexaenoic acids a predominant fatty acid in retinal tissue particularly the outer segment (30). As the oxidation process increases with age, oxidized lipoproteins are internalized for subsequent degradation by these cells. A deficiency in the clearance of these oxidized lipids as observed in the LDL-R null or ApoE null mice (31, 32) resulted in the accumulation of debris (drusen) in subRPE and BM. The localization of CD36, its scavenging function towards oxidized lipids and its modulatory role in angiogenesis, makes this receptor an interesting potential candidate for the genesis of AMD by way of lipid build up in BM, retinal degeneration, and vascular obliteration resulting ultimately in the development of neovascularisation.

Growth hormone-releasing peptides (GHRPs) consist of a family of small synthetic peptides derived from enkephalins that were developed as growth hormone secretagogues (33). These peptides feature high affinity binding to the ghrelin receptor (GHS-R1a) a G-coupled receptor mainly expressed in the hypothalamus and are involved in the stimulation of growth hormone-release (34). Besides their endocrine activity, GHRPs feature GH-independent cardioprotective activity in improving post-ischemic cardiac dysfunction (35) and antiatherosclerotic activity, preventing the development of atherosclerotic plaques in the ApoE null mice model (36). This beneficial effect appears to be CD36-dependent and might be due, at least in part, to the reduction of the oxLDL uptake by macrophages and to the increase of cholesterol and phospholipid efflux from macrophages through the activation of transcription factors PPARγ and LXRα and the ABC transporters (37). The peripheral activity of GHRPs might be mediated by their interaction with the scavenger receptor CD36 as shown by covalent photolabelling study with a photoactivatable derivative of hexarelin, the hexapeptide prototype of GHRPs (38) which binds also with high affinity to the GHS-R1a receptor (34).

SUMMARY OF THE INVENTION

A novel class of azapeptide compounds has been discovered, which are analogs of growth hormone-releasing peptide-6 (GHRP-6). It has been demonstrated that the compounds are antiangiogenic and that they inhibit the development of choroidal neovascularisation in vivo in a CD36 dependent manner. The compounds selectively bind to CD36 with loss of binding activity at the ghrelin receptor GHS-R1a as shown by binding studies. Furthermore, the compounds inhibit in vitro vascular sprouting of aortic endothelium. The compounds also inhibit choroidal neovascularisation in vivo as assessed using the model of laser injury induced neovascularisation. Thus, the compounds can be used to treat choroidal neovascularisation in age-related macular degeneration and in other forms of neovascularisation related diseases.

According to an aspect of the present invention there is provided an azapeptide compound of Formula I:

wherein
a is an integer from 0 to 5;
b is an integer from 0 to 5;
Xaa and Xaa' are each any D or L amino acid residue or a D,L amino acid residue mixture;
A is
1) H,
2) $C_1$-$C_6$ alkyl,
3) $C_2$-$C_6$ alkenyl,
4) $C_2$-$C_4$ alkynyl,
5) $C_3$-$C_7$ cycloalkyl,
6) haloalkyl,
7) heteroalkyl,
8) aryl,
9) heteroaryl,
10) heteroalkyl,
11) heterocyclyl,
12) heterobicyclyl,
13) $C(O)R^3$,
14) $SO_2R^3$,
15) $C(O)OR^3$, or
16) $C(O)NR^4R^5$,
wherein the alkyl, the alkenyl, the alkynyl and the cycloalkyl are optionally substituted with one or more $R^1$ substituents; and wherein the aryl, the heteroaryl, the heterocyclyl and the heterobicyclyl are optionally substituted with one or more $R^2$ substituents;
B is
1) OH,
2) $OR^3$, or
3) $NR^4R^5$;

$R^A$ and $R^B$ are independently chosen from
1) H,
2) $C_1$-$C_6$ alkyl,
3) $C_2$-$C_6$ alkenyl,
4) $C_2$-$C_6$ alkynyl,
5) $C_3$-$C_7$ cycloalkyl,
6) $C_5$-$C_7$ cycloalkenyl,
7) haloalkyl,
8) heteroalkyl,
9) aryl,
10) heteroaryl,
11) heterobicyclyl, or
12) heterocyclyl,
wherein the alkyl, alkenyl, alkynyl and the cycloalkyl and cycloalkenyl are optionally substituted with one or more $R^1$ substituents; and wherein the aryl, the heteroaryl, the heterocyclyl and the heterobicyclyl are optionally substituted with one or more $R^2$ substituents,
or alternatively, $R^A$ and $R^B$ together with the nitrogen to which each is bonded form a heterocyclic or a heterobicyclic ring;
$R^1$ is
1) halogen,
2) $NO_2$,
3) CN,
4) haloalkyl,
5) $C_3$-$C_7$ cycloalkyl,
6) aryl,
7) heteroaryl,
8) heterocyclyl,
9) heterobicyclyl,
10) $OR^6$,
11) $S(O)_2R^3$,
12) $NR^4R^5$,
13) $NR^4S(O)_2R^3$,
14) $COR^6$,
15) $C(O)OR^6$,
16) $CONR^4R^5$,
17) $S(O)_2NR^4R^5$,
18) $OC(O)R^6$,
19) $SC(O)R^3$,
20) $NR^6C(O)NR^4R^5$,
21) heteroalkyl,
22) $NR^6C(NR^6)NR^4R^5$, or
23) $C(NR^6)NR^4R^5$;
wherein the aryl, heteroaryl, heterocyclyl, and heterobicyclyl are optionally substituted with one or more $R^2$ substituents;
$R^2$ is
1) halogen,
2) $NO_2$,
3) CN,
4) $C_1$-$C_6$ alkyl,
5) $C_2$-$C_6$ alkenyl,
6) $C_2$-$C_4$ alkynyl,
7) $C_3$-$C_7$ cycloalkyl,
8) haloalkyl,
9) $OR^6$,
10) $NR^4R^5$,
11) $SR^6$,
12) $COR^6$,
13) $C(O)OR^6$,
14) $S(O)_2R^3$,
15) $CONR^4R^5$,
16) $S(O)_2NR^4R^5$,
17) aryl,
18) heteroaryl,
19) heterocyclyl,
20) heterobicyclyl,
21) heteroalkyl,
22) $NR^6C(NR^6)NR^4R^5$, or
23) $C(NR^6)NR^4R^5$,
wherein the aryl, the heteroaryl, the heterocyclyl, and the heterobicyclyl are optionally substituted with one or more $R^7$ substituents;
$R^3$ is
1) $C_1$-$C_6$ alkyl,
2) $C_2$-$C_6$ alkenyl,
3) $C_2$-$C_4$ alkynyl,
4) $C_3$-$C_7$ cycloalkyl,
5) haloalkyl,
6) aryl,
7) heteroaryl,
8) heterocyclyl, or
9) heterobicyclyl,
wherein the alkyl, the alkenyl, the alkynyl and the cycloalkyl are optionally substituted with one or more $R^1$ substituents; and wherein the aryl, the heteroaryl, the heterocyclyl and the heterobicyclyl are optionally substituted with one or more $R^2$ substituents;
$R^4$ and $R^5$ are independently chosen from
1) H,
2) $C_1$-$C_6$ alkyl,
3) $C_2$-$C_6$ alkenyl,
4) $C_2$-$C_6$ alkynyl,
5) aryl,
6) heteroaryl, or
7) heterocyclyl,
or $R^4$ and $R^5$ together with the nitrogen to which they are bonded form a heterocyclic ring;
$R^6$ is
1) H,
2) $C_1$-$C_6$ alkyl,
3) $C_2$-$C_6$ alkenyl,
4) $C_2$-$C_6$ alkynyl,
5) aryl,
6) heteroaryl, or
7) heterocyclyl;
$R^7$ is
1) halogen,
2) $NO_2$,
3) CN,
4) $C_1$-$C_6$ alkyl,
5) $C_2$-$C_6$ alkenyl,
6) $C_2$-$C_4$ alkynyl,
7) $C_3$-$C_7$ cycloalkyl,
8) haloalkyl,
9) $OR^6$,
10) $NR^4R^5$,
11) $SR^6$,
12) $COR^6$,
13) $C(O)OR^6$,
14) $S(O)_2R^3$,
15) $CONR^4R^5$,
16) $S(O)_2NR^4R^5$,
17) heteroalkyl,
18) $NR^6C(NR^6)NR^4R^5$, or
19) $C(NR^6)NR^4R^5$;
or a salt thereof, or a prodrug thereof;
wherein the following compounds are excluded:
A is H, $(Xaa)_a$ is His-D-Trp, $R^A$ is H, $R^B$ is $CH_3$, $(Xaa')_b$ is Trp-D-Phe-Lys and B is $NH_2$;
A is H, $(Xaa)_a$ is His-D-Trp-Ala-Trp, $R^A$ is H, $R^B$ is $CH_2Ph$, $(Xaa')_b$ is Lys and B is $NH_2$;
A is H, $(Xaa)_a$ is (D/L)-His, $R^A$ is H, $R^B$ is $CH_2$-p-$C_6H_4OH$, $(Xaa')_b$ is Ala-Trp-D-Phe-Lys and B is $NH_2$;

A is H, (Xaa)$_a$ is His-D-Trp-Ala, $R^A$ is H, $R^B$ is CH$_2$-p-C$_6$H$_4$OH, (Xaa')$_b$ is D-Phe-Lys and B is NH$_2$; and A is H, (Xaa)$_a$ is His-D-Trp-Ala-D-Phe, $R^A$ is H, $R^B$ is —(CH$_2$)$_4$NH$_2$, $_b$ is 0, and B is NH$_2$.

In one embodiment, a is an integer from 1 to 5 and b is an integer from 1 to 5.

In another aspect of the invention, there is provided a pharmaceutical composition comprising a compound of Formula I, as described above, with one or more of a pharmaceutically acceptable carrier, diluent or excipient.

In another aspect of the invention there is provided a method of preparing the pharmaceutical composition as described above, the method comprising: mixing the compound of Formula I, as described above, with the one or more of the pharmaceutically acceptable carrier, diluent or excipient.

From another aspect, there is also provided is a method of inhibiting CD36-dependent vascularization in vitro or in vivo, inhibiting choroidal neovascularization in vitro or in vivo, or inhibiting angiogenesis in vitro or in vivo, the method comprising: contacting CD36 with a compound of Formula I, as described above, in an amount sufficient to inhibit the vascularization, the choroidal neovascularization or the angiogenesis.

From another aspect, there is also provided a method of treating macular degeneration in a subject, or treating atherosclerosis in a subject, the method comprising: administering to the subject in need thereof a therapeutically effective amount of a compound of Formula I, as described above, to treat the macular degeneration or the atherosclerosis.

From yet another aspect, there is provided a method of detecting CD36 in a biological sample, the method comprising: a) contacting the biological sample with an amount of a compound of Formula I, as described above, wherein the compound is detectably labeled; and b) detecting the labeled compound bound to the CD36.

From a yet further aspect, there is provided a method of inhibiting angiogenesis in vitro or in vivo, inhibiting CD36-dependent vascularization in vitro or in vivo, inhibiting choroidal neovascularization in vitro or in vivo, treating macular degeneration in a subject, or treating atherosclerosis in a subject, the method comprising: contacting CD36 with a compound of Formula I, in an amount sufficient to inhibit angiogenesis, vascularization or choroidal neovascularization, or administering to the subject in need thereof a therapeutically effective amount of a compound of Formula I, to treat the macular degeneration or the atherosclerosis, wherein Formula I is defined as:

A-(Xaa)$_a$-N(R$^A$)—N(R$^B$)—C(O)-(Xaa')$_b$-B    I wherein
a is an integer from 0 to 5;
b is an integer from 0 to 5;
Xaa and Xaa' are each any D or L amino acid residue or a D,L amino acid residue mixture;
A is
1) H,
2) C$_1$-C$_6$ alkyl,
3) C$_2$-C$_6$ alkenyl,
4) C$_2$-C$_4$ alkynyl,
5) C$_3$-C$_7$ cycloalkyl,
6) haloalkyl,
7) heteroalkyl,
8) aryl,
9) heteroaryl,
10) heteroalkyl,
11) heterocyclyl,
12) heterobicyclyl,
13) C(O)R$^3$,
14) SO$_2$R$^3$,
15) C(O)OR$^3$, or
16) C(O)NR$^4$R$^5$,
wherein the alkyl, the alkenyl, the alkynyl and the cycloalkyl are optionally substituted with one or more R$^1$ substituents; and wherein the aryl, the heteroaryl, the heterocyclyl and the heterobicyclyl are optionally substituted with one or more R$^2$ substituents;
B is
1) OH,
2) OR$^3$, or
3) NR$^4$R$^5$;
R$^A$ and R$^B$ are independently chosen from
1) H,
2) C$_1$-C$_6$ alkyl,
3) C$_2$-C$_6$ alkenyl,
4) C$_2$-C$_6$ alkynyl,
5) C$_3$-C$_7$ cycloalkyl,
6) C$_5$-C$_7$ cycloalkenyl,
7) haloalkyl,
8) heteroalkyl,
9) aryl,
10) heteroaryl,
11) heterobicyclyl, or
12) heterocyclyl,
wherein the alkyl, alkenyl, alkynyl and the cycloalkyl and cycloalkenyl are optionally substituted with one or more R$^1$ substituents; and wherein the aryl, the heteroaryl, the heterocyclyl and the heterobicyclyl are optionally substituted with one or more R$^2$ substituents,
or alternatively, R$^A$ and R$^B$ together with the nitrogen to which each is bonded form a heterocyclic or a heterobicyclic ring;
R$^1$ is
1) halogen,
2) NO$_2$,
3) CN,
4) haloalkyl,
5) C$_3$-C$_7$ cycloalkyl,
6) aryl,
7) heteroaryl,
8) heterocyclyl,
9) heterobicyclyl,
10) OR$^6$,
11) S(O)$_2$R$^3$,
12) NR$^4$R$^5$,
13) NR$^4$S(O)$_2$R$^3$,
14) COR$^6$,
15) C(O)OR$^6$,
16) CONR$^4$R$^5$,
17) S(O)$_2$NR$^4$R$^5$,
18) OC(O)R$^6$,
19) SC(O)R$^3$,
20) NR$^6$C(O)NR$^4$R$^5$,
21) heteroalkyl,
22) NR$^6$C(NR$^6$)NR$^4$R$^5$, or
23) C(NR$^6$)NR$^4$R$^5$;
wherein the aryl, heteroaryl, heterocyclyl, and heterobicyclyl are optionally substituted with one or more R$^2$ substituents;
R$^2$ is
1) halogen,
2) NO$_2$,
3) CN,
4) C$_1$-C$_6$ alkyl,
5) C$_2$-C$_6$ alkenyl, 6) $C_2$-$C_4$ alkynyl,
7) $C_3$-$C_7$ cycloalkyl,
8) haloalkyl,
9) $OR^6$,
10) $NR^4R^5$,
11) $SR^6$,
12) $COR^6$,
13) $C(O)OR^6$,
14) $S(O)_2R^3$,
15) $CONR^4R^5$,
16) $S(O)_2NR^4R^5$,
17) aryl,
18) heteroaryl,
19) heterocyclyl,
20) heterobicyclyl,
21) heteroalkyl,
22) $NR^6C(NR^6)NR^4R^5$, or
23) $C(NR^6)NR^4R^5$,
wherein the aryl, the heteroaryl, the heterocyclyl, and the heterobicyclyl are optionally substituted with one or more $R^7$ substituents;
$R^3$ is
1) $C_1$-$C_6$ alkyl,
2) $C_2$-$C_6$ alkenyl,
3) $C_2$-$C_4$ alkynyl,
4) $C_3$-$C_7$ cycloalkyl,
5) haloalkyl,
6) aryl,
7) heteroaryl,
8) heterocyclyl, or
9) heterobicyclyl,
wherein the alkyl, the alkenyl, the alkynyl and the cycloalkyl are optionally substituted with one or more $R^1$ substituents; and wherein the aryl, the heteroaryl, the heterocyclyl and the heterobicyclyl are optionally substituted with one or more $R^2$ substituents;
$R^4$ and $R^5$ are independently chosen from
1) H,
2) $C_1$-$C_6$ alkyl,
3) $C_2$-$C_6$ alkenyl,
4) $C_2$-$C_6$ alkynyl,
5) aryl,
6) heteroaryl, or
7) heterocyclyl,
or $R^4$ and $R^5$ together with the nitrogen to which they are bonded form a heterocyclic ring;
$R^6$ is
1) H,
2) $C_1$-$C_6$ alkyl,
3) $C_2$-$C_6$ alkenyl,
4) $C_2$-$C_6$ alkynyl,
5) aryl,
6) heteroaryl, or
7) heterocyclyl;
$R^7$ is
1) halogen,
2) $NO_2$,
3) CN,
4) $C_1$-$C_6$ alkyl,
5) $C_2$-$C_6$ alkenyl,
6) $C_2$-$C_4$ alkynyl,
7) $C_3$-$C_7$ cycloalkyl,
8) haloalkyl,
9) $OR^6$,
10) $NR^4R^5$,
11) $SR^6$,
12) $COR^6$,
13) $C(O)OR^6$,
14) $S(O)_2R^3$,
15) $CONR^4R^5$,
16) $S(O)_2NR^4R^5$,
17) heteroalkyl,
18) $NR^6C(NR^6)NR^4R^5$, or
19) $C(NR^6)NR^4R^5$;
or a salt thereof, or a prodrug thereof.

In one embodiment, a is an integer from 1 to 5 and b is an integer from 1 to 5;

In another aspect of the present invention, there is provided use of a compound of Formula I, as described immediately above, for treating macular degeneration, psoriasis, warts, Kaposi Sarcoma, transplant arteriopathy, obesity, tumor growth, allergic dermatis, scar keloids, pyogenic granulomas, retinopathy of prematurity, diabetic retinopathy, primary pulmonary hypertension, asthma, nasal polyps, inflammatory bowel, periodontal disease, ascites, uterine bleeding, endometriosis, persistent hyperplastic vitreous syndrome, ovarian cysts, carvenous hemangioma, synovitis, osteomyelitis, arthritis, atherosclerosis, hypercholesterolemia and cardiovascular disease associated with atheriosclerosis.

From another aspect, there is provided a method of solid phase synthesis of azapeptides, such as the azapeptides defined above, the method comprising:

a) providing an amino acid or a peptide chain bound to a solid support;

b) constructing an N-terminal semicarbazone onto an amine bound to the solid support;

c) introducing side chains;

e) deconstruction of the semicarbazones;

f) cleavage of the azapeptides from the support.

The cleavage step can be performed as described in Boeglin et al (39), or any other suitable method.

The construction of an N-terminal semicarbazone onto an amine bound to the solid support can comprise incorporating activated aza-glycine residues into the peptide chain or amino acid by treating aldeyhyde or ketone-derived hydrazones with a phosgene equivalent. One example of an aldeyhyde or ketone-derived hydrazone is arylhydrazones.

Alternatively, this may also be achieved by activation of the resin-bound peptide or amino acid with a phosgene equivalent and treatment with a hydrazone, or by treating the same intermediate with a hydrazine to form the respective semicarbazide which would be reacted with an aldehyde or ketone to give the semicarbazone.

The side chains can be introduced by region-selective alkylation of the semicarbazones.

Alternatively, side chains may be added by a variety of related methods including a) cross-coupling chemistry of the semicarbazone with aryl and heteroaryl halides or triflates, b) Michael additions of semicarbazone to unsaturated electrophiles such as alpha,beta-unsaturated esters, c) Mitsunobu alkylations with alcohols, or d) alkylations with epoxides and similar strained ring systems such as aziridines. Any other suitable methods are also included. Deconstruction of the semicarbazones can include reduction of the semicarbazone. This can be performed using a method similar to the reduction of carbazates as shown in Boeglin et al (39), as well as nucleophilic attack of the semicarbazone by a method similar to the nucleophilic addition to carbazates (as in Friestad, G. K.; Ji, A. Org. Lett.; (Letter); 2008; 10(11); 2311-2313 and refs therein). Moreover, the semicarbazone may serve as an intermediate for heterocycle synthesis at the N-terminal of the peptide chain by methods such as those used on hydrazones like the synthesis of 1,3,4-Trisubstituted Pyrazoles by Deng, X.; Mani, N. S. Org. Lett.; (Letter); 2008; 10(6); 1307-1310.

An optional step of the method may includes acylation of the aza-amino acid residue, as described in Boeglin et al (39) and Melendez et al (40).

Another optional step may comprise normal SPPS sequence including coupling as described in Blankenship et al (68(b)).

The method may further comprise an additional step of protecting a side group followed by deprotecting the side group before cleavage of the azapeptide from the support.

Advantageously, by providing access to a diverse array of aza-amino acid analogs from a common aza-glycine precursor, this method may be useful for studying structure activity relationships to address questions on the importance of stereochemisty, side-chain functionality and conformation on peptide activity.

BRIEF DESCRIPTION OF THE DRAWINGS

These and other features of the invention will become more apparent from the following description in which reference is made to the appended drawings wherein:

FIG. 1a illustrates sprouting aortic endothelium (Von Willebrand factor positive) expressing CD36 on the upper row compared to vascular sprouting of aortic rings from C57BL/6 and CD36 null mice in presence of DBG 178 at $10^{-7}$M in the lower row for azapeptide compound DBG178 to demonstrate disruption of vascular sprouting of aortic endothelium;

FIG. 1b is a histogram of microvascular sprouts areas (mean±s.e.m) from aortic explants of C57BL/6 and CD36 null mice exposed to concentrations from $10^{-8}$ to $10^{-6}$M $p<0.01$ of DBG 178 compared with control (Ctl);

FIG. 2a illustrates choroidal vessels detected using FITC-conjugated dextran infusion following laser-induced posterior retinal injury in eyes from 10-week-old male C57BL/6 mice and CD36 deficient mice of the same background with or without intravitreal treatment with azapeptide compound DBG178;

FIG. 2b is a histogram of the surfaces of neovascular vessels obtained from C57BL/6 ($CD36_{+/+}$) and CD36 null ($CD36-/-$) mice with (DBG) or without (Ctl) treatment with azapeptide compound DBG178;

DETAILED DESCRIPTION

Definitions

Figure 3:
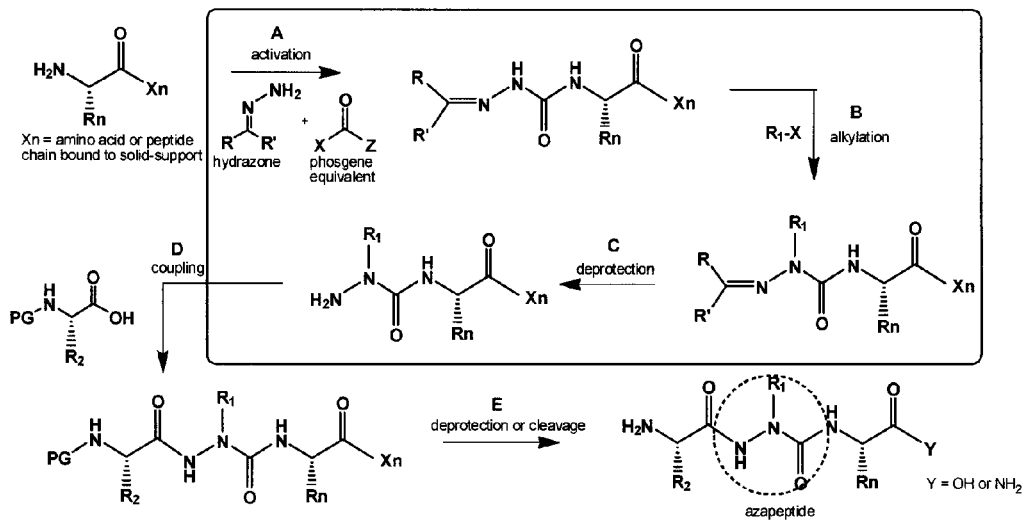
FIG. 3 illustrates a general scheme for the synthesis of aza-peptides according to another aspect of the present invention.

Unless otherwise specified, the following definitions apply:

The singular forms "a", "an" and "the" include corresponding plural references unless the context clearly dictates otherwise.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of". Thus the phrase "consisting of" indicates that the listed elements are required or mandatory and that no other elements may be present.

As used herein, the term "amino acid" is intended to mean at least any of the following α-amino acids:

| Amino acid | Abbreviation |
|---|---|
| Alanine | Ala |
| Arginine | Arg |
| Aspartic acid | Asp |
| Asparagine | Asn |
| Cysteine | Cys |
| Glutamic acid | Glu |
| Glutamine | Gln |
| Glycine | Gly |
| Isoleucine | Ile |
| Histidine | His |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

The above list is not exclusive and it should be understood that other amino acids not listed above are included in the definition of amino acid, such as hydroxyproline, citruline, ornithine etc.

The natural amino acids, with the exception of glycine, contain a chiral carbon atom. Unless otherwise stated, the compounds of Formula I containing amino acids can be of either the L- or D-configuration, or can be mixtures of D- and L-isomers, including racemic mixtures. Additional non-natural amino acid residues which are contemplated include, but are not limited to, α-alkyl, α,α-dialkyl, α-aryl and α-heteroarylglycine analogs, aryl and heteroarylalanine analogs, β,β-dialkylcysteine analogs, β,β-dialkylserine analogs, branched leucine analogs, ornithine, cirtuline, sarcosine, allylglycine, aminobutyric acid, amino-iso-butyric acid, cyclohexylalanine, cyclohexylglycine (also named: 2-amino-2-cyclohexylacetic acid), norvaline, pipecolic acid, tert-butylglycine, and the like. Also included are β amino acids such as beta-alanine, beta-homophenylalanine as well as longer chain amino acids such as gamma-aminobutyric acid.

As used herein, the term "residue" when referring to α-amino acids is intended to mean a radical derived from the corresponding α-amino acid by eliminating the hydroxyl of the carboxy group and one hydrogen of the α-amino group. For example, the terms Gln, Ala, Gly, Ile, Arg, Asp, Phe, Ser, Leu, Cys, Asn, and Tyr represent the residues of glutamine, alanine, glycine, isoleucine, arginine, aspartic acid, phenylalanine, serine, leucine, cysteine, asparagine, and tyrosine, respectively.

As used herein, the term "alkyl" is intended to include both branched and straight chain saturated aliphatic hydrocarbon groups having the specified number of carbon atoms, for example, $C_1$-$C_6$ as in $C_1$-$C_6$-alkyl is defined as including groups having 1, 2, 3, 4, 5 or 6 carbons in a linear or branched arrangement. Examples of alkyl as defined above include, but are not limited to, methyl, ethyl, n-propyl, i-propyl, n-butyl, t-butyl, i-butyl, pentyl and c-hexyl.

As used herein, the term, "alkenyl" is intended to mean unsaturated straight or branched chain hydrocarbon groups having the specified number of carbon atoms therein, and in which at least two of the carbon atoms are bonded to each other by a double bond, and having either E or Z regeochemistry and combinations thereof. For example, $C_2$-$C_6$ as in $C_2$-$C_6$ alkenyl is defined as including groups having 1, 2, 3, 4, 5, or 6 carbons in a linear or branched arrangement, at least two of the carbon atoms being bonded together by a double bond. Examples of $C_2$-$C_6$ alkenyl include ethenyl (vinyl), 1-propenyl, 2-propenyl, 1-butenyl and the like.

As used herein, the term "alkynyl" is intended to mean unsaturated, straight chain hydrocarbon groups having the specified number of carbon atoms therein and in which at least two carbon atoms are bonded together by a triple bond. For example $C_2$-$C_4$ as in $C_2$-$C_4$ alkynyl is defined as including groups having 2, 3, or 4 carbon atoms in a chain, at least two of the carbon atoms being bonded together by a triple bond.

As used herein, the term "cycloalkyl" is intended to mean a monocyclic saturated aliphatic hydrocarbon group having the specified number of carbon atoms therein, for example, $C_3$-$C_7$ as in $C_3$-$C_7$ cycloalkyl is defined as including groups having 3, 4, 5, 6 or 7 carbons in a monocyclic arrangement. Examples of $C_3$-$C_7$ cycloalkyl as defined above include, but are not limited to, cyclopropyl, cyclobutyl, cyclopentyl, cyclohexyl and cycloheptyl.

As used herein, the term "cycloalkenyl" is intended to mean unsaturated straight or branched chain hydrocarbon groups having the specified number of carbon atoms therein in a monocyclic arrangement, and in which at least two of the carbon atoms are bonded to each other by a double bond. For example, $C_2$-$C_8$ as in $C_2$-$C_8$ cycloalkenyl is defined as having 2, 3, 4, 5, 6, 7 or 8 carbons in a monocyclic arrangement. Examples of cycloalkenyls as defined above include, but are not limited to cyclopentenyl, cyclohexenyl, cyclohexadienyl, cycloheptenyl, cyclooctenyl, and cyclooctadienyl.

As used herein, the term "halo" or "halogen" is intended to mean fluorine, chlorine, bromine and iodine.

As used herein, the term "haloalkyl" is intended to mean an alkyl, as defined above, in which each hydrogen atom may be successively replaced by a different halogen atom. Examples of haloalkyls include, but are not limited to, $CH_2F$, $CHF_2$ and $CF_3$.

As used herein, the term "heteroalkyl" is intended to mean a saturated linear or branched-chain monovalent hydrocarbon radical of one to six carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein.

As used herein, the term "aryl", either alone or in combination with another radical, means a carbocyclic aromatic monocyclic group containing 6 carbon atoms, which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl. The fused aryls may be connected to another group either at a suitable position on the cycloalkyl ring or the aromatic ring. For example:

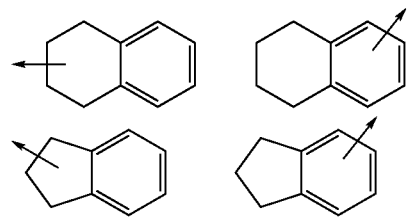

Arrowed lines drawn from the ring system indicate that the bond may be attached to any of the suitable ring atoms.

As used herein, the term "heteroaryl" is intended to mean a monocyclic or bicyclic ring system of up to ten atoms, wherein at least one ring is aromatic, and contains from 1 to 4 hetero atoms selected from the group consisting of O, N, and S. The heteroaryl substituent may be attached either via a ring carbon atom or one of the heteroatoms. Examples of heteroaryl groups include, but are not limited to thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, isoindolinyl, thiazolo[4,5-b]-pyridine, hydroxybenzotriazolyl, benzotriazoyl, triazoyl, and fluoroscein derivatives such as:

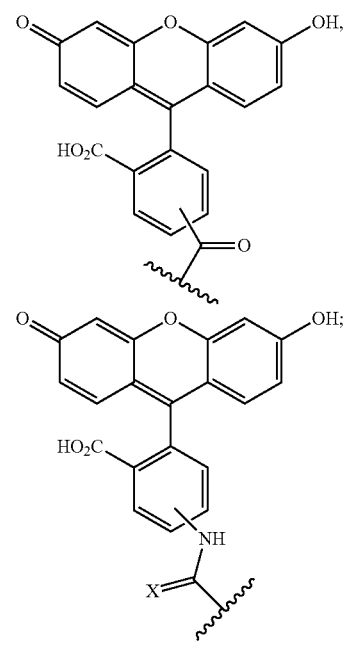

and rhodamine, dansyl and other fluorescent tags known to those skilled in the art.

As used herein, the term "heterocycle", "heterocyclic" or "heterocyclyl" is intended to mean a non-aromatic ring system containing heteroatoms selected from the group consisting of O, N and S. Examples of aromatic heterocycles are described as heteroaromatic above. Examples of non-aromatic heterocycles include, but are not limited to azepinyl, azetidyl, aziridinyl, pyrrolidinyl, tetrahydrofuranyl, piperidyl, pyrrolinyl, piperazinyl, imidazolidinyl, morpholinyl, imidazolinyl, diazepinyl, pyrazolidinyl, pyrazolinyl, and biotinyl derivatives.

As used herein, the term "heterobicycle" either alone or in combination with another radical, is intended to mean a heterocycle as defined above fused to another cycle, be it a heterocycle, an aryl or any other cycle defined herein. Examples of such heterobicycles include, but are not limited to, pyrrolizidinyl, indolizidinyl, quinolizidinyl, coumarin, benzo[d][1,3]dioxole, 2,3-dihydrobenzo[b][1,4]dioxine and 3,4-dihydro-2H-benzo[b][1,4]dioepine.

As used herein, the term "detectable label" is intended to mean a group that may be linked to an azapeptide compound of the present invention to produce a probe or to a CD36 binding domain, such that when the probe is associated with the CD36 binding domain, the label allows either direct or indirect recognition of the probe so that it may be detected, measured and quantified.

As used herein, the term "affinity tag" is intended to mean a ligand or group, which is linked to either an azapeptide compound of the present invention or to a CD36 binding domain to allow another compound to be extracted from a solution to which the ligand or group is attached.

As used herein, the term "probe" is intended to mean an azapeptide compound of Formula I which is labeled with either a detectable label or an affinity tag, and which is capable of binding, either covalently or non-covalently, to a CD36 binding domain. When, for example, the probe is non-covalently bound, it may be displaced by a test compound. When, for example, the probe is bound covalently, it may be used to form cross-linked adducts, which may be quantified and inhibited by a test compound.

As used herein, the term "optionally substituted with one or more substituents" or its equivalent term "optionally substituted with at least one substituent" is intended to mean that the subsequently described event of circumstances may or may not occur, and that the description includes instances where the event or circumstance occurs and instances in which it does not. The definition is intended to mean from zero to five substituents.

If the substituents themselves are incompatible with the synthetic methods of the present invention, the substituent may be protected with a suitable protecting group (PG) that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Examples of protecting groups used throughout include, but are not limited to Alloc, Fmoc, Bn, Boc, CBz and COCF$_3$. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

As used herein, the term "subject" is intended to mean humans and non-human mammals such as primates, cats, dogs, swine, cattle, sheep, goats, horses, rabbits, rats, mice and the like.

As used herein, the term "prodrug" is intended to mean a compound that may be converted under physiological conditions or by solvolysis to a biologically active compound of the present invention. Thus, the term "prodrug" refers to a precursor of a compound of the invention that is pharmaceutically acceptable. A prodrug may be inactive or display limited activity when administered to a subject in need thereof, but is converted in vivo to an active compound of the present invention. Typically, prodrugs are transformed in vivo to yield the compound of the invention, for example, by hydrolysis in blood or other organs by enzymatic processing. The prodrug compound often offers advantages of solubility, tissue compatibility or delayed release in the subject (see, Bundgard, H., Design of Prodrugs (1985), pp. 7-9, 21-24 (Elsevier, Amsterdam). The definition of prodrug includes any covalently bonded carriers, which release the active compound of the invention in vivo when such prodrug is administered to a subject. Prodrugs of a compound of the present invention may be prepared by modifying functional groups present in the compound of the invention in such a way that the modifications are cleaved, either in routine manipulation or in vivo, to a parent compound of the invention.

As used herein, the term "pharmaceutically acceptable carrier, diluent or excipient" is intended to mean, without limitation, any adjuvant, carrier, excipient, glidant, sweetening agent, diluent, preservative, dye/colorant, aerosol spray, flavor enhancer, surfactant, wetting agent, dispersing agent, suspending agent, stabilizer, isotonic agent, solvent, emulsifier, or encapsulating agent, such as a liposome, cyclodextrins, encapsulating polymeric delivery systems or polyethylene glycol matrix, which is acceptable for use in the subject, preferably humans.

As used herein, the term "pharmaceutically acceptable salt" is intended to mean both acid and base addition salts.

As used herein, the term "pharmaceutically acceptable acid addition salt" is intended to mean those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

As used herein, the term "pharmaceutically acceptable base addition salt" is intended to mean those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

As used herein, the term "therapeutically effective amount" is intended to mean an amount of an azapeptide compound of Formula I which, when administered to a subject is sufficient to effect treatment for a disease-state in which modulation of CD36 activity, such as inhibition or activation, is desired (The activation of CD36 by the endogenous ligand TSP-1 induces the apoptosis of endothelial cells). The amount of the compound of Formula I will vary depending on the compound, the condition and its severity, and the age of the subject to be treated, but can be determined routinely by one of ordinary skill in the art having regard to his own knowledge and to this disclosure.

As used herein, the term "treating" or "treatment" is intended to mean treatment of a disease-state in which inhibition of CD36 activity is desired, as disclosed herein, in a subject, and includes, for example: (i) preventing a disease or condition, in which inhibition of CD36 activity is desired, from occurring in a subject, in particular, when such mammal is predisposed to the disease or condition but has not yet been diagnosed as having it; (ii) inhibiting a disease or condition associated with CD36 activity, i.e., arresting its development; or (iii) relieving a disease or condition associated with CD36 activity, i.e., causing regression of the condition.

As used herein, the term "$IC_{50}$" is intended to mean an amount, concentration or dosage of a particular compound of the present invention that achieves a 50% inhibition of a maximal response measured under the same experimental conditions but in the absence of the compound.

As used herein, the term "$EC_{50}$" is intended to mean an amount, concentration or dosage of a particular compound of the present invention that achieves a 50% inhibition of cell survival measured under the same experimental conditions but in the absence of the compound.

The compounds of the present invention, or their pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present invention is intended to include all such possible isomers, as well as, their epimeric, racemic and optically pure forms. Optically active (+) and (−), (R)- and (S)-, or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using enantiomerically pure reagents, substrates, catalysts, or solvents or by converting one enantiomer to another by asymmetric transformation.

Certain compounds of the present invention may exist in Zwitterionic form and the present invention includes Zwitterionic forms of these compounds and mixtures thereof.

I: Azapeptide Compounds

This invention relates to a novel class of azapeptide compounds of Formula I which are derivatives of GHRP-6 and which bind specifically to the scavenger receptor CD36. The selective replacement of amino acids of GHRP-6 by aza-aminoacid residue in promoting the aromatic interactions at the ends of the peptide chain improves the binding selectivity towards the scavenger receptor CD36 and to decrease binding affinity for the ghrelin receptor GSH-R1a.

One subset of compounds of Formula I comprise compounds in which Xaa is $Xaa_1$, $Xaa_2$, $Xaa_3$ or $Xaa_4$, wherein $Xaa_1$, $Xaa_2$, $Xaa_3$ and $Xaa_4$ are each a D or L amino acid residue, and in which Xaa' is $Xaa'_1$, $Xaa'_2$, $Xaa'_3$ or $Xaa'_4$, wherein $Xaa_1$, $Xaa_2$, $Xaa_3$ and $Xaa_4$ are each a D or L amino acid residue.

One subset of azapeptide compounds of Formula I comprise azapeptide compounds of the following Formula I.1:

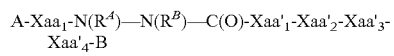

$$A\text{-}Xaa_1\text{-}N(R^A)\text{—}N(R^B)\text{—}C(O)\text{-}Xaa'_1\text{-}Xaa'_2\text{-}Xaa'_3\text{-}Xaa'_4\text{-}B \qquad \text{I.1}$$

wherein
$Xaa_1$, $Xaa'_1$, $Xaa'_2$, $Xaa'_3$, and $Xaa'_4$ are each any D or L amino acid residue or a D,L amino acid residue mixture;

A is
1) H,
2) $C_1$-$C_6$ alkyl,
3) $C_2$-$C_6$ alkenyl,
4) $C_2$-$C_4$ alkynyl,
5) $C_3$-$C_7$ cycloalkyl,
6) haloalkyl,
7) heteroalkyl,
8) aryl,
9) heteroaryl,
10) heteroalkyl,
11) heterocyclyl,
12) heterobicyclyl,
13) $C(O)R^3$,
14) $SO_2R^3$,
15) $C(O)OR^3$, or
16) $C(O)NR^4R^5$,
wherein the alkyl, the alkenyl, the alkynyl and the cycloalkyl are optionally substituted with one or more $R^1$ substituents; and wherein the aryl, the heteroaryl, the heterocyclyl and the heterobicyclyl are optionally substituted with one or more $R^2$ substituents;

B is
1) OH,
2) $OR^3$, or
3) $NR^4R^5$;

$R^A$ and $R^B$ are independently chosen from
1) H,
2) $C_1$-$C_6$ alkyl,
3) $C_2$-$C_6$ alkenyl,
4) $C_2$-$C_6$ alkynyl,
5) $C_3$-$C_7$ cycloalkyl,
6) $C_5$-$C_7$ cycloalkenyl,
7) haloalkyl,
8) heteroalkyl,
9) aryl,
10) heteroaryl,
11) heterobicyclyl, or
12) heterocyclyl,
wherein the alkyl, alkenyl, alkynyl and the cycloalkyl and cycloalkenyl are optionally substituted with one or more $R^1$ substituents; and wherein the aryl, the heteroaryl, the heterocyclyl and the heterobicyclyl are optionally substituted with one or more $R^2$ substituents, or alternatively, $R^A$ and $R^B$ together with the nitrogen to which each is bonded form a heterocyclic or a heterobicyclic ring;

$R^1$ is
1) halogen,
2) $NO_2$,
3) CN,
4) haloalkyl,
5) $C_3$-$C_7$ cycloalkyl,
6) aryl,
7) heteroaryl,
8) heterocyclyl,
9) heterobicyclyl,
10) $OR^6$,
11) $S(O)_2R^3$,
12) $NR^4R^5$,
13) $NR^4S(O)_2R^3$,
14) $COR^6$,
15) $C(O)OR^6$,
16) $CONR^4R^5$,
17) $S(O)_2NR^4R^5$,
18) $OC(O)R^6$,
19) $SC(O)R^3$,
20) $NR^6C(O)NR^4R^5$,
21) heteroalkyl,
22) $NR^6C(NR^6)NR^4R^5$, or
23) $C(NR^6)NR^4R^5$;
wherein the aryl, heteroaryl, heterocyclyl, and heterobicyclyl are optionally substituted with one or more $R^2$ substituents;

$R^2$ is
1) halogen,
2) $NO_2$,
3) CN,
4) $C_1$-$C_6$ alkyl,
5) $C_2$-$C_6$ alkenyl,
6) $C_2$-$C_4$ alkynyl,
7) $C_3$-$C_7$ cycloalkyl,
8) haloalkyl,
9) $OR^6$,
10) $NR^4R^5$,
11) $SR^6$,
12) $COR^6$,
13) $C(O)OR^6$,
14) $S(O)_2R^3$,
15) $CONR^4R^5$,
16) $S(O)_2NR^4R^5$,
17) aryl,
18) heteroaryl,
19) heterocyclyl,
20) heterobicyclyl,
21) heteroalkyl,
22) $NR^6C(NR^6)NR^4R^5$, or
23) $C(NR^6)NR^4R^5$,
wherein the aryl, the heteroaryl, the heterocyclyl, and the heterobicyclyl are optionally substituted with one or more $R^7$ substituents;

$R^3$ is
1) $C_1$-$C_6$ alkyl,
2) $C_2$-$C_6$ alkenyl,
3) $C_2$-$C_4$ alkynyl,
4) $C_3$-$C_7$ cycloalkyl,
5) haloalkyl,
6) aryl,
7) heteroaryl,
8) heterocyclyl, or
9) heterobicyclyl,
wherein the alkyl, the alkenyl, the alkynyl and the cycloalkyl are optionally substituted with one or more $R^1$ substituents;

and wherein the aryl, the heteroaryl, the heterocyclyl and the heterobicyclyl are optionally substituted with one or more $R^2$ substituents;

$R^4$ and $R^5$ are independently chosen from
1) H,
2) $C_1$-$C_6$ alkyl,
3) $C_2$-$C_6$ alkenyl,
4) $C_2$-$C_6$ alkynyl,
5) aryl,
6) heteroaryl, or
7) heterocyclyl,
or $R^4$ and $R^5$ together with the nitrogen to which they are bonded form a heterocyclic ring;

$R^6$ is
1) H,
2) $C_1$-$C_6$ alkyl,
3) $C_2$-$C_6$ alkenyl,
4) $C_2$-$C_6$ alkynyl,
5) aryl,
6) heteroaryl, or
7) heterocyclyl;

$R^7$ is
1) halogen,
2) $NO_2$,
3) CN,
4) $C_1$-$C_6$ alkyl,
5) $C_2$-$C_6$ alkenyl,
6) $C_2$-$C_4$ alkynyl,
7) $C_3$-$C_7$ cycloalkyl,
8) haloalkyl,
9) $OR^6$,
10) $NR^4R^5$,
11) $SR^6$,
12) $COR^6$,
13) $C(O)OR^6$,
14) $S(O)_2R^3$,
15) $CONR^4R^5$,
16) $S(O)_2NR^4R^5$,
17) heteroalkyl,
18) $NR^6C(NR^6)NR^4R^5$, or
19) $C(NR^6)NR^4R^5$;
or a salt thereof, or a prodrug thereof.

One subset of azapeptide compounds of Formula I comprise azapeptide compounds of the following Formula I.2:

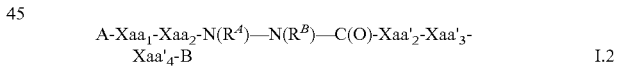

$$A\text{-}Xaa_1\text{-}Xaa_2\text{-}N(R^A)\text{---}N(R^B)\text{---}C(O)\text{-}Xaa'_2\text{-}Xaa'_3\text{-}Xaa'_4\text{-}B \qquad \text{I.2}$$

wherein
$Xaa_1$, $Xaa_2$, $Xaa'_2$, $Xaa'_3$, and $Xaa'_4$ are each any D or L amino acid residue or a D,L amino acid residue mixture;

A is
1) H,
2) $C_1$-$C_6$ alkyl,
3) $C_2$-$C_6$ alkenyl,
4) $C_2$-$C_4$ alkynyl,
5) $C_3$-$C_7$ cycloalkyl,
6) haloalkyl,
7) heteroalkyl,
8) aryl,
9) heteroaryl,
10) heteroalkyl,
11) heterocyclyl,
12) heterobicyclyl,
13) $C(O)R^3$,
14) $SO_2R^3$,
15) $C(O)OR^3$, or
16) $C(O)NR^4R^5$, wherein the alkyl, the alkenyl, the alkynyl and the cycloalkyl are optionally substituted with one or more $R^1$ substituents; and wherein the aryl, the heteroaryl, the heterocyclyl and the heterobicyclyl are optionally substituted with one or more $R^2$ substituents;

B is
1) OH,
2) $OR^3$, or
3) $NR^4R^5$;

$R^A$ and $R^B$ are independently chosen from
1) H,
2) $C_1$-$C_6$ alkyl,
3) $C_2$-$C_6$ alkenyl,
4) $C_2$-$C_6$ alkynyl,
5) $C_3$-$C_7$ cycloalkyl,
6) $C_5$-$C_7$ cycloalkenyl,
7) haloalkyl,
8) heteroalkyl,
9) aryl,
10) heteroaryl,
11) heterobicyclyl, or
12) heterocyclyl,
wherein the alkyl, alkenyl, alkynyl and the cycloalkyl and cycloalkenyl are optionally substituted with one or more $R^1$ substituents; and wherein the aryl, the heteroaryl, the heterocyclyl and the heterobicyclyl are optionally substituted with one or more $R^2$ substituents,
or alternatively, $R^A$ and $R^B$ together with the nitrogen to which each is bonded form a heterocyclic or a heterobicyclic ring;

$R^1$ is
1) halogen,
2) $NO_2$,
3) CN,
4) haloalkyl,
5) $C_3$-$C_7$ cycloalkyl,
6) aryl,
7) heteroaryl,
8) heterocyclyl,
9) heterobicyclyl,
10) $OR^6$,
11) $S(O)_2R^3$,
12) $NR^4R^5$,
13) $NR^4S(O)_2R^3$,
14) $COR^6$,
15) $C(O)OR^6$,
16) $CONR^4R^5$,
17) $S(O)_2NR^4R^5$,
18) $OC(O)R^6$,
19) $SC(O)R^3$,
20) $NR^6C(O)NR^4R^5$,
21) heteroalkyl,
22) $NR^6C(NR^6)NR^4R^5$, or
23) $C(NR^6)NR^4R^5$;
wherein the aryl, heteroaryl, heterocyclyl, and heterobicyclyl are optionally substituted with one or more $R^2$ substituents;

$R^2$ is
1) halogen,
2) $NO_2$,
3) CN,
4) $C_1$-$C_6$ alkyl,
5) $C_2$-$C_6$ alkenyl,
6) $C_2$-$C_4$ alkynyl,
7) $C_3$-$C_7$ cycloalkyl,
8) haloalkyl,
9) $OR^6$,
10) $NR^4R^5$,
11) $SR^6$,
12) $COR^6$,
13) $C(O)OR^6$,
14) $S(O)_2R^3$,
15) $CONR^4R^5$,
16) $S(O)_2NR^4R^5$,
17) aryl,
18) heteroaryl,
19) heterocyclyl,
20) heterobicyclyl,
21) heteroalkyl,
22) $NR^6C(NR^6)NR^4R^5$, or
23) $C(NR^6)NR^4R^5$,
wherein the aryl, the heteroaryl, the heterocyclyl, and the heterobicyclyl are optionally substituted with one or more $R^7$ substituents;

$R^3$ is
1) $C_1$-$C_6$ alkyl,
2) $C_2$-$C_6$ alkenyl,
3) $C_2$-$C_4$ alkynyl,
4) $C_3$-$C_7$ cycloalkyl,
5) haloalkyl,
6) aryl,
7) heteroaryl,
8) heterocyclyl, or
9) heterobicyclyl,
wherein the alkyl, the alkenyl, the alkynyl and the cycloalkyl are optionally substituted with one or more $R^1$ substituents; and wherein the aryl, the heteroaryl, the heterocyclyl and the heterobicyclyl are optionally substituted with one or more $R^2$ substituents;

$R^4$ and $R^5$ are independently chosen from
1) H,
2) $C_1$-$C_6$ alkyl,
3) $C_2$-$C_6$ alkenyl,
4) $C_2$-$C_6$ alkynyl,
5) aryl,
6) heteroaryl, or
7) heterocyclyl,
or $R^4$ and $R^5$ together with the nitrogen to which they are bonded form a heterocyclic ring;

$R^6$ is
1) H,
2) $C_1$-$C_6$ alkyl,
3) $C_2$-$C_6$ alkenyl,
4) $C_2$-$C_6$ alkynyl,
5) aryl,
6) heteroaryl, or
7) heterocyclyl;

$R^7$ is
1) halogen,
2) $NO_2$,
3) CN,
4) $C_1$-$C_6$ alkyl,
5) $C_2$-$C_6$ alkenyl,
6) $C_2$-$C_4$ alkynyl,
7) $C_3$-$C_7$ cycloalkyl,
8) haloalkyl,
9) $OR^6$,
10) $NR^4R^5$,
11) $SR^6$,
12) $COR^6$,
13) $C(O)OR^6$,
14) $S(O)_2R^3$,
15) $CONR^4R^5$,
16) $S(O)_2NR^4R^5$,
17) heteroalkyl, 18) $NR^6C(NR^6)NR^4R^5$, or
19) $C(NR^6)NR^4R^5$;
or a salt thereof, or a prodrug thereof.

One subset of azapeptide compounds of Formula I comprise azapeptide compounds of the following Formula I.3:

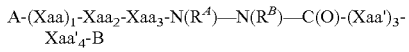
$$A\text{-}(Xaa)_1\text{-}Xaa_2\text{-}Xaa_3\text{-}N(R^A)\text{—}N(R^B)\text{—}C(O)\text{-}(Xaa')_3\text{-}Xaa'_4\text{-}B \quad\quad I.3$$

wherein
$Xaa_1$, $Xaa_2$, $Xaa_3$, $Xaa'_3$, and $Xaa'_4$ are each any D or L amino acid residue or a D,L amino acid residue mixture;

A is
1) H,
2) $C_1$-$C_6$ alkyl,
3) $C_2$-$C_6$ alkenyl,
4) $C_2$-$C_4$ alkynyl,
5) $C_3$-$C_7$ cycloalkyl,
6) haloalkyl,
7) heteroalkyl,
8) aryl,
9) heteroaryl,
10) heteroalkyl,
11) heterocyclyl,
12) heterobicyclyl,
13) $C(O)R^3$,
14) $SO_2R^3$,
15) $C(O)OR^3$, or
16) $C(O)NR^4R^5$,
wherein the alkyl, the alkenyl, the alkynyl and the cycloalkyl are optionally substituted with one or more $R^1$ substituents; and wherein the aryl, the heteroaryl, the heterocyclyl and the heterobicyclyl are optionally substituted with one or more $R^2$ substituents;

B is
1) OH,
2) $OR^3$, or
3) $NR^4R^5$;

$R^A$ and $R^B$ are independently chosen from
1) H,
2) $C_1$-$C_6$ alkyl,
3) $C_2$-$C_6$ alkenyl,
4) $C_2$-$C_6$ alkynyl,
5) $C_3$-$C_7$ cycloalkyl,
6) $C_5$-$C_7$ cycloalkenyl,
7) haloalkyl,
8) heteroalkyl,
9) aryl,
10) heteroaryl,
11) heterobicyclyl, or
12) heterocyclyl,
wherein the alkyl, alkenyl, alkynyl and the cycloalkyl and cycloalkenyl are optionally substituted with one or more $R^1$ substituents; and wherein the aryl, the heteroaryl, the heterocyclyl and the heterobicyclyl are optionally substituted with one or more $R^2$ substituents,
or alternatively, $R^A$ and $R^B$ together with the nitrogen to which each is bonded form a heterocyclic or a heterobicyclic ring;

$R^1$ is
1) halogen,
2) $NO_2$,
3) CN,
4) haloalkyl,
5) $C_3$-$C_7$ cycloalkyl,
6) aryl,
7) heteroaryl,
8) heterocyclyl,
9) heterobicyclyl,
10) $OR^6$,
11) $S(O)_2R^3$,
12) $NR^4R^5$,
13) $NR^4S(O)_2R^3$,
14) $COR^6$,
15) $C(O)OR^6$,
16) $CONR^4R^5$,
17) $S(O)_2NR^4R^5$,
18) $OC(O)R^6$,
19) $SC(O)R^3$,
20) $NR^6C(O)NR^4R^5$,
21) heteroalkyl,
22) $NR^6C(NR^6)NR^4R^5$, or
23) $C(NR^6)NR^4R^5$;
wherein the aryl, heteroaryl, heterocyclyl, and heterobicyclyl are optionally substituted with one or more $R^2$ substituents;

$R^2$ is
1) halogen,
2) $NO_2$,
3) CN,
4) $C_1$-$C_6$ alkyl,
5) $C_2$-$C_6$ alkenyl,
6) $C_2$-$C_4$ alkynyl,
7) $C_3$-$C_7$ cycloalkyl,
8) haloalkyl,
9) $OR^6$,
10) $NR^4R^5$,
11) $SR^6$,
12) $COR^6$,
13) $C(O)OR^6$,
14) $S(O)_2R^3$,
15) $CONR^4R^5$,
16) $S(O)_2NR^4R^5$,
17) aryl,
18) heteroaryl,
19) heterocyclyl,
20) heterobicyclyl,
21) heteroalkyl,
22) $NR^6C(NR^6)NR^4R^5$, or
23) $C(NR^6)NR^4R^5$,
wherein the aryl, the heteroaryl, the heterocyclyl, and the heterobicyclyl are optionally substituted with one or more $R^7$ substituents;

$R^3$ is
1) $C_1$-$C_6$ alkyl,
2) $C_2$-$C_6$ alkenyl,
3) $C_2$-$C_4$ alkynyl,
4) $C_3$-$C_7$ cycloalkyl,
5) haloalkyl,
6) aryl,
7) heteroaryl,
8) heterocyclyl, or
9) heterobicyclyl,
wherein the alkyl, the alkenyl, the alkynyl and the cycloalkyl are optionally substituted with one or more $R^1$ substituents; and wherein the aryl, the heteroaryl, the heterocyclyl and the heterobicyclyl are optionally substituted with one or more $R^2$ substituents;

$R^4$ and $R^5$ are independently chosen from
1) H,
2) $C_1$-$C_6$ alkyl,
3) $C_2$-$C_6$ alkenyl,
4) $C_2$-$C_6$ alkynyl,
5) aryl,
6) heteroaryl, or
7) heterocyclyl, or $R^4$ and $R^5$ together with the nitrogen to which they are bonded form a heterocyclic ring;
$R^6$ is
1) H,
2) $C_1$-$C_6$ alkyl,
3) $C_2$-$C_6$ alkenyl,
4) $C_2$-$C_6$ alkynyl,
5) aryl,
6) heteroaryl, or
7) heterocyclyl;
$R^7$ is
1) halogen,
2) $NO_2$,
3) CN,
4) $C_1$-$C_6$ alkyl,
5) $C_2$-$C_6$ alkenyl,
6) $C_2$-$C_4$ alkynyl,
7) $C_3$-$C_7$ cycloalkyl,
8) haloalkyl,
9) $OR^6$,
10) $NR^4R^5$,
11) $SR^6$,
12) $COR^6$,
13) $C(O)OR^6$,
14) $S(O)_2R^3$,
15) $CONR^4R^5$,
16) $S(O)_2NR^4R^5$,
17) heteroalkyl,
18) $NR^6C(NR^6)NR^4R^5$, or
19) $C(NR^6)NR^4R^5$;
or a salt thereof, or a prodrug thereof.

One subset of azapeptide compounds of Formula I comprise azapeptide compounds of the following Formula I.4:

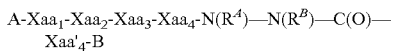

A-Xaa$_1$-Xaa$_2$-Xaa$_3$-Xaa$_4$-N($R^A$)—N($R^B$)—C(O)—Xaa'$_4$-B    I.4 wherein
Xaa$_1$, Xaa$_2$, Xaa$_3$, Xaa$_4$ and Xaa'$_4$ are each any D or L amino acid residue or a D,L amino acid residue mixture;
A is
1) H,
2) $C_1$-$C_6$ alkyl,
3) $C_2$-$C_6$ alkenyl,
4) $C_2$-$C_4$ alkynyl,
5) $C_3$-$C_7$ cycloalkyl,
6) haloalkyl,
7) heteroalkyl,
8) aryl,
9) heteroaryl,
10) heteroalkyl,
11) heterocyclyl,
12) heterobicyclyl,
13) $C(O)R^3$,
14) $SO_2R^3$,
15) $C(O)OR^3$, or
16) $C(O)NR^4R^5$,
wherein the alkyl, the alkenyl, the alkynyl and the cycloalkyl are optionally substituted with one or more $R^1$ substituents; and wherein the aryl, the heteroaryl, the heterocyclyl and the heterobicyclyl are optionally substituted with one or more $R^2$ substituents;
B is
1) OH,
2) $OR^3$, or
3) $NR^4R^5$;

$R^A$ and $R^B$ are independently chosen from
1) H,
2) $C_1$-$C_6$ alkyl,
3) $C_2$-$C_6$ alkenyl,
4) $C_2$-$C_6$ alkynyl,
5) $C_3$-$C_7$ cycloalkyl,
6) $C_5$-$C_7$ cycloalkenyl,
7) haloalkyl,
8) heteroalkyl,
9) aryl,
10) heteroaryl,
11) heterobicyclyl, or
12) heterocyclyl,
wherein the alkyl, alkenyl, alkynyl and the cycloalkyl and cycloalkenyl are optionally substituted with one or more $R^1$ substituents; and wherein the aryl, the heteroaryl, the heterocyclyl and the heterobicyclyl are optionally substituted with one or more $R^2$ substituents,
or alternatively, $R^A$ and $R^B$ together with the nitrogen to which each is bonded form a heterocyclic or a heterobicyclic ring;
$R^1$ is
1) halogen,
2) $NO_2$,
3) CN,
4) haloalkyl,
5) $C_3$-$C_7$ cycloalkyl,
6) aryl,
7) heteroaryl,
8) heterocyclyl,
9) heterobicyclyl,
10) $OR^6$,
11) $S(O)_2R^3$,
12) $NR^4R^5$,
13) $NR^4S(O)_2R^3$,
14) $COR^6$,
15) $C(O)OR^6$,
16) $CONR^4R^5$,
17) $S(O)_2NR^4R^5$,
18) $OC(O)R^6$,
19) $SC(O)R^3$,
20) $NR^6C(O)NR^4R^5$,
21) heteroalkyl,
22) $NR^6C(NR^6)NR^4R^5$, or
23) $C(NR^6)NR^4R^5$;
wherein the aryl, heteroaryl, heterocyclyl, and heterobicyclyl are optionally substituted with one or more $R^2$ substituents;
$R^2$ is
1) halogen,
2) $NO_2$,
3) CN,
4) $C_1$-$C_6$ alkyl,
5) $C_2$-$C_6$ alkenyl,
6) $C_2$-$C_4$ alkynyl,
7) $C_3$-$C_7$ cycloalkyl,
8) haloalkyl,
9) $OR^6$,
10) $NR^4R^5$,
11) $SR^6$,
12) $COR^6$,
13) $C(O)OR^6$,
14) $S(O)_2R^3$,
15) $CONR^4R^5$,
16) $S(O)_2NR^4R^5$,
17) aryl,
18) heteroaryl,
19) heterocyclyl,
20) heterobicyclyl, 21) heteroalkyl,
22) $NR^6C(NR^6)NR^4R^5$, or
23) $C(NR^6)NR^4R^5$,
wherein the aryl, the heteroaryl, the heterocyclyl, and the heterobicyclyl are optionally substituted with one or more $R^7$ substituents;

$R^3$ is
1) $C_1$-$C_6$ alkyl,
2) $C_2$-$C_6$ alkenyl,
3) $C_2$-$C_a$ alkynyl,
4) $C_3$-$C_7$ cycloalkyl,
5) haloalkyl,
6) aryl,
7) heteroaryl,
8) heterocyclyl, or
9) heterobicyclyl,
wherein the alkyl, the alkenyl, the alkynyl and the cycloalkyl are optionally substituted with one or more $R^1$ substituents; and wherein the aryl, the heteroaryl, the heterocyclyl and the heterobicyclyl are optionally substituted with one or more $R^2$ substituents;

$R^4$ and $R^5$ are independently chosen from
1) H,
2) $C_1$-$C_6$ alkyl,
3) $C_2$-$C_6$ alkenyl,
4) $C_2$-$C_6$ alkynyl,
5) aryl,
6) heteroaryl, or
7) heterocyclyl,
or $R^4$ and $R^5$ together with the nitrogen to which they are bonded form a heterocyclic ring;

$R^6$ is
1) H,
2) $C_1$-$C_6$ alkyl,
3) $C_2$-$C_6$ alkenyl,
4) $C_2$-$C_6$ alkynyl,
5) aryl,
6) heteroaryl, or
7) heterocyclyl;

$R^7$ is
1) halogen,
2) $NO_2$,
3) CN,
4) $C_1$-$C_6$ alkyl,
5) $C_2$-$C_6$ alkenyl,
6) $C_2$-$C_4$ alkynyl,
7) $C_3$-$C_7$ cycloalkyl,
8) haloalkyl,
9) $OR^6$,
10) $NR^4R^5$,
11) $SR^6$,
12) $COR^6$,
13) $C(O)OR^6$,
14) $S(O)_2R^3$,
15) $CONR^4R^5$,
16) $S(O)_2NR^4R^5$,
17) heteroalkyl,
18) $NR^6C(NR^6)NR^4R^5$, or
19) $C(NR^6)NR^4R^5$;
or a salt thereof, or a prodrug thereof.

One subset of azapeptide compounds of Formula I comprise azapeptide compounds of the following Formula I.5:

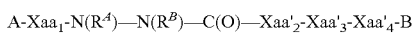  I.5 wherein
$Xaa_1$, $Xaa'_2$, $Xaa'_3$, and $Xaa'_4$ are each any D or L amino acid residue or a D,L amino acid residue mixture;

A is
1) H,
2) $C_1$-$C_6$ alkyl,
3) $C_2$-$C_6$ alkenyl,
4) $C_2$-$C_4$ alkynyl,
5) $C_3$-$C_7$ cycloalkyl,
6) haloalkyl,
7) heteroalkyl,
8) aryl,
9) heteroaryl,
10) heteroalkyl,
11) heterocyclyl,
12) heterobicyclyl,
13) $C(O)R^3$,
14) $SO_2R^3$,
15) $C(O)OR^3$, or
16) $C(O)NR^4R^5$,
wherein the alkyl, the alkenyl, the alkynyl and the cycloalkyl are optionally substituted with one or more $R^1$ substituents; and wherein the aryl, the heteroaryl, the heterocyclyl and the heterobicyclyl are optionally substituted with one or more $R^2$ substituents;

B is
1) OH,
2) $OR^3$, or
3) $NR^4R^5$;

$R^A$ and $R^B$ are independently chosen from
1) H,
2) $C_1$-$C_6$ alkyl,
3) $C_2$-$C_6$ alkenyl,
4) $C_2$-$C_6$ alkynyl,
5) $C_3$-$C_7$ cycloalkyl,
6) $C_5$-$C_7$ cycloalkenyl,
7) haloalkyl,
8) heteroalkyl,
9) aryl,
10) heteroaryl,
11) heterobicyclyl, or
12) heterocyclyl,
wherein the alkyl, alkenyl, alkynyl and the cycloalkyl and cycloalkenyl are optionally substituted with one or more $R^1$ substituents; and wherein the aryl, the heteroaryl, the heterocyclyl and the heterobicyclyl are optionally substituted with one or more $R^2$ substituents,
or alternatively, $R^A$ and $R^B$ together with the nitrogen to which each is bonded form a heterocyclic or a heterobicyclic ring;

$R^1$ is
1) halogen,
2) $NO_2$,
3) CN,
4) haloalkyl,
5) $C_3$-$C_7$ cycloalkyl,
6) aryl,
7) heteroaryl,
8) heterocyclyl,
9) heterobicyclyl,
10) $OR^6$,
11) $S(O)_2R^3$,
12) $NR^4R^5$,
13) $NR^4S(O)_2R^3$,
14) $COR^6$,
15) $C(O)OR^6$,
16) $CONR^4R^5$,
17) $S(O)_2NR^4R^5$,
18) $OC(O)R^6$,
19) $SC(O)R^3$,
20) $NR^6C(O)NR^4R^5$, 21) heteroalkyl,
22) NR⁶C(NR⁶)NR⁴R⁵, or
23) C(NR⁶)NR⁴R⁵;
wherein the aryl, heteroaryl, heterocyclyl, and heterobicyclyl are optionally substituted with one or more R² substituents;

R² is
1) halogen,
2) NO₂,
3) CN,
4) $C_1$-$C_6$ alkyl,
5) $C_2$-$C_6$ alkenyl,
6) $C_2$-$C_4$ alkynyl,
7) $C_3$-$C_7$ cycloalkyl,
8) haloalkyl,
9) OR⁶,
10) NR⁴R⁵,
11) SR⁶,
12) COR⁶,
13) C(O)OR⁶,
14) S(O)₂R³,
15) CONR⁴R⁵,
16) S(O)₂NR⁴R⁵,
17) aryl,
18) heteroaryl,
19) heterocyclyl,
20) heterobicyclyl,
21) heteroalkyl,
22) NR⁶C(NR⁶)NR⁴R⁵, or
23) C(NR⁶)NR⁴R⁵,
wherein the aryl, the heteroaryl, the heterocyclyl, and the heterobicyclyl are optionally substituted with one or more R⁷ substituents;

R³ is
1) $C_1$-$C_6$ alkyl,
2) $C_2$-$C_6$ alkenyl,
3) $C_2$-$C_4$ alkynyl,
4) $C_3$-$C_7$ cycloalkyl,
5) haloalkyl,
6) aryl,
7) heteroaryl,
8) heterocyclyl, or
9) heterobicyclyl,
wherein the alkyl, the alkenyl, the alkynyl and the cycloalkyl are optionally substituted with one or more R¹ substituents; and wherein the aryl, the heteroaryl, the heterocyclyl and the heterobicyclyl are optionally substituted with one or more R² substituents;

R⁴ and R⁵ are independently chosen from
1) H,
2) $C_1$-$C_6$ alkyl,
3) $C_2$-$C_6$ alkenyl,
4) $C_2$-$C_6$ alkynyl,
5) aryl,
6) heteroaryl, or
7) heterocyclyl,
or R⁴ and R⁵ together with the nitrogen to which they are bonded form a heterocyclic ring;

R⁶ is
1) H,
2) $C_1$-$C_6$ alkyl,
3) $C_2$-$C_6$ alkenyl,
4) $C_2$-$C_6$ alkynyl,
5) aryl,
6) heteroaryl, or
7) heterocyclyl;

R⁷ is
1) halogen,
2) NO₂,
3) CN,
4) $C_1$-$C_6$ alkyl,
5) $C_2$-$C_6$ alkenyl,
6) $C_2$-$C_4$ alkynyl,
7) $C_3$-$C_7$ cycloalkyl,
8) haloalkyl,
9) OR⁶,
10) NR⁴R⁵,
11) SR⁶,
12) COR⁶,
13) C(O)OR⁶,
14) S(O)₂R³,
15) CONR⁴R⁵,
16) S(O)₂NR⁴R⁵,
17) heteroalkyl,
18) NR⁶C(NR⁶)NR⁴R⁵, or
19) C(NR⁶)NR⁴R⁵;
or a salt thereof, or a prodrug thereof.

One subset of azapeptide compounds of Formula I comprise azapeptide compounds of the following Formula I.6:

$$A\text{-}Xaa_1\text{-}Xaa_2\text{-}N(R^A)\text{---}N(R^B)\text{---}C(O)\text{---}Xaa'_3\text{-}Xaa'_4\text{-}B \qquad I.6$$

wherein
$Xaa_1$, $Xaa_2$, $Xaa'_3$, and $Xaa'_4$ are each any D or L amino acid residue or a D,L amino acid residue mixture;

A is
1) H,
2) $C_1$-$C_6$ alkyl,
3) $C_2$-$C_6$ alkenyl,
4) $C_2$-$C_4$ alkynyl,
5) $C_3$-$C_7$ cycloalkyl,
6) haloalkyl,
7) heteroalkyl,
8) aryl,
9) heteroaryl,
10) heteroalkyl,
11) heterocyclyl,
12) heterobicyclyl,
13) C(O)R³,
14) SO₂R³,
15) C(O)OR³, or
16) C(O)NR⁴R⁵,
wherein the alkyl, the alkenyl, the alkynyl and the cycloalkyl are optionally substituted with one or more R¹ substituents; and wherein the aryl, the heteroaryl, the heterocyclyl and the heterobicyclyl are optionally substituted with one or more R² substituents;

B is
1) OH,
2) OR³, or
3) NR⁴R⁵;

$R^A$ and $R^B$ are independently chosen from
1) H,
2) $C_1$-$C_6$ alkyl,
3) $C_2$-$C_6$ alkenyl,
4) $C_2$-$C_6$ alkynyl,
5) $C_3$-$C_7$ cycloalkyl,
6) $C_5$-$C_7$ cycloalkenyl,
7) haloalkyl,
8) heteroalkyl,
9) aryl,
10) heteroaryl,
11) heterobicyclyl, or
12) heterocyclyl, wherein the alkyl, alkenyl, alkynyl and the cycloalkyl and cycloalkenyl are optionally substituted with one or more $R^1$ substituents; and wherein the aryl, the heteroaryl, the heterocyclyl and the heterobicyclyl are optionally substituted with one or more $R^2$ substituents, or alternatively, $R^A$ and $R^B$ together with the nitrogen to which each is bonded form a heterocyclic or a heterobicyclic ring;

$R^1$ is
1) halogen,
2) $NO_2$,
3) CN,
4) haloalkyl,
5) $C_3$-$C_7$ cycloalkyl,
6) aryl,
7) heteroaryl,
8) heterocyclyl,
9) heterobicyclyl,
10) $OR^6$,
11) $S(O)_2R^3$,
12) $NR^4R^5$,
13) $NR^4S(O)_2R^3$,
14) $COR^6$,
15) $C(O)OR^6$,
16) $CONR^4R^5$,
17) $S(O)_2NR^4R^5$,
18) $OC(O)R^6$,
19) $SC(O)R^3$,
20) $NR^6C(O)NR^4R^5$,
21) heteroalkyl,
22) $NR^6C(NR^6)NR^4R^5$, or
23) $C(NR^6)NR^4R^5$;
wherein the aryl, heteroaryl, heterocyclyl, and heterobicyclyl are optionally substituted with one or more $R^2$ substituents;

$R^2$ is
1) halogen,
2) $NO_2$,
3) CN,
4) $C_1$-$C_6$ alkyl,
5) $C_2$-$C_6$ alkenyl,
6) $C_2$-$C_4$ alkynyl,
7) $C_3$-$C_7$ cycloalkyl,
8) haloalkyl,
9) $OR^6$,
10) $NR^4R^5$,
11) $SR^6$,
12) $COR^6$,
13) $C(O)OR^6$,
14) $S(O)_2R^3$,
15) $CONR^4R^5$,
16) $S(O)_2NR^4R^5$,
17) aryl,
18) heteroaryl,
19) heterocyclyl,
20) heterobicyclyl,
21) heteroalkyl,
22) $NR^6C(NR^6)NR^4R^5$, or
23) $C(NR^6)NR^4R^5$,
wherein the aryl, the heteroaryl, the heterocyclyl, and the heterobicyclyl are optionally substituted with one or more $R^7$ substituents;

$R^3$ is
1) $C_1$-$C_6$ alkyl,
2) $C_2$-$C_6$ alkenyl,
3) $C_2$-$C_4$ alkynyl,
4) $C_3$-$C_7$ cycloalkyl,
5) haloalkyl,
6) aryl,
7) heteroaryl,
8) heterocyclyl, or
9) heterobicyclyl,
wherein the alkyl, the alkenyl, the alkynyl and the cycloalkyl are optionally substituted with one or more $R^1$ substituents; and wherein the aryl, the heteroaryl, the heterocyclyl and the heterobicyclyl are optionally substituted with one or more $R^2$ substituents;

$R^4$ and $R^5$ are independently chosen from
1) H,
2) $C_1$-$C_6$ alkyl,
3) $C_2$-$C_6$ alkenyl,
4) $C_2$-$C_6$ alkynyl,
5) aryl,
6) heteroaryl, or
7) heterocyclyl,
or $R^4$ and $R^5$ together with the nitrogen to which they are bonded form a heterocyclic ring;

$R^6$ is
1) H,
2) $C_1$-$C_6$ alkyl,
3) $C_2$-$C_6$ alkenyl,
4) $C_2$-$C_6$ alkynyl,
5) aryl,
6) heteroaryl, or
7) heterocyclyl;

$R^7$ is
1) halogen,
2) $NO_2$,
3) CN,
4) $C_1$-$C_6$ alkyl,
5) $C_2$-$C_6$ alkenyl,
6) $C_2$-$C_4$ alkynyl,
7) $C_3$-$C_7$ cycloalkyl,
8) haloalkyl,
9) $OR^6$,
10) $NR^4R^5$,
11) $SR^6$,
12) $COR^6$,
13) $C(O)OR^6$,
14) $S(O)_2R^3$,
15) $CONR^4R^5$,
16) $S(O)_2NR^4R^5$,
17) heteroalkyl,
18) $NR^6C(NR^6)NR^4R^5$, or
19) $C(NR^6)NR^4R^5$;
or a salt thereof, or a prodrug thereof.

One subset of azapeptide compounds of Formula I comprise azapeptide compounds of the following Formula I.7:

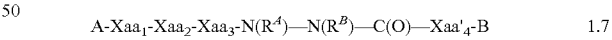

A-Xaa$_1$-Xaa$_2$-Xaa$_3$-N(R$^A$)—N(R$^B$)—C(O)—Xaa'$_4$-B     1.7 wherein
Xaa$_1$, Xaa$_2$, Xaa$_3$, and Xaa'$_4$ are each any D or L amino acid residue or a D,L amino acid residue mixture;

A is
1) H,
2) $C_1$-$C_6$ alkyl,
3) $C_2$-$C_6$ alkenyl,
4) $C_2$-$C_4$ alkynyl,
5) $C_3$-$C_7$ cycloalkyl,
6) haloalkyl,
7) heteroalkyl,
8) aryl,
9) heteroaryl,
10) heteroalkyl,
11) heterocyclyl,
12) heterobicyclyl, 13) C(O)R³,
14) SO₂R³,
15) C(O)OR³, or
16) C(O)NR⁴R⁵,
wherein the alkyl, the alkenyl, the alkynyl and the cycloalkyl are optionally substituted with one or more R¹ substituents; and wherein the aryl, the heteroaryl, the heterocyclyl and the heterobicyclyl are optionally substituted with one or more R² substituents;
Bis
1) OH,
2) OR³, or
3) NR⁴R⁵;
  R^A and R^B are independently chosen from
1) H,
2) C₁-C₆ alkyl,
3) C₂-C₆ alkenyl,
4) C₂-C₆ alkynyl,
5) C₃-C₇ cycloalkyl,
6) C₅-C₇ cycloalkenyl,
7) haloalkyl,
8) heteroalkyl,
9) aryl,
10) heteroaryl,
11) heterobicyclyl, or
12) heterocyclyl,
wherein the alkyl, alkenyl, alkynyl and the cycloalkyl and cycloalkenyl are optionally substituted with one or more R¹ substituents; and wherein the aryl, the heteroaryl, the heterocyclyl and the heterobicyclyl are optionally substituted with one or more R² substituents,
or alternatively, R^A and R^B together with the nitrogen to which each is bonded form a heterocyclic or a heterobicyclic ring;
  R¹ is
1) halogen,
2) NO₂,
3) CN,
4) haloalkyl,
5) C₃-C₇ cycloalkyl,
6) aryl,
7) heteroaryl,
8) heterocyclyl,
9) heterobicyclyl,
10) OR⁶,
11) S(O)₂R³,
12) NR⁴R⁵,
13) NR⁴S(O)₂R³,
14) COR⁶,
15) C(O)OR⁶,
16) CONR⁴R⁵,
17) S(O)₂NR⁴R⁵,
18) OC(O)R⁶,
19) SC(O)R³,
20) NR⁶C(O)NR⁴R⁵,
21) heteroalkyl,
22) NR⁶C(NR⁶)NR⁴R⁵, or
23) C(NR⁶)NR⁴R⁵;
wherein the aryl, heteroaryl, heterocyclyl, and heterobicyclyl are optionally substituted with one or more R² substituents;
  R² is
1) halogen,
2) NO₂,
3) CN,
4) C₁-C₆ alkyl,
5) C₂-C₆ alkenyl,
6) C₂-C₄ alkynyl,
7) C₃-C₇ cycloalkyl,
8) haloalkyl,
9) OR⁶,
10) NR⁴R⁵,
11) SR⁶,
12) COR⁶,
13) C(O)OR⁶,
14) S(O)₂R³,
15) CONR⁴R⁵,
16) S(O)₂NR⁴R⁵,
17) aryl,
18) heteroaryl,
19) heterocyclyl,
20) heterobicyclyl,
21) heteroalkyl,
22) NR⁶C(NR⁶)NR⁴R⁵, or
23) C(NR⁶)NR⁴R⁵,
wherein the aryl, the heteroaryl, the heterocyclyl, and the heterobicyclyl are optionally substituted with one or more R⁷ substituents;
  R³ is
1) C₁-C₆ alkyl,
2) C₂-C₆ alkenyl,
3) C₂-C₄ alkynyl,
4) C₃-C₇ cycloalkyl,
5) haloalkyl,
6) aryl,
7) heteroaryl,
8) heterocyclyl, or
9) heterobicyclyl,
wherein the alkyl, the alkenyl, the alkynyl and the cycloalkyl are optionally substituted with one or more R¹ substituents; and wherein the aryl, the heteroaryl, the heterocyclyl and the heterobicyclyl are optionally substituted with one or more R² substituents;
  R⁴ and R⁵ are independently chosen from
1) H,
2) C₁-C₆ alkyl,
3) C₂-C₆ alkenyl,
4) C₂-C₆ alkynyl,
5) aryl,
6) heteroaryl, or
7) heterocyclyl,
or R⁴ and R⁵ together with the nitrogen to which they are bonded form a heterocyclic ring;
  R⁶ is
1) H,
2) C₁-C₆ alkyl,
3) C₂-C₆ alkenyl,
4) C₂-C₆ alkynyl,
5) aryl,
6) heteroaryl, or
7) heterocyclyl;
  R⁷ is
1) halogen,
2) NO₂,
3) CN,
4) C₁-C₆ alkyl,
5) C₂-C₆ alkenyl,
6) C₂-C₄ alkynyl,
7) C₃-C₇ cycloalkyl,
8) haloalkyl,
9) OR⁶,
10) NR⁴R⁵,
11) SR⁶,
12) COR⁶,
13) C(O)OR⁶,
14) S(O)₂R³, 15) CONR$^4$R$^5$,
16) S(O)$_2$NR$^4$R$^5$,
17) heteroalkyl,
18) NR$^6$C(NR$^6$)NR$^4$R$^5$, or
19) C(NR$^6$)NR$^4$R$^5$;
or a salt thereof, or a prodrug thereof In one subset of the aforesaid azapeptide compounds of Formula I.1, I.2, I.3 and I.4, A is H such that Xaa$_1$ is any D or L amino acid residue, or a mixture thereof, with a free N-terminal NH$_2$ group.

In another subset of the aforesaid azapeptide compounds of Formula I.1, I.2, I.3 and I.4, B is NH$_2$, such that Xaa'$_4$ is any D or L amino acid residue, or a mixture thereof, with a C-terminal CONH$_2$ group.

The following compounds are excluded:
A is H, (Xaa)$_a$ is His-D-Trp, R$^A$ is H, R$^B$ is CH$_3$, (Xaa')$_b$ is Trp-D-Phe-Lys and B is NH$_2$;
A is H, (Xaa)$_a$ is His-D-Trp-Ala-Trp, R$^A$ is H, R$^B$ is CH$_2$Ph, (Xaa')$_b$ is Lys and B is NH$_2$;
A is H, (Xaa)$_a$ is (D/L)-His, R$^A$ is H, R$^B$ is CH$_2$-p-C$_6$H$_4$OH, (Xaa')$_b$ is Ala-Trp-D-Phe-Lys and B is NH$_2$;
A is H, (Xaa)$_a$ is His-D-Trp-Ala, R$^A$ is H, R$^B$ is CH$_2$-p-C$_6$H$_4$OH, (Xaa')$_b$ is D-Phe-Lys and B is NH$_2$; and
A is H, (Xaa)$_a$ is His-D-Trp-Ala-D-Phe, R$^A$ is H, R$^B$ is —(CH$_2$)$_4$NH$_2$, $_b$ is 0, and B is NH$_2$.

The antiangiogenic property of the azapeptide compounds of the present invention have been demonstrated in vitro and in vivo. One compound, DBG 178 (see Table 1), has been shown to disrupt significantly the vascular sprouting in the matrigel-embedded aortic rings exposed to concentrations of this compound ranging from 10$^{-7}$ to 10$^{-6}$ M. This inhibitory effect of DBG 178, which was not detected in the sprouting of aortic endothelium from CD36 gene knockout mice, appears to be dependent of CD36 expression. DBG178 has also been shown to inhibit the choroidal neovascularisation in vivo using the laser injury induced neovascularisation model. In this model, which can be applied to rodents and primates, a laser beam is used to disrupt the RPE and Bruchs membrane that separates the choroidal vasculature from the subretinal space. The following local inflammatory reaction in the deep retina and choroid leads to a localized subretinal neovascularisation in a similar manner as that observed in age-related macular degeneration. This local neovascularisation can be quantified on flatmounts of RPE/choroid/sclera. The intravitreal injection of DBG178 at effective concentrations of 10$^{-7}$ and 10$^{-6}$ M within the eye 3 and 7 days after the laser injury showed that DBG 178 significantly inhibited the neovascular response by more than 50%. In contrast, DBG178 had no effect on the neovascular response in the eye from CD 36 null mice. Taking together these results, one could conclude that the DBG 178 effect is mediated through the scavenger receptor CD36. DBG178 also efficiently reduces the exaggerated neovascularisation induced by the laser injury in the eye of C57/BL6 mice. In contrast, the much less neovascularisation observed in the eye of CD36 null mice following laser injury is not affected by the intravitreal injection of DBG178.

II: Utilities

The azapeptide compounds of the present invention are useful as antiangiogenic compounds by modulating CD36 activity, and as such the compounds, compositions and methods of the present invention include applications to the cells or subjects afflicted with or having a predisposition towards developing a particular disease state, for which inhibition of CD36 activity is desired. For example, the compounds, compositions and methods of the present invention can be used to treat diseases involving neovascularisation. Besides the subchoroidal neovascularisation in AMD, intravitreal neovascularisation is also observed in diabetic retinopathy, in the retinopathy of prematurity as well as in retinal vein occlusion. The compounds, compositions and methods of the present invention may inhibit the neovascularisation in such pathological conditions.

The GHRP derivative, EP 80317 was shown to serve as a ligand of CD36, and to display anti-inflammatory activity, reducing the expression of proxydative enzymes in the arterial wall (gp 91 phos and p40 phos of the NADPH oxidase, and i-Nos synthase) as well as causing the reduction of MCP-1 and VCAM, the chemokines involved in the inflammatory process. The overall effect observed was the reduction of atherosclerosis development (36). The modulation of CD36 activity by its ligand (such as GHRP or azapeptide) might result in the reduction of the inflammatory process encountered in inflammation related diseases such as inflammatory bowel and arthritis as well as atherosclerosis. As angiogenesis is a major contributor in the development of tumors, ligands of CD36 elicit antiangiogenic activity associated with the reduction of tumor growth. The natural ligand TSP-1 is known to bind CD36 at the site of its extracellular domain (93-110). Azapeptides and GHRPs, that may bind at sites distinct from that used by TSP-1, elicit antiangiogenic effects. The modulation of the activity of CD36 by its ligand may also find its application in the reduction of inflammatory processes encountered in inflammation related diseases such as inflammatory bowel, synovitis, osteomyelitis.

Thus, the compounds, compositions and methods of the present invention can be used to treat macular degeneration (whether age-related or not), psoriasis, warts, Kaposi Sarcoma, transplant arteriopathy, obesity, tumor growth, allergic dermatis, scar keloids, pyogenic granulomas, retinopathy of prematurity, diabetic retinopathy, primary pulmonary hypertension, asthma, nasal polyps, inflammatory bowel and periodontal disease, ascites, uterine bleeding, endometriosis, persistent hyperplastic vitreous syndrome, ovarian cysts, carvenous hemangioma, synovitis, osteomyelitis, arthritis, and atherosclerosis, which are diseases characterized by excessive or abnormal neovascularization. In addition, the compounds, compositions and methods can be used in the prevention of hypercholesterolemia and cardiovascular disease associated with atherosclerosis. The compounds, compositions and methods of the present invention can also be used to treat dry macular degeneration (Houssier et al, PLOS Medicine, February 2008, Volume 5, Issue 2).

The treatment involves administration to a subject in need thereof a compound of the present invention or a pharmaceutically acceptable salt thereof, or a pharmaceutical composition comprising a pharmaceutical carrier and a therapeutically effective amount of a compound of the present invention, or a pharmaceutically acceptable salt thereof.

The compounds of the present invention, or their pharmaceutically acceptable salts or their prodrugs, may be administered in pure form or in an appropriate pharmaceutical composition, and can be carried out via any of the accepted modes of Galenic pharmaceutical practice.

The pharmaceutical compositions of the present invention can be prepared by mixing a compound of the present invention with at least one of an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral (subcutaneous injections, intravenous, intramuscular, intrasternal injection or infusion techniques), sublingual, ocular, rectal, vaginal, intranasal and intravitreal. Pharmaceutical compositions of the present invention are formulated so as to allow the active ingredients contained therein to be bioavailable upon administration of the composition to a subject. Compositions that will be administered to a subject or patient take the form of one or more dosage units, where for example, a tablet may be a single dosage unit, and a container of a compound of the present invention in aerosol form may hold a plurality of dosage units. Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the present invention, or a pharmaceutically acceptable salt thereof, for treatment of a disease-state as described above.

A pharmaceutical composition of the present invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example inhalatory administration.

For oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or oil such as soybean or vegetable oil.

The pharmaceutical composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the present invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediamine tetraacetic acid; buffers such as acetates, citrates or phosphates and agents for the adjustment of tonicity such as sodium chloride or dextrose. Solubilization agents may include cyclodextrins such as hydroxypropyl-beta-cyclodextrin. The parenteral preparation can be enclosed in ampoules, disposable syringes or multiple dose vials made of glass or plastic. An injectable pharmaceutical composition is preferably sterile.

A liquid pharmaceutical composition of the present invention used for either parenteral or oral administration should contain an amount of a compound of the present invention such that a suitable dosage will be obtained. Typically, this amount is at least 0.01% of a compound of the present invention in the composition. When intended for oral administration, this amount may be varied to be between 0.1 and about 70% of the weight of the composition. For parenteral usage, compositions and preparations according to the present invention are prepared so that a parenteral dosage unit contains between 0.01 to 1% by weight of the compound of the present invention.

The pharmaceutical composition of the present invention may be used for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the present invention from about 0.1 to about 10% w/v (weight per unit volume). Azapeptide administration by the nasal route is also applicable.

Furthermore, a solution of the azapeptide compound in sterile isotonic solution may be used for intravitreal injection. A carrier may also be used to transport the azapeptide compound through the sclera, using for example a biopolymer as the carrier.

The pharmaceutical composition of the present invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the present invention in solid or liquid form may include an agent that binds to the compound of the present invention and thereby assists in the delivery of the compound. Suitable agents that may act in this capacity include, but are not limited to, a monoclonal or polyclonal antibody, a protein or a liposome.

The pharmaceutical compositions of the present invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the present invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the present invention may be in a form suitable for ocular administration such as periocular injections or other methods for dispensing compounds and compositions in the eye. The compounds or compositions of the present invention could be administered in solutions, suspensions, in particulate drug delivery systems or in ocular implants, for example.

In particulate drug delivery systems, the compounds or compositions of the present invention can be incorporated in nanoparticles, microparticles, nanospheres, microspheres, nanocapsules and microcapsules (see for example, T Moritera et al. Invest. Opthalmol. Visual Sci 33-3125-3130 (1992); and J L Bourges et al. Invest Opthalmol. Visual science 44-3562-69 (2003)).

Intraocular drug delivery implants could also be used to deliver the compounds or compositions of the present invention, which may comprise non-biodegradable solid implants consisting of polyvinylalcohol-ethylene vinyl acetate or polysulfone capillary fiber, for example. These implants could be implanted in the posterior segment of the eye intravitreally or intrasclerally (see for example, Okabe K et al. Invest Opthalmol. Vis. Sci 44-2702-79 (2003)). Biodegradable solid implants of polylactic acid, poly glycolic acid, poly lactic-co-glycolic acid, polycaprolactones or polyanhydrides could also be used (see for example, Yasukawa T et al. Adv Drug Deliv Rev. 57: 2033-46 (2005)).

The compounds and compositions of the present invention could also be incorporated in viscous and injectable poly ortho esters derivatives for intraocular administration (see for example, Einmahl S et al. J. Biomed Mater Res. 50: 566-73 (2000); Einmahl S et al. Invest Opthalmol Vis Sci. 43: 1533-9 (2002)).

Liposomes, which belong to the family of microparticulate systems, can also be used as ocular delivery systems or as a microparticulate carrier system for the compounds and compositions of the present invention (see for example, Ebrahim S. et al. Sury Opthalmol. 50: 167-82 (2005); and Bejjani R A et al. J Fr Opthalmol. 26:981-5 (2003)).

The pharmaceutical compositions of the present invention may be prepared by methodology well known in the pharmaceutical art. For example, a pharmaceutical composition intended for administeration by injection can be prepared by admixing a compound of the present invention with sterile, distilled water so as to form a solution. A surfactant may be added to facilitate the formation of a homogeneous solution or suspension. Surfactants are compounds that non-covalently interact with the compound of the present invention so as to facilitate dissolution or homogeneous suspension of the compound in the aqueous delivery system.

The compounds of the present invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

III: Screening assays

The compounds of the present invention may also be used in a method to screen for other compounds that bind to a CD36 binding domain. Generally speaking, to use the compounds of the invention in a method of identifying compounds that bind to a CD36 binding domain, the CD36 is bound to a support, and a compound of the invention is added to the assay. Alternatively, the compound of the invention may be bound to the support and the CD36 is added.

There are a number of ways in which to determine the binding of a compound of the present invention to the CD36 binding domain. In one way, the compound of the invention, for example, may be fluorescently or radioactively labeled and binding determined directly. For example, this may be done by attaching the CD36 to a solid support, adding a detectably labeled compound of the invention, washing off excess reagent, and determining whether the amount of the detectable label is that present on the solid support. Numerous blocking and washing steps may be used, which are known to those skilled in the art.

In another example, a gene reporter assay for the screening of CD36 ligands is contemplated. The activation of CD36 induces the phosphorylation of src kinases (Fynn. Lynn kinases), and therefore a gene luciferase reporter assay would be particularly well suited to screen CD36 ligands.

The compounds of the invention may also be used as competitors to screen for additional drug candidates or test compounds. As used herein, the terms "drug candidate" or "test compounds" are used interchangeably and describe any molecule, for example, protein, oligopeptide, small organic molecule, polysaccharide, polynucleotide, and the like, to be tested for bioactivity. The compounds may be capable of directly or indirectly altering the CD36 biological activity.

Drug candidates can include various chemical classes, although typically they are small organic molecules having a molecular weight of more than 100 and less than about 2,500 Daltons. Candidate agents typically include functional groups necessary for structural interaction with proteins, for example, hydrogen bonding and lipophilic binding, and typically include at least an amine, carbonyl, hydroxyl, ether, or carboxyl group. The drug candidates often include cyclical carbon or heterocyclic structures and/or aromatic or polyaromatic structures substituted with one or more functional groups.

Drug candidates can be obtained from any number of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

Competitive screening assays may be done by combining a CD36 binding domain and a probe to form a probe:CD36 binding domain complex in a first sample followed by adding a test compound from a second sample. The binding of the test is determined, and a change, or difference in binding between the two samples indicates the presence of a test compound capable of binding to the CD36 binding domain and potentially modulating the CD36's activity.

In one case, the binding of the test compound is determined through the use of competitive binding assays. In this embodiment, the probe is labeled with an affinity label such as biotin. Under certain circumstances, there may be competitive binding between the test compound and the probe, with the probe displacing the candidate agent.

In one case, the test compound may be labeled. Either the test compound, or a compound of the present invention, or both, is added first to the CD36 binding domain for a time sufficient to allow binding to form a complex.

Formation of the probe: CD36 binding domain complex typically require incubations of between 4° C. and 40° C. for between 10 minutes to about 1 hour to allow for high-throughput screening. Any excess of reagents are generally removed or washed away. The test compound is then added, and the presence or absence of the labeled component is followed, to indicate binding to the CD36 binding domain.

In one case, the probe is added first, followed by the test compound. Displacement of the probe is an indication the test compound is binding to the CD36 binding domain and thus is capable of binding to, and potentially modulating, the activity of the CD36. Either component can be labeled. For example, the presence of probe in the wash solution indicates displacement by the test compound. Alternatively, if the test compound is labeled, the presence of the probe on the support indicates displacement.

In one case, the test compound may be added first, with incubation and washing, followed by the probe. The absence of binding by the probe may indicate the test compound is bound to the CD36 binding domain with a higher affinity. Thus, if the probe is detected on the support, coupled with a lack of test compound binding, may indicate the test compound is capable of binding to the CD36 binding domain.

Modulation is tested by screening for a test compound's ability to modulate the activity of CD36 and includes combining a test compound with a CD36 binding domain, as described above, and determining an alteration in the biological activity of the CD36. Therefore in this case, the test compound should both bind to the CD36 binding domain (although this may not be necessary), and alter its biological activity as defined herein.

Positive controls and negative controls may be used in the assays. All control and test samples are performed multiple times to obtain statistically significant results. Following incubation, all samples are washed free of non-specifically bound material and the amount of bound probe determined. For example, where a radiolabel is employed, the samples may be counted in a scintillation counter to determine the amount of bound compound.

Typically, the signals that are detected in the assay may include fluorescence, resonance energy transfer, time resolved fluorescence, radioactivity, fluorescence polarization, plasma resonance, or chemiluminescence and the like, depending on the nature of the label. Detectable labels useful in performing screening assays in this invention include a fluorescent label such as Fluorescein, Oregon green, dansyl, rhodamine, tetramethyl rhodamine, texas red, $Eu^{3+}$; a chemiluminescent label such as luciferase; colorimetric labels; enzymatic markers; or radioisotopes such as tritium, $I^{125}$ and the like.

Affinity tags, which may be useful in performing the screening assays of the present invention include biotin, polyhistidine and the like.

Additionally, the use of detectably labeled azapeptide compounds of the present invention is contemplated in a method for detecting the presence or absence of CD36 in a biological sample, such as for example, a sample that includes macrophages, endothelial cells or cardiomyocytes. To achieve this, the sample would be contacted, either in vivo or in vitro, with the labeled compound. A signal from the labeled compound bound to the CD36 would be measured, indicating the presence of CD36 in the sample.

Synthesis and Conformational Analysis of Azapeptide Analogs of GHRP-6

For the analysis of the conformational and structural requirements for affinity and activity at the GHS-R1a and CD36 receptors, azapeptide analogs were synthesized according to published methods (39, 40) using Fmoc-protected aza-amino acid chlorides to acylate the peptide chain. Removal of the Fmoc group and subsequent coupling of the next amino acid, typically by way of the Fmoc-amino acid chloride, embedded selectively the aza-amino acid residue within the peptide chain.

Analogues such as those presented in entries 12-70 of Table 1, have provided information concerning the active pharmacophore because aza-amino acid residues have been observed to stabilize turn conformations in model peptides (41). Moreover, these leads possess interesting potential to exhibit enhanced durations of action, because azapeptides have previously exhibited resistance to enzymatic degradation by proteases.

The replacement of Trp4 with azaPhe and with azaTyr improved selectivity by reducing affinity for the GHS-R1a and maintaining potency for the CD36 receptor. Peptide activity was similarly influenced on exchange of Trp4 for other aza-aromatic residues (azaBip, azaNal and azahomoPhe), albeit with >10 fold reduction in potency at the CD36 receptor. Removal of the aromatic moiety by exchange of Trp4 for aliphatic aza-amino acid residues (azaCha and azaLeu) diminished activity at both receptors. The conformational bias of the aza-residue seems necessary for favoring such aromatic interactions, because replacement of Trp4 by L- or D-Tyr dropped potency by ten-fold at the CD36 receptor. The loss in activity at GHS-R1a on replacing Trp4 with azaPhe is also consistent with earlier studies that have suggested the indole NH of Trp4 may be implicated in receptor binding of GHRP-6.

Replacement of D-Trp2 with aza-Tyr led to an analog with retained potency at the CD36 receptor. Similarly, swapping D-Trp2 for azaPhe, azaBip and for homo-azaPhe, all caused around a ten-fold drop at the CD36 receptor, and exchange of D-Trp2 for azaNal and for azaCha led to >10 fold loss of potency at the CD36 receptor.

Replacement of Ala3 by azaGly and azaLeu has provided DBG188p, DBG201-A, CP-2B (i), CP-2B (ii), CP-2B (iii), and CP-2B (v), which retained significant activity similar to the parent peptide. Moreover, in preliminary data on ex vivo inhibition of neovascularization, the azaLeu3 analog DBG201-A exhibited the most potent inhibitory effect in aortic rings, better than GHRP-6.

Relatively, high activities for the azaTyr2, azaGly3, azaLeu3 and azaPhe4 analogs, all lead to the hypothesis that there are two significant pharmacophores at the ends of the peptide chain, which are oriented by the curvature of the chain. A turn centered at the D-Trp-Ala-Trp sequence is likely to be important for activity at CD36, in light of the facts that an aza-scan across this region has led to a series of active candidates.

Peptides (compound numbers 32-33) and aza-peptides (compound numbers 12-31 and 33-38) were prepared on solid support using an acid labile Rink resin (42) and a Fmoc/tBu protocol (43). Incorporation of aza-amino acid into peptide was performed using either 1,3,4-oxadiazol-2(3H)-one for aza-Gly residue (44) or suitable N'-alkyl fluoren-9-ylmethyl carbazates to provide the corresponding Fmoc-aza amino acid chloride for coupling onto the growing chain of the resin-bound peptide (39, 41).

Synthesis of compound numbers 12-38 and 66-68

Rink resin (0.65 mmol/g) was purchased from Advanced Chemtech Inc. and the manufacturer's reported loading of the resin was used in the calculation of the yields of the final products. 20% Phosgene in toluene was purchased from Fluka. Melting points were uncorrected. $^1H$ and $^{13}C$ NMR spectra were recorded respectively at 400 MHz and 100 MHz in $CDCl_3$ or DMSO as the solvent and internal reference.

Thin-layer chromatography was performed on silica gel 60 $F_{254}$ plates from Merck. Flash chromatography was performed on silica gel 60 (230-400 Mesh ASTM) from Merck. Analytical HPLC analyses were performed on a TARGA column from Higgins Analytical, Inc. (4.6×250 mm, 5 μm, $C_{18}$) with a flow rate of 1.5 mL/min using a 40 min linear gradient from water (0.1% TFA) to $CH_3CN$ (0.1% TFA) (method 1) or MeOH (method 2). Retention times ($Tr_1$ and $Tr_2$) from analytical RP-HPLC are reported in minutes ($Tr_1$ for method 1, $Tr_2$ for method 2). Peptides and aza-petides were purified using semi-preparative LC-MS (Previal C18 column, 22×250 mm², particle size 5 μm) with solvent A, $H_2O$ (0.1% TFA), and solvent B, acetonitrile (0.1% TFA) using a gradient of 20-40% of A over 20 min at a flow rate of 15 mL/min.

9-H-Fluoren-9-ylmethyl carbazate (1)

To a well-stirred solution of hydrazine hydrate (19 g, 386 mmol) in 150 mL of $CH_3CN/H_2O$ (1/1, v/v), a solution of FmocCl (10 g, 38.65 mmol) in 600 mL $CH_3CN$ was added dropwise at 0° C. over 2 h. The reaction mixture was then allowed to warm to room temperature and stirred for an additional 12 hours, concentrated in vacuo to 150 mL and filtered to yield the title compound as a white solid, which was washed with water and hexane and dried to a constant weight in vacuo (9.74 g, 99%): mp 172-173° C.; $^1H$ NMR (DMSO) δ 4.08 (brs, 2H), 4.21 (t, J=7.2 Hz, 1H), 4.28 (d, J=7.2 Hz, 2H), 7.32 (t, J=7.4 Hz, 2H), 7.42 (t, J=7.4 Hz, 2H), 7.69 (d, J=7.4 Hz, 2H), 7.89 (d, J=7.4 Hz, 2H), 8.36 (brs, 1H); $^{13}C$ NMR (DMSO) δ 47.7, 66.7, 121.1 (2C), 126.3 (2C), 128.1 (2C), 128.7 (2C), 141.7 (2C), 144.9 (2C), 159.2.

General Procedure A for the Synthesis of N'-Alkyl Fluorenylmethyl Carbazates, 2-6

A suspension of 9-H-fluoren-9-ylmethyl carbazate 1 in EtOH (0.2 M) was treated with 100 mol % of suitable aldehyde, heated at reflux for 2 h and concentrated in vacuo. The hydrazone was dissolved in THF (0.2 M) and treated successively with 110 mol % of AcOH and 110 mol % of $NaBH_3CN$, stirred for 1 h and treated with additional $NaBH_3CN$ if necessary until completion of the reaction was observed by TLC. The mixture was concentrated in vacuo. The residue was dissolved in EtOAc, washed with aqueous $KHSO_4$ (1M) and brine, dried over $Na_2SO_4$ and concentrated under reduced pressure to yield a white solid, that was dissolved in EtOH and heated at reflux for 1 h. The mixture was concentrated under reduced pressure to yield a residue that was isolated by flash chromatography to yield the carbazate (2-6).

N'-Methyl-fluorenylmethyl carbazate (2)

Product from the reaction of carbazate 1 (7.1 mmol) and formaldehyde (7.1 mmol) was isolated in 77% yield by flash chromatography using a 30% EtOAc in hexane eluant as a white solid: Rf=0.54 (40% EtOAc in hexanes); mp 155-156° C.; $^1H$ NMR (DMSO) δ 2.43 (s, 3H), 4.22 (t, J=6.8 Hz, 1H), 4.31 (d, J=6.8 Hz, 2H), 4.46 (brs, 1H), 7.32 (t, J=7.4 Hz, 2H), 7.41 (t, J=7.4 Hz, 2H), 7.69 (d, J=7.4 Hz, 2H), 7.88 (d, J=7.4 Hz, 2H), 8.67 (brs, 1H); $^{13}C$ NMR (DMSO) δ 39.3, 47.7, 66.4, 121.1 (2C), 126.2 (2C), 128.1 (2C), 128.7 (2C), 141.8 (2C), 144.9 (2C), 157.8. LRMS (EI) 179.2 (M+H−100)+, 268.9 (M+H)+, 291.7 (M+Na)+; HRMS (EI) m/e for $C_{16}H_{17}N_2O_2$ (M+H)+, calcd 269.1285. Found 269.1291.

N'-Isopropyl-fluorenylmethyl carbazate (3)

Product from the reaction of carbazate 1 (3.9 mmol) and acetone (39 mmol) was isolated in 68% yield by flash chromatography using a 30% EtOAc in hexane eluant as a white solid: Rf=0.20 (30% EtOAc in hexanes); mp 163-164° C.; $^1H$ NMR (DMSO) δ 0.91 (d, J=5.9 Hz, 6H), 2.51 (t, J=6.0 Hz, 1H), 4.22 (t, J=6.6 Hz, 1H), 4.31 (d, J=6.6 Hz, 2H), 4.36 (brs, 1H), 7.32 (t, J=7.4 Hz, 2H), 7.41 (t, J=7.4 Hz, 2H), 7.71 (d, J=7.4 Hz, 2H), 7.89 (d, J=7.4 Hz, 2H), 8.68 (brs, 1H); $^{13}C$ NMR (DMSO) δ 21.5 (2C), 47.6, 50.3, 66.3, 121.0 (2C), 126.1 (2C), 127.9 (2C), 128.5 (2C), 141.6 (2C), 144.7 (2C), 157.8. LRMS (EI) 296.9 (M+H)+. HRMS (EI) m/e for $C_{18}H_{21}N_2O_2$ (M+H)+, calcd 297.1598. Found 297.1599.

N'-2-Isobutyl-fluorenylmethyl carbazate (4)

Product from the reaction of carbazate 1 (3.6 mmol) and 2-methylpropanal (3.6 mmol) was isolated in 72% yield by flash chromatography using a 20% EtOAc in hexane eluant as a white solid: Rf=0.30 (20% EtOAc in hexanes); mp 124-125° C.; $^1H$ NMR (DMSO) δ 0.87 (d, J=4.0 Hz, 6H), 1.63 (brs, 1H), 2.50 (brs, 2H), 4.22 (t, J=6.3 Hz, 1H), 4.29 (d, J=6.3 Hz, 2H), 4.49 (brs, 1H), 7.32 (t, J=7.4 Hz, 2H), 7.40 (t, J=7.4 Hz, 2H), 7.68 (d, J=7.4 Hz, 2H), 7.88 (d, J=7.4 Hz, 2H), 8.66 (brs, 1H); $^{13}C$ NMR (DMSO) δ 21.5 (2C), 27.1, 47.6, 59.6, 66.2, 121.0 (2C), 126.1 (2C), 127.9 (2C), 128.5 (2C), 141.6 (2C), 144.7 (2C), 157.7. LRMS (EI) 310.9 (M+H)+. HRMS (EI) m/e for $C_{19}H_{23}N_2O_2$ (M+H)+, calcd 311.1754. Found 311.1761.

N'-cyclohexylmethyl-fluorenylmethyl carbazate (5)

Product from the reaction of carbazate 1 (2.5 mmol) and cyclohexanone (2.5 mmol) was isolated in 76% yield by flash chromatography using 50% EtOAc in hexane as eluant: white foam; Rf=0.26 (50% EtOAc in hexanes); $^1H$ NMR (DMSO) δ 0.84 (q, J=11.2 Hz, 2H), 1.04-1.25 (m, 3H), 1.37 (m, 1H), 1.54-1.70 (m, 3H), 1.75 (d, J=12.8 Hz, 2H), 2.53 (m, 2H), 4.22 (t, J=6.8 Hz, 1H), 4.30 (d, J=6.8 Hz, 2H), 4.45 (m, 1H), 7.32 (t, J=8.4 Hz, 2H), 7.42 (t, J=7.6 Hz, 2H), 7.70 (d, J=7.6 Hz, 2H), 7.89 (d, J=7.2 Hz, 2H), 8.67 (m, 1H); $^{13}C$ NMR (DMSO) δ 25.7 (2C), 26.4 (2C), 31.0, 35.8, 46.8, 57.5, 65.5, 120.2 (2C), 125.3 (2C), 127.1 (2C), 127.7 (2C), 140.8 (2C), 143.9 (2C), 156.9. LRMS (EI) 351.1 (M+H)+. HRMS (EI) m/e for $C_{22}H_{27}N_2O_2$ (M+H)+, calcd 396.1918. Found 396.1919.

N'-2-phenylethyl-fluorenylmethyl carbazate (6)

Product from the reaction of carbazate 1 (2.5 mmol) and phenylacetaldehyde (2.5 mmol) was isolated in 76% yield by flash chromatography using 50% EtOAc in hexane as eluant: white foam; Rf=0.26 (50% EtOAc in hexanes); $^1H$ NMR (DMSO) δ 2.67 (t, J=7.2 Hz, 2H), 2.94 (m, 2H), 4.24 (t, J=6.8 Hz, 1H), 4.34 (d, J=6.8 Hz, 2H), 4.63 (m, 1H), 7.14-7.36 (m, 7H), 7.42 (t, J=7.6 Hz, 2H), 7.71 (d, J=7.2 Hz, 2H), 7.90 (d, J=7.6 Hz, 2H), 8.78 (brs, 1H); $^{13}C$ NMR (DMSO) δ 33.9, 46.8, 52.5, 65.6, 120.2 (2C), 125.3 (2C), 125.9, 127.2 (2C), 127.8 (2C), 128.3 (2C), 128.8 (2C), 140.2, 140.8 (2C), 143.9 (2C), 157.0. LRMS (EI) 359.1 (M+H)+, 381.2 (M+Na)+. HRMS (EI) m/e for $C_{23}H_{23}N_2O_2$ (M+H)+, calcd 396.1918. Found 396.1919.

General Procedure B for the Synthesis of N'-Alkyl Fluorenylmethyl Carbazates (7-11)

A suspension of 9-H-fluoren-9-ylmethyl carbazate 1 in EtOH (0.2 M) was treated with 100 mol % of suitable aldehyde heated at reflux for 2 h, let cool and concentrated in vacuo. The hydrazone was dissolved in THF (0.2 M), treated with a suspension of 10 mol % of $Pd(OH)_2$ on carbon (20 wt %) in THF, placed under $H_2$ gas at 100 psi and stirred at room temperature overnight. The reaction mixture was filtered over Celite. The filtrate was evaporated on a rotary evaporator. The N'-alkyl fluorenylmethyl carbazate, 7-11 was isolated by flash chromatography.

N'-Benzyl-fluorenylmethyl carbazate (7)

Product from the reaction of carbazate 1 (7.8 mmol) and benzaldehyde (7.8 mmol) was isolated as a white solid in 94% yield by flash chromatography using a 30% EtOAc in hexane eluant: Rf=0.27 (30% EtOAc in hexanes); mp 143-145° C.; $^1$H NMR (DMSO) δ 3.88 (brs, 2H), 4.21 (t, J=6.8 Hz, 1H), 4.31 (d, J=6.8 Hz, 2H), 4.95 (brs, 1H), 7.15-7.35 (m, 7H), 7.41 (t, J=7.4 Hz, 2H), 7.67 (d, J=7.6 Hz, 2H), 7.89 (d, J=7.6 Hz, 2H), 8.71 (brs, 1H); $^{13}$C NMR (DMSO) δ 47.7, 55.2, 66.4, 121.1 (2C), 126.3 (2C), 127.9, 128.1 (2C), 128.7 (2C), 129.1 (2C), 129.5 (2C), 139.8, 141.8 (2C), 144.8 (2C), 157.9. LRMS (EI) 344.9 (M+H)$^+$, 688.9 (2M+H)$^+$. HRMS (EI) m/e for $C_{22}H_{21}N_2O_2$ (M+H)$^+$, calcd 345.1598. Found 345.1603.

N'-(4-(tert-Butyldimethylsilyloxy))-benzyl)-fluorenylmethyl carbazate (8)

Product from the reaction of carbazate 1 (5.90 mmol) and 4-(tert-Butyldimethylsilyloxy))-benzaldehyde (5.90 mmol) was isolated in 70% yield as a colorless oil by flash chromatography using a 20% EtOAc in hexane eluant: Rf=0.30 (20% EtOAc in hexanes); $^1$H NMR (DMSO) δ 0.18 (s, 6H), 0.93 (s, 9H), 3.80 (brs, 2H), 4.20 (t, J=6.5 Hz, 1H), 4.29 (d, J=6.5 Hz, 2H), 4.83 (brs, 1H), 6.77 (d, J=8.3 Hz, 2H), 7.18 (d, J=8.0 Hz, 2H), 7.31 (t, J=7.5 Hz, 2H), 7.41 (t, J=7.5 Hz, 2H), 7.67 (d, J=7.4 Hz, 2H), 7.88 (d, J=7.5 Hz, 2H), 8.69 (brs, 1H); $^{13}$C NMR (DMSO) δ-3.5 (2C), 19.0, 26.6 (3C), 47.7, 54.8, 66.5, 120.4 (2C), 121.1 (2C), 126.3 (2C), 128.1 (2C), 128.7 (2C), 130.8 (2C), 132.4, 141.8 (2C), 144.8 (2C), 155.0, 157.9. HRMS (EI) m/e for $C_{28}H_{35}N_2O_3Si$ (M+H)$^+$, calcd 475.2412. Found 475.2414.

N'-(1-naphthylmethyl)-fluorenylmethyl carbazate (9)

Product from the reaction of carbazate 1 and 1-naphthylaldehyde was isolated as a white solid in 25% yield by flash chromatography using 30% EtOAc in hexane as eluant Rf=0.50 (40% EtOAc in hexanes); mp 136-137° C.; $^1$H NMR (CDCl$_3$) δ 4.27 (t, J=6.7 Hz, 1H), 4.51 (m, 4H), 6.43 (bs, 1H), 7.30-7.39 (m, 2H), 7.40-7.49 (m, 4H), 7.50-7.70 (m, 4H), 7.75-7.96 (m, 4H), 8.31 (d, J=8.4 Hz, 1H); $^{13}$C NMR (CDCl$_3$) δ 46.9, 53.1, 66.7, 119.7 (2C), 123.6, 124.7 (2C), 125.0, 125.5, 126.1, 126.8 (2C), 127.5 (2C), 127.6, 128.2, 128.3, 131.7, 132.4, 133.5, 141.0 (2C), 143.3 (2C), 156.9. LRMS (EI) 395.1 (M+H)$^+$, 789.1 (2M+H)$^+$. HRMS (EI) m/z for $C_{26}H_{23}N_2O_2$ (M+H)$^+$, calcd 395.1754. Found 345.1755.

N'-(2-naphthylmethyl)-fluorenylmethyl carbazate (10)

Product from the reaction of carbazate 1 and 2-naphthylaldehyde was isolated as a white solid in 50% yield by flash chromatography using 30% EtOAc in hexane as eluant: Rf=0.56 (40% EtOAc in hexanes); mp 128-129° C.; $^1$H NMR (CDCl$_3$) δ 4.20 (m, 2H), 4.25 (t, J=6.8 Hz, 1H), 4.49 (m, 2H), 6.45 (bs, 1H), 7.29-7.38 (m, 2H), 7.44 (t, J=7.4 Hz, 2H), 7.48-7.55 (m, 3H), 7.57-7.63 (m, 2H), 7.77-7.81 (m, 2H), 7.82-7.91 (m, 3H); $^{13}$C NMR (CDCl$_3$) δ 46.8, 55.4, 66.7, 119.7 (2C), 124.7 (2C), 125.6, 125.8, 126.6, 126.8 (2C), 127.4, 127.5 (2C), 127.5 (2C), 127.9, 132.6, 133.0, 134.5, 141.0 (2C), 143.3 (2C), 156.9. LRMS (EI) 395.1 (M+H)$^+$, 789.1 (2M+H)$^+$. HRMS (EI) m/z for $C_{26}H_{23}N_2O_2$ (M+H)$^+$, calcd 395.1754. Found 345.1755.

N'-(biphenyl-4-ylmethyl)-fluorenylmethyl carbazate (11)

Product from the reaction of carbazate 1 and 4-biphenylaldehyde was isolated as a white solid in 58% yield by flash chromatography using 30% EtOAc in hexane as eluant: Rf=0.35 (40% EtOAc in hexanes); mp 140-141° C.; $^1$H NMR (CDCl$_3$) δ 4.09 (m, 2H), 4.27 (m, 1H), 4.51 (m, 2H), 6.44 (bs, 1H), 7.30-7.52 (m, 9H), 7.55-7.68 (m, 6H), 7.80 (d, J=7.5 Hz, 2H) $^{13}$C NMR (CDCl$_3$) δ 46.5, 55.0, 66.6, 119.7 (2C), 124.7 (2C), 126.8 (4C), 126.9 (2C), 127.0, 127.5 (2C), 128.5 (2C), 129.1 (2C), 136.0, 140.2, 140.4, 141.0 (2C), 143.3 (2C), 156.8. LRMS (EI) 421.1 (M+H)$^+$. HRMS (EI) m/z for $C_{28}H_{25}N_2O_2$ (M+H)$^+$, calcd 421.1910. Found 421.1910.

General Procedure for Fmoc Deprotection and HBTU Couplings

Peptide synthesis was performed under standard condition in an automated shaker using Rink resin. Couplings of amino-acids (3 eq) were performed in DMF using HBTU (3 eq) as coupling reagent and DIEA (3 eq and 1 eq 20 min after the start of the coupling reaction) as base. Fmoc deprotections were performed by treating resin with 20% piperidine in DMF for periods of 10 min and 20 min. Resin was washed after each coupling and deprotection step alternatively with DMF (2×), MeOH (2×) and DCM (2×).

General Procedure for Introduction of Aza-Amino Acid on Resin and Coupling of the Next Amino Acid To a 0.1M solution of a suitable N'-alkyl fluoren-9-ylmethyl carbazate (2-11) (300 mol % relative to resin loading) in dry DCM under argon at 0° C., a solution of phosgene in toluene (20% by wt, 600 mol %) was added dropwise. After complete consumption of starting material (2-11) (usually after 15 min as indicated by TLC), the reaction mixture was concentrated in vacuo to yield the Fmoc-aza-amino acid chloride which was employed without further purification. The resulting Fmoc-aza-amino acid chloride (300 mol %) was suspended in dry DCM (0.15 M), treated with DIEA (600 mol %) to obtain a clear solution, and transferred to a vessel containing the resin-bound N-terminal amine swollen in dry DCM. The mixture was shaken overnight at room temperature under argon. The solution was filtered, the resin was washed twice with dry DCM and the aza-amino acid coupling procedure described above was repeated again. The resin was then treated under the conditions to remove the Fmoc group that were described above. The aza-amino acid resin was then swollen in dry THF and treated with a solution of Fmoc-amino acid (300 mol %) in THF (0.15 M), followed sequentially by BTC (100 mol %) and 2,4,6-collidine (1400 mol %). The reaction mixture was shaken for 3 h under argon and the resin was filtered. The resin was washed alternatively with DMF (2×), MeOH (2 x) and DCM (2×) and peptide synthesis was continued.

General Procedure for Side-Chain Deprotection and Aza-Peptide Cleavage

Aza-peptide resin was treated with a freshly made solution of TFA/H$_2$O/TIS (95/2.5/2.5, v/v/v, 20 mL/g aza-peptide resin) for 2 h at room temperature. The cleavage mixture was filtered and the resin was washed with neat TFA. The filtrate was then concentrated to about 1 mL and treated with Et$_2$O. The resulting aza-peptide precipitate was filtered, washed with Et$_2$O and dissolved in an acetonitrile/H$_2$O (1/1, v/v) solution and lyophilized to yield a light foam or powder.

His-D-Trp-azaAla-Trp-D-Phe-Lys-NH$_2$ (12) Tr$_1$=14.85, Tr$_2$=22.03; LRMS (EI) calcd for $C_{45}H_{56}N_{13}O_6$ (M+H)$^+$, 874.4. Found m/e 874.3 (M+H)$^+$. CH$_3$(CH$_2$)$_4$CO-D-Trp-azaAla-D-Phe-Lys-NH$_2$ (13) Tr$_1$=22.80, Tr$_2$=N.D.; LRMS (EI) calcd for C$_{45}$H$_{59}$N$_{10}$O$_6$ (M+H)$^+$, 835.5. Found m/e 835.4 (M+H)$^+$. (CH$_3$)$_2$CHCH$_2$CO-D-Trp-azaAla-D-Phe-Lys-NH$_2$ (14) Tr$_1$=21.60, Tr$_2$=N.D.; LRMS (EI) calcd for C$_{43}$H$_{55}$N$_{10}$O$_6$ (M+H)$^+$, 821.4. Found m/e 821.4 (M+H)$^+$. Ph-(CH$_2$)$_2$—CO-D-Trp-azaAla-Trp-D-Phe-Lys-NH$_2$ (15) Tr$_1$=22.77, Tr$_2$=N.D.; LRMS (EI) calcd for C$_{48}$H$_{57}$N$_{10}$O$_6$ (M+H)$^+$, 869.4. Found m/e 869.4 (M+H)$^+$. CH$_3$CH(OH)—CO-D-Trp-azaAla-Trp-D-Phe-Lys-NH$_2$ (16) Tr$_1$=19.15, Tr$_2$=N.D.; LRMS (EI) calcd for C$_{42}$H$_{53}$N$_{10}$O$_7$ (M+H)$^+$, 809.4. Found m/e 809.4 (M+H)$^+$. Ph-CO-D-Trp-azaAla-Trp-D-Phe-Lys-NH$_2$ (17) Tr$_1$=21.87, Tr$_2$=N.D.; LRMS (EI) calcd for C$_{46}$H$_{53}$N$_{10}$O$_6$ (M+H)$^+$, 841.4. Found m/e 841.4 (M+H)$^+$. Nal-1-CO-D-Trp-azaAla-Trp-D-Phe-Lys-NH$_2$ (18) Tr$_1$=23.71, Tr$_2$=N.D.; LRMS (EI) calcd for C$_{50}$H$_{55}$N$_{10}$O$_6$ (M+H)$^+$, 891.4. Found m/e 891.4 (M+H)$^+$. Cy-CO-D-Trp-azaAla-Trp-D-Phe-Lys-NH$_2$ (19) Tr$_1$=22.72, Tr$_2$=N.D.; LRMS (EI) calcd for C$_{46}$H$_{59}$N$_{10}$O$_6$ (M+H)$^+$, 847.5. Found m/e 847.4 (M+H)$^+$. In—CO-D-Trp-azaAla-Trp-D-Phe-Lys-NH$_2$ (20) Tr$_1$=18.35/18.85, Tr$_2$=N.D.; LRMS (EI) calcd for C$_{49}$H$_{58}$N$_{11}$O$_6$ (M+H)$^+$, 896.5. Found m/e 896.4 (M+H)$^+$. Ph-CH$_2$—CH(OH)—CO-D-Trp-azaAla-Trp-D-Phe-Lys-NH$_2$ (21) Tr$_1$=21.65, Tr$_2$=N.D.; LRMS (EI) calcd for C$_{48}$H$_{57}$N$_{10}$O$_7$ (M+H)$^+$, 885.4. Found m/e 885.4 (M+H)$^+$. His-azaTyr-Ala-Trp-D-Phe-Lys-NH$_2$ (22) Tr$_1$=13.41, Tr$_2$=20.21; LRMS (EI) calcd for C$_{43}$H$_{55}$N$_{12}$O$_7$ (M+H)$^+$, 851.4. Found m/e 851.3 (M+H)$^+$. His-D-Trp-Ala-azaTyr-D-Phe-Lys-NH$_2$ (23) Tr$_1$=13.57, Tr$_2$=20.59; LRMS (EI) calcd for C$_{43}$H$_{55}$N$_{12}$O$_7$ (M+H)$^+$, 851.4. Found m/e 851.3 (M+H)$^+$. His-D-Trp-azaGly-Trp-D-Phe-Lys-NH$_2$ (24) Tr$_1$=14.48, Tr$_2$=21.84; LRMS (EI) calcd for C$_{44}$H$_{54}$N$_{13}$O$_6$ (M+H)$^+$, 860.4. Found m/e 860.3 (M+H)$^+$. His-D-Trp-azaLeu-Trp-D-Phe-Lys-NH$_2$ (25) Tr$_1$=16.24, Tr$_2$=25.33; LRMS (EI) calcd for C$_{48}$H$_{62}$N$_{13}$O$_6$ (M+H)$^+$, 916.5. Found m/e 916.5 (M+H)$^+$. His-D-Trp-Ala-azaPhe-D-Phe-Lys-NH$_2$ (26) Tr$_1$=14.96, Tr$_2$=23.87; LRMS (EI) calcd for C$_{43}$H$_{55}$N$_{12}$O$_6$ (M+H)$^+$, 835.4. Found m/e 835.5 (M+H)$^+$. His-D-Trp-Ala-azaLeu-D-Phe-Lys-NH$_2$ (27) Tr$_1$=14.27, Tr$_2$=22.83; LRMS (EI) calcd for C$_{40}$H$_{57}$N$_{12}$O$_6$ (M+H)$^+$, 801.4. Found m/e 801.5 (M+H)$^+$. His-D-Trp-Ala-azaBip-D-Phe-Lys-NH$_2$ (28) Tr$_1$=17.81, Tr$_2$=27.68; LRMS (EI) calcd for C$_{49}$H$_{59}$N$_{12}$O$_6$ (M+H)$^+$, 911.5. Found m/e 911.5 (M+H)$^+$. His-D-Trp-Ala-azaCha-D-Phe-Lys-NH$_2$ (29) Tr$_1$=16.08, Tr$_2$=25.73; LRMS (EI) calcd for C$_{43}$H$_{61}$N$_{12}$O$_6$ (M+H)$^+$, 841.5. Found m/e 841.5 (M+H)$^+$. His-D-Trp-Ala-azahomoPhe-D-Phe-Lys-NH$_2$ (30) Tr$_1$=15.44, Tr$_2$=24.69; LRMS (EI) calcd for C$_{44}$H$_{57}$N$_{12}$O$_6$ (M+H)$^+$, 849.4. Found m/e 849.5 (M+H)$^+$. His-D-Trp-Ala-azaNal-1-D-Phe-Lys-NH$_2$ (31) Tr$_1$=16.53, Tr$_2$=26.08; LRMS (EI) calcd for C$_{47}$H$_{57}$N$_{12}$O$_6$ (M+H)$^+$, 885.4. Found m/e 885.5 (M+H)$^+$. His-D-Trp-Ala-Tyr-D-Phe-Lys-NH$_2$ (32) Tr$_1$=12.59, Tr$_2$=20.64; LRMS (EI) calcd for C$_{44}$H$_{56}$N$_{11}$O$_7$ (M+H)$^+$, 850.4. Found m/e 850.5 (M+H)$^+$. His-D-Trp-Ala-D-Tyr-D-Phe-Lys-NH$_2$ (33) Tr$_1$=13.17, Tr$_2$=20.99; LRMS (EI) calcd for C$_{44}$H$_{56}$N$_{11}$O$_7$ (M+H)$^+$, 850.4. Found m/e 850.5 (M+H)$^+$. His-azaPhe-Ala-Trp-D-Phe-Lys-NH$_2$ (34) Tr$_1$=14.08, Tr$_2$=22.64; LRMS (EI) calcd for C$_{43}$H$_{55}$N$_{12}$O$_6$ (M+H)$^+$, 835.4. Found m/e 835.5 (M+H)$^+$. His-azaNal-1-Ala-Trp-D-Phe-Lys-NH$_2$ (35) Tr$_1$=15.41, Tr$_2$=25.23; LRMS (EI) calcd for C$_{47}$H$_{57}$N$_{12}$O$_6$ (M+H)$^+$, 885.4. Found m/e 885.5 (M+H)$^+$. His-azahomoPhe-Ala-Trp-D-Phe-Lys-NH$_2$ (36) Tr$_1$=14.80, Tr$_2$=23.37; LRMS (EI) calcd for C$_{44}$H$_{57}$N$_{12}$O$_6$ (M+H)$^+$, 849.4. Found m/e 849.5 (M+H)$^+$. His-azaBip-Ala-Trp-D-Phe-Lys-NH$_2$ (37) Tr$_1$=16.88, Tr$_2$=26.80; LRMS (EI) calcd for C$_{49}$H$_{59}$N$_{12}$O$_6$ (M+H)$^+$, 911.5. Found m/e 911.5 (M+H)$^+$. His-azaCha-Ala-Trp-D-Phe-Lys-NH$_2$ (38) Tr$_1$=14.93, Tr$_2$=24.75; LRMS (EI) calcd for C$_{43}$H$_{61}$N$_{12}$O$_6$ (M+H)$^+$, 841.5. Found m/e 841.5 (M+H)$^+$. Phe-D-Trp-Ala-azaTyr-D-Phe-Lys-NH$_2$ (66) Tr$_1$ 5.30$^d$; LRMS (EI) calcd for C$_{46}$H$_{56}$N$_{10}$O$_7$ (M+H)$^+$, 861.4. Found m/e 861.3 (M+H)$^+$, 883.3 (M+23)$^+$, 431.3 (M+2H)$^+$. Ala-D-Trp-Ala-azaTyr-D-Phe-Lys-NH$_2$ (67) Tr$_1$ 4.82; LRMS (EI) calcd for C$_{40}$H$_{52}$N$_{10}$O$_7$(M+H)$^+$, 785.4. Found m/e 785.3 (M+H)$^+$, 807.2 (M+23)$^+$, 393.4 (M+2H)$^+$. Hydrocinnamyl-D-Trp-Ala-azaTyr-D-Phe-Lys-NH$_2$ (68) Tr$_1$=5.04$^e$; LRMS (EI) calcd for C$_{46}$H$_{55}$N$_9$O$_7$ (M+H)$^+$, 846.4. Found m/e 846.5 (M+H)$^+$, 868.4 (M+23).

Peptide Synthesis

Peptides were synthesized on Rink resin (0.65 mmol/g) under standard conditions (43) in an automated shaker. Couplings of Fmoc-amino acids (300 mol %) were performed in DMF using HBTU (300 mol %) as coupling reagent and DIEA (300 mol %) as base. Side-chains for Lys and D-Trp were protected by Boc group and H is with a trityl group. Fmoc deprotections were performed by treating resin with 20% piperidine in DMF for periods of 10 min and 20 min. Resin was washed after each coupling and deprotection step alternatively with DMF (2×), MeOH (2×) and DCM (2×). Side-chain deprotection and peptide cleavage were performed with a freshly made solution of TFA/H$_2$O/TIS (95/2.5/2.5, v/v/v, 20 mL/g peptide resin) for 2 h at room temperature. The cleavage mixture was filtered and the resin was washed with neat TFA. The filtrate was then concentrated and treated with chilled Et$_2$O to precipitate the peptides. The peptides were removed by centrifugation, dissolved in CH$_3$CN/H$_2$O (1/1, v/v) and lyophilized. The crude material was purified by semi-preparative RP-HPLC (Higgins C18 column, 20×250 mm, particle size 5 µm) with solvent A, H$_2$O (0.1% TFA) and solvent B, CH$_3$CN (0.1% TFA). Analytical HPLC condition I was performed on a Xterra MS C18 column (4.6×150 mm, particle size 5 µm) using a gradient of 0-65% eluant B in A over 20 min with a flow rate of 0.5 mL/min and the detector centered at 210 nm: B (CH$_3$CN) in A (H$_2$O containing 0.1% formic acid) and retention times (t$_R$) are reported in minutes. Analytical HPLC condition II was performed on a Xterra MS C18 column (4.6×150 mm, particle size 5 µm) using a gradient of 0-65% eluant B (MeOH) in A (H$_2$O containing 0.1% formic acid) over 20 min with a flow rate of 0.5 mL/min.

Synthesis of compound numbers 39-65

General Procedure for the Synthesis of N'-Alkyl-Fluorenylmethyl Carbazates

N'-2-Isobutyl-fluorenyl methyl carbazate, N'-benzyl-fluorenylmethyl carbazate, and N'-(4-(t-butyldimethylsilyloxy)-benzyl)-fluorenyl-methyl carbazate as azapeptide precursors were synthesized according to published procedure (39).

Fluoren-9-yl-methylpyrazolidine-1-carboxylate hydrochloride

Tert-butyl pyrazolidine-1-carboxylate (39) (1.39 g, 8.08 mmoles) was acylated with Fmoc succinimide (3.27 g, 9.69 mmoles, 1.2 eq.) in dry dichloromethane (20 mL). The reactive mixture was left stirring overnight. The volatiles were removed using a rotary evaporator and the residue was dissolved in EtOAc. The organic layer was extracted three times, respectively, with 5% citric acid, 5% NaHCO$_3$ and brine, dried over Na$_2$SO$_4$, filtered and concentrated to a white foam which was purified by column chromatography using 7:3 EtOAc:Hexane as eluant. Evaporation of the collected fractions afforded 1-(9H-fluoren-9-yl)methyl 2-tert-butyl pyrazolidine-1,2-dicarboxylate as a white solid in a 94% yield. Pyrazolidine-1,2-dicarboxylate (1.34 g, 3.4 mmoles) was treated with 25 mL of a 1:1 TFA:DCM solution and stirred for one hour. Removal of the volatiles by rotary evaporation gave a residue that was dissolved in 1N HCl, stirred for 1 hour and freeze-dryed to yield hydrochloride (9H-fluoren-9-yl)methyl-1-carboxylate: mp (143.2-148.1° C.), $^1$H NMR (DMSO) δ 7.89 (d, J=7.32 Hz, 2H), 7.72 (d, J=7.33 Hz, 2H), 7.43 (ddd, J=7.36 Hz, 0.57 Hz, 2H), 7.33 (ddd, J=7.42 Hz, 1.14 Hz, 2H), 4.44 (d, J=6.90 Hz, 2H), 4.33 (t, J=6.56 Hz, 1H), 3.58 (t, J=6.96 Hz, 2H), 3.43 (t, J=6.96 Hz, 2H), 2.20 (m, 2H). $^{13}$C (DMSO) δ 154.57, 144.64, 142.11, 129.26, 126.54, 121.67, 69.89, 47.50, 25.50.

Solid-Phase Azapeptide Synthesis

Incorporation of aza-amino acids on resin was performed according to literature procedure (39). To generate a library of 29 azapeptides in parallel, IRORI kan technology was employed. Macrokans were respectively filled with 130 mg (0.0845 mmole) of 75-100 mesh Rink Resin SS and a radiofrequency (Rf) tag associated to a unique ID number. In a split-and-mix approach, kans undergoing identical reactions were pooled together in a normal glass vessel, that was filled with solvent and reagents which difused through the outer mesh walls of the microreactors. Upon completion of the reaction, Macrokans were separated, sorted, and pooled accordingly for next reactions (39).

His-azaPhe-Ala-Trp-D-Phe-Ala-NH$_2$ (39) Tr$_1$=15.54, Tr$_2$=11.05; LRMS (EI) calcd for C$_{40}$H$_{47}$N$_{11}$O$_6$(M+H)$^+$, 778.4. Found m/e 778.4 (M+H)$^+$, 800.4 (M+23)$^+$. His-azaPhe-Ala-Trp-D-Ala-Lys-NH$_2$ (40) Tr$_1$=9.08, Tr$_2$=9.11; LRMS (EI) calcd for C$_{37}$H$_{50}$N$_{12}$O$_6$(M+H)$^+$, 759.4. Found m/e 759.4 (M+H)$^+$, 781.4 (M+23)$^+$. (D/L)His-azaPhe-Ala-Ala-D-Phe-Lys-NH$_2$ (41) Tr$_1$=9.99, Tr$_2$=11.93; LRMS (EI) calcd for C$_{35}$H$_{49}$N$_{11}$O$_6$ (M+H)$^+$, 720.4. Found m/e 720.4 (M+H)$^+$. Ala-azaPhe-Ala-Trp-D-Phe-Lys-NH$_2$ (42) Tr$_1$=15.67, Tr$_2$=7.80$^c$; LRMS (EI) calcd for C$_{40}$H$_{52}$N$_{10}$O$_6$ (M+H)$^+$, 769.4. Found m/e 769.4 (M+H)$^+$. His-azaTyr-Ala-Trp-D-Phe-Ala-NH$_2$ (43) Tr$_1$=14.89, Tr$_2$=21.34; LRMS (EI) calcd for C$_{40}$H$_{47}$N$_{11}$O$_7$ (M+H)$^+$, 794.4. Found m/e 794.4 (M+H)$^+$, 816.4 (M+23)$^+$. His-azaTyr-Ala-Trp-D-Ala-Lys-NH$_2$ (44) Tr$_1$=8.79, Tr$_2$=10.79; LRMS (EI) calcd for C$_{37}$H$_{50}$N$_{12}$O$_7$(M+H)$^+$, 775.4. Found m/e 775.4 (M+H)$^+$, 797.4 (M+23)$^+$. (D/L)His-azaTyr-Ala-Ala-D-Phe-Lys-NH$_2$ (45) Tr$_1$=8.13, Tr$_2$=8.18; LRMS (EI) calcd for C$_{35}$H$_{49}$N$_{11}$O$_7$ (M+H)$^+$, 736.4. Found m/e 736.4 (M+H)$^+$, 758.4 (M+23)$^+$. Ala-azaTyr-Ala-Trp-D-Phe-Lys-NH$_2$ (46) Tr$_1$=13.19, Tr$_2$=19.02; LRMS (EI) calcd for C$_{40}$H$_{52}$N$_{10}$O$_7$(M+H)$^+$, 785.4. Found m/e 785.4 (M+H)$^+$, 807.4 (M+23)$^+$. His-D-Trp-azaGly-Trp-D-Phe-Ala-NH$_2$ (47) Tr$_1$=11.01$^b$, Tr$_2$=18.56; LRMS (EI) calcd for C$_{41}$H$_{46}$N$_{12}$O$_6$ (M+H)$^+$, 803.4. Found m/e 803.4 (M+H)$^+$, 825.4 (M+23)$^+$. His-D-Trp-azaGly-Trp-D-Ala-Lys-NH$_2$ (48) Tr$_1$=9.95, Tr$_2$=12.54; LRMS (EI) calcd for C$_{38}$H$_{49}$N$_{13}$O$_6$(M+H)$^+$, 784.4. Found m/e 784.4 (M+H)$^+$. His-D-Trp-azaGly-Ala-D-Phe-Lys-NH$_2$ (49) Tr$_1$=8.88, Tr$_2$=8.95; LRMS (EI) calcd for C$_{36}$H$_{48}$N$_{12}$O$_6$(M+H)$^+$, 745.4. Found m/e 745.4 (M+H)$^+$, 767.4 (M+23)$^+$. His-D-Ala-azaGly-Trp-D-Phe-Lys-NH$_2$ (50) Tr$_1$=9.64, Tr$_2$=9.80; LRMS (EI) calcd for C$_{36}$H$_{48}$N$_{12}$O$_6$(M+H)$^+$, 745.4. Found m/e 745.4 (M+H)$^+$. Ala-D-Trp-azaGly-Trp-D-Phe-Lys-NH$_2$ (51) Tr$_1$=15.61, Tr$_2$=17.95$^b$; LRMS (EI) calcd for C$_{41}$H$_{51}$N$_{11}$O$_6$ (M+H)$^+$, 794.4. Found m/e 794.4 (M+H)$^+$. His-D-Trp-azaLeu-Trp-D-Phe-Ala-NH$_2$ (52) Tr$_1$=17.54, Tr$_2$=13.64; LRMS (EI) calcd for C$_{45}$H$_{54}$H$_{54}$N$_{12}$O$_6$ (M+H)$^+$, 859.4. Found m/e 859.4 (M+H)$^+$, 881.4 (M+23)$^+$. His-D-Trp-azaLeu-Trp-D-Ala-Lys-NH$_2$ (53) Tr$_1$=11.65, Tr$_2$=11.73; LRMS (EI) calcd for C$_{42}$H$_{57}$N$_{13}$O$_6$(M+H)$^+$, 840.5. Found m/e 840.5 (M+H)$^+$, 862.4 (M+23)$^+$. His-D-Trp-azaLeu-Ala-D-Phe-Lys-NH$_2$ (54) Tr$_1$=14.55, Tr$_2$=12.10; LRMS (EI) calcd for C$_{40}$H$_{56}$N$_{12}$O$_6$ (M+H)$^+$, 801.5. Found m/e 801.5 (M+H)$^+$. His-D-Ala-azaLeu-Trp-D-Phe-Lys-NH$_2$ (55) Tr$_1$=11.16, Tr$_2$=10.60$^b$; LRMS (EI) calcd for C$_{40}$H$_{56}$N$_{12}$O$_6$ (M+H)$^+$, 801.4. Found m/e 801.4 (M+H)$^+$, 823.4 (M+23)$^+$. Ala-D-Trp-azaLeu-Trp-D-Phe-Lys-NH$_2$ (56) Tr$_1$=17.08, Tr$_2$=12.08$^c$; LRMS (EI) calcd for C$_{45}$H$_{59}$N$_{11}$O$_6$ (M+H)$^+$, 850.5. Found m/e 850.5 (M+H)$^+$, 872.5 (M+23)$^+$. His-D-Trp-Ala-azaPhe-D-Phe-Ala-NH$_2$ (57) Tr$_1$=16.55, Tr$_2$=11.96; LRMS (EI) calcd for C$_{40}$H$_{47}$N$_{11}$O$_6$ (M+H)$^+$, 778.4. Found m/e 778.4 (M+H)$^+$, 800.4 (M+23)$^+$. His-D-Trp-Ala-azaPhe-D-Ala-Lys-NH$_2$ (58) Tr$_1$=10.00, Tr$_2$=10.10; LRMS (EI) calcd for C$_{37}$H$_{50}$N$_{12}$O$_6$ (M+H)$^+$, 759.4. Found m/e 759.4 (M+H)$^+$, 781.4 (M+23)$^+$. His-D-Ala-Ala-azaPhe-D-Phe-Lys-NH$_2$ (59) Tr$_1$=8.43, Tr$_2$=9.97; LRMS (EI) calcd for C$_{37}$H$_{49}$N$_{11}$O$_6$ (M+H)$^+$, 720.4. Found m/e 720.4 (M+H)$^+$, 742.4 (M+23)$^+$. Ala-D-Trp-Ala-azaPhe-D-Phe-Lys-NH$_2$ (60) Tr$_1$=15.86, Tr$_2$=10.62; LRMS (EI) calcd for C$_{40}$H$_{52}$N$_{10}$O$_6$(M+H)$^+$, 769.4. Found m/e 791.4 (M+23)$^+$. His-D-Trp-azaGly-Pro-D-Phe-Lys-NH$_2$ (61) Tr$_1$=8.90, Tr$_2$=11.04; LRMS (EI) calcd for C$_{38}$H$_{50}$N$_{12}$O$_6$ (M+H)$^+$, 771.4. Found m/e 771.4 (M+H)$^+$, 793.4 (M+23)$^+$. His-D-Trp-azaPro-Trp-D-Phe-Lys-NH$_2$ (62) Tr$_1$=12.85, Tr$_2$=17.73; LRMS (EI) calcd for C$_{46}$H$_{55}$N$_{13}$O$_6$ (M+H)$^+$, 900.5. Found m/e 900.5 (M+H)$^+$. His-D-Trp-Ala-azaPro-D-Phe-Lys-NH$_2$ (63) Tr$_1$=10.94, Tr$_2$=10.95; LRMS (EI) calcd for C$_{39}$H$_{52}$N$_{12}$O$_6$(M+H)$^+$, 785.4. Found m/e 785.4 (M+H)$^+$, 807.4 (M+23)$^+$. His-D-Trp-Ala-Trp-azaPro-Lys-NH$_2$ (64) Tr$_1$=9.96, Tr$_2$=12.61; LRMS (EI) calcd for C$_{40}$H$_{51}$N$_{13}$O$_6$ (M+H)$^+$, 824.4. Found m/e 824.4 (M+H)$^+$, 846.4 (M+23)$^+$. (D/L)His-azaPro-Ala-Trp-D-Phe-Lys-NH$_2$ (65) Tr$_1$=9.79, Tr$_2$=9.82; LRMS (EI) calcd for C$_{38}$H$_{50}$N$_{12}$O$_6$ (M+H)$^+$, 785.4. Found m/e 785.4 (M+H)$^+$, 807.4 (M+23)$^+$.

$^a$ Unless otherwise noted, analytical HPLC analyses were performed on a 5 µM 150 mm×4.6 mm C18 Gemini column with a flow rate of 0.5 ml/min using a 2-40 gradient from water (0.1% FA) to CH$_3$CN (0.1% FA) or MeOH (0.1% FA). $^b$ Analytical HPLC analyses were performed using the same column as in a, with a 10-50 gradient from water (0.1% FA) to CH$_3$CN (0.1% FA) or MeOH (0.1% FA). $^c$ Analytical HPLC analyses were performed using the same column as in a, with a 20-80 gradient from water (0.1% FA) to CH$_3$CN (0.1% FA) or MeOH (0.1% FA). $^d$ Analytical HPLC analyses were performed using the same column as in a, with a 0-60 gradient from water (0.1% FA) to CH$_3$CN (0.1% FA). $^e$ Analytical HPLC analyses were performed using the same column as in a, with a 10-80 gradient from water (0.1% FA) to CH$_3$CN (0.1% FA).

TABLE 1

| Entry # | Compound # | Structure | MS (M + 1) |
|---|---|---|---|
| 12 | DBG-145p | His-D-Trp-azaAla-Trp-D-Phe-Lys-NH₂ | 874.3 |
| 13 | DBG-168-1 | CH₃(CH₂)₄CO-D-Trp-azaAla-D-Phe-Lys-NH₂ | 835.4 |
| 14 | DBG-168-2 | (CH₃)₂CHCH₂CO-D-Trp-azaAla-D-Phe-Lys-NH₂ | 821.4 |

TABLE 1-continued
| Entry # | Compound # | Structure | MS (M + 1) |
|---|---|---|---|
| 15 | DBG-168-3 | 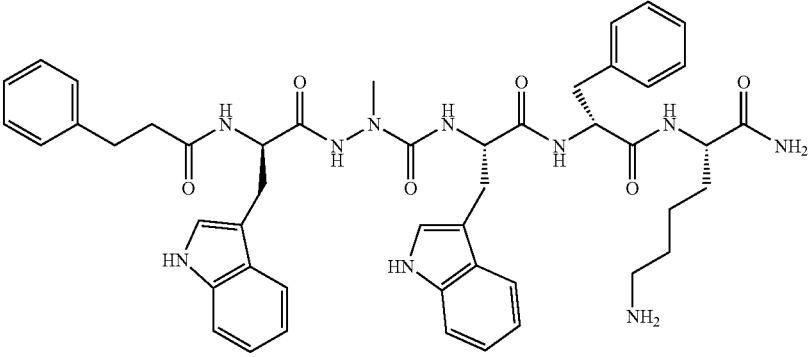 Ph—(CH₂)₂—CO-D-Trp-azaAla-Trp-D-Phe-Lys-NH₂ | 869.4 |
| 16 | DBG-168-4 | 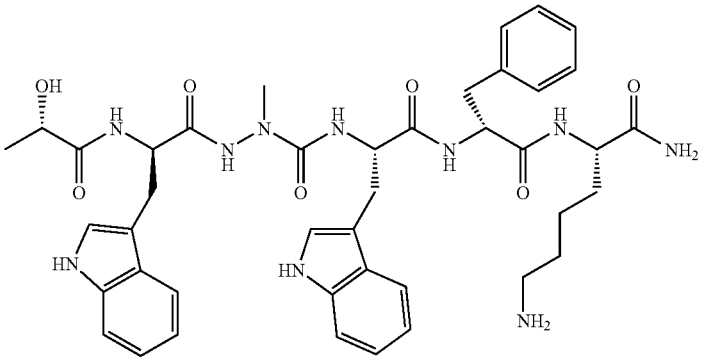 CH₃CH(OH)—CO-D-Trp-azaAla-Trp-D-Phe-Lys-NH₂ | 809.4 |
| 17 | DBG-168-5 | 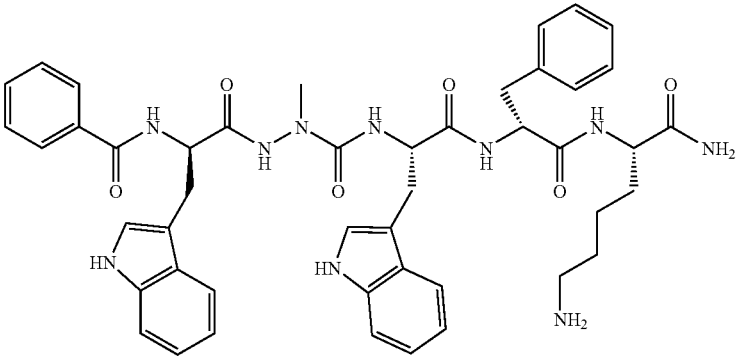 Ph—CO-D-Trp-azaAla-Trp-D-Phe-Lys-NH₂ | 841.4 |

TABLE 1-continued
| Entry # | Compound # | Structure | MS (M + 1) |
|---|---|---|---|
| 18 | DBG-168-6 | 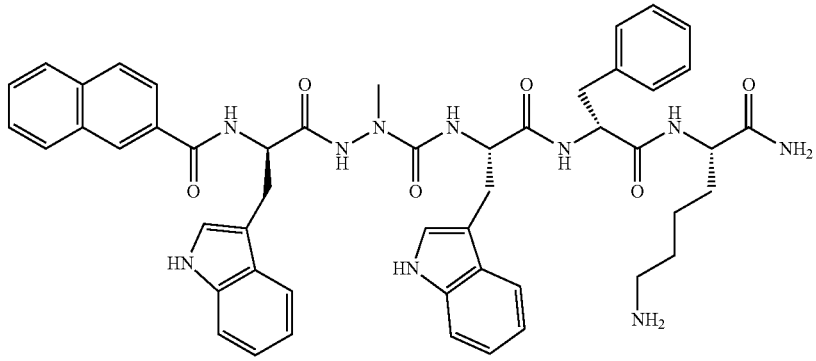<br>Nal-1-CO-D-Trp-azaAla-Trp-D-Phe-Lys-NH$_2$ | 891.4 |
| 19 | DBG-168-7 | 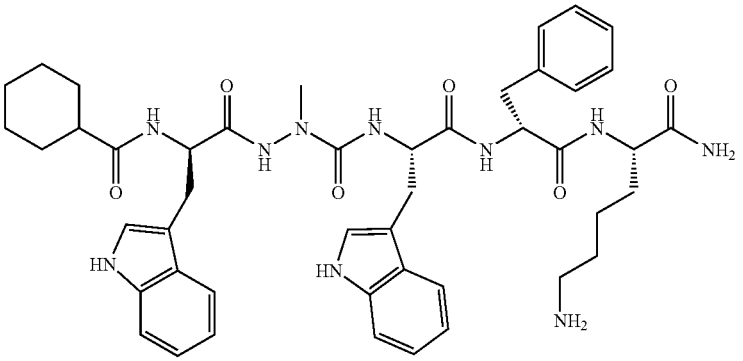<br>Cy-CO-D-Trp-azaAla-Trp-D-Phe-Lys-NH$_2$ | 847.4 |
| 20 | DBG-168-8p | 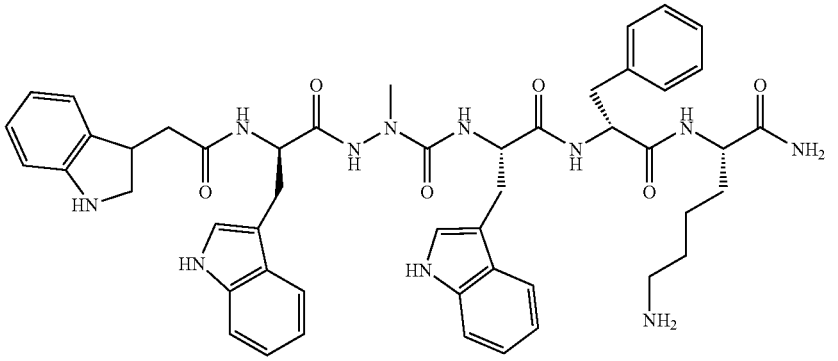<br>In—CO-D-Trp-azaAla-Trp-D-Phe-Lys-NH$_2$ | 896.4 |

TABLE 1-continued
| Entry # | Compound # | Structure | MS (M + 1) |
|---|---|---|---|
| 21 | DBG-168-10p | 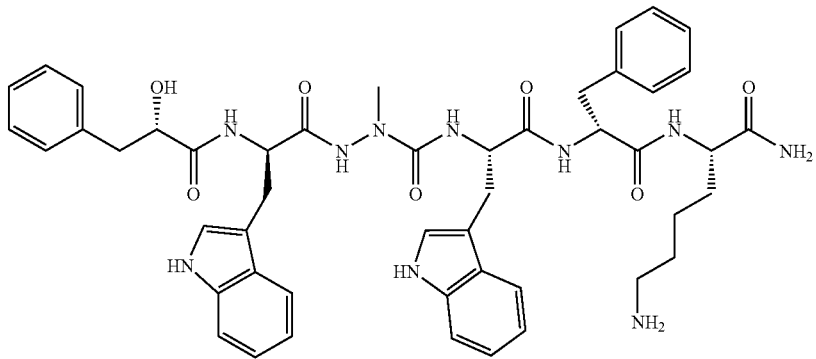 Ph—CH₂—CH(OH)—CO-D-Trp-azaAla-Trp-D-Phe-Lys-NH₂ | 885.4 |
| 22 | DBG-175p | 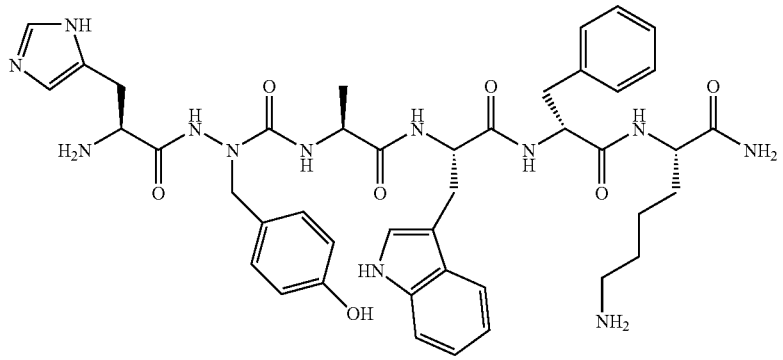 His-azaTyr-Ala-Trp-D-Phe-Lys-NH₂ | 851.3 |
| 23 | DBG-178p | 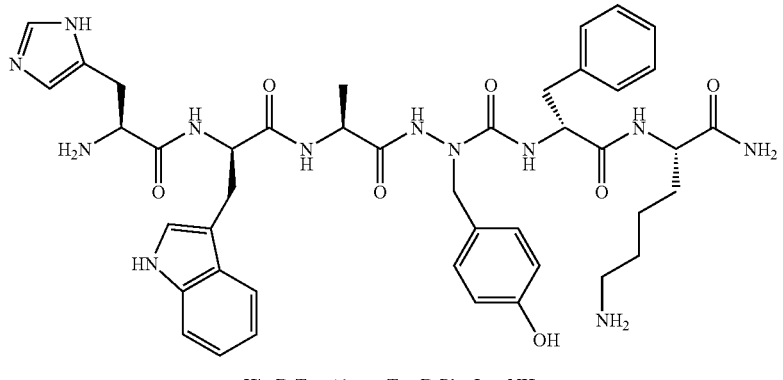 His-D-Trp-Ala-azaTyr-D-Phe-Lys-NH₂ | 851.3 |

TABLE 1-continued
| Entry # | Compound # | Structure | MS (M + 1) |
|---|---|---|---|
| 24 | DBG-188p | 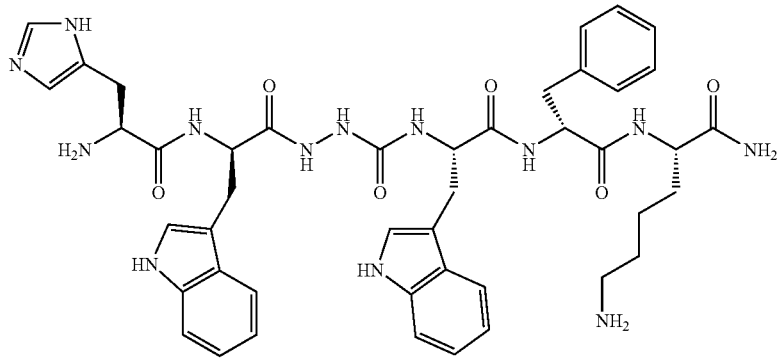 His-D-Trp-azaGly-Trp-D-Phe-Lys-NH$_2$ | 860.3 |
| 25 | DBG-201-A | 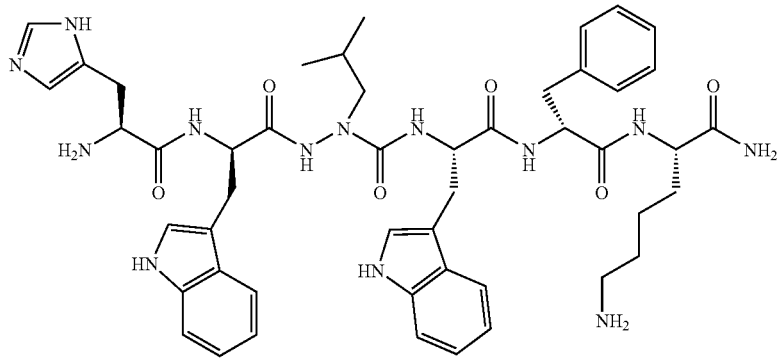 His-D-Trp-azaLeu-Trp-D-Phe-Lys-NH$_2$ | |
| 26 | DBG-253-1 | 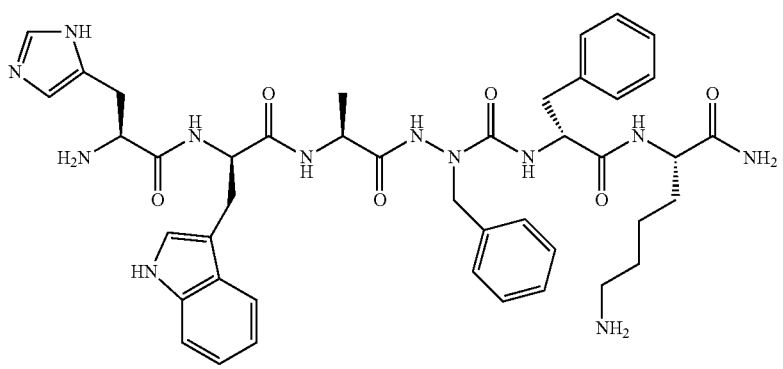 His-D-Trp-Ala-azaPhe-D-Phe-Lys-NH$_2$ | 835.5 |

TABLE 1-continued
| Entry # | Compound # | Structure | MS (M + 1) |
|---|---|---|---|
| 27 | DBG-253-2 | 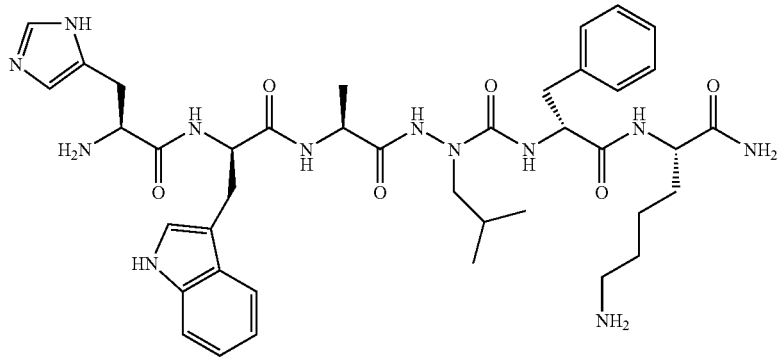<br>His-D-Trp-Ala-azaLeu-D-Phe-Lys-NH$_2$ | 801.5 |
| 28 | DBG-253-3 | 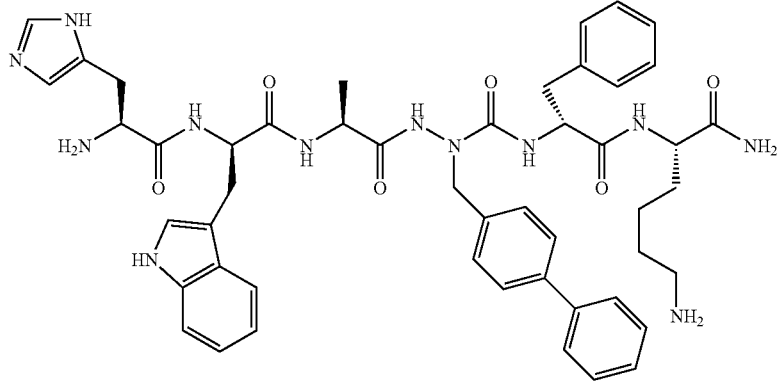<br>His-D-Trp-Ala-azaBip-D-Phe-Lys-NH$_2$ | 911.5 |
| 29 | DBG-253-4 | 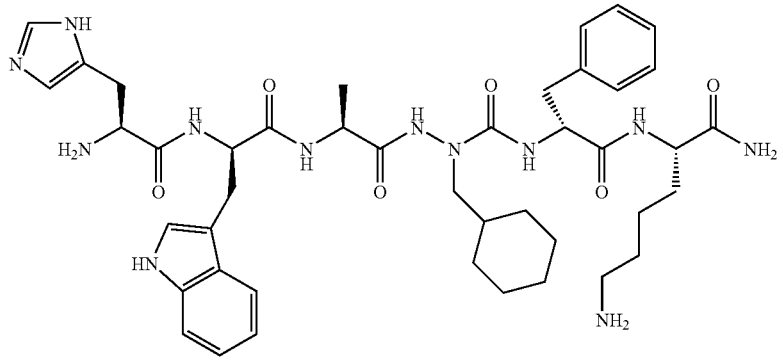<br>His-D-Trp-Ala-azaCha-D-Phe-Lys-NH$_2$ | 841.5 |

TABLE 1-continued
| Entry # | Compound # | Structure | MS (M + 1) |
|---|---|---|---|
| 30 | DBG-253-5 | 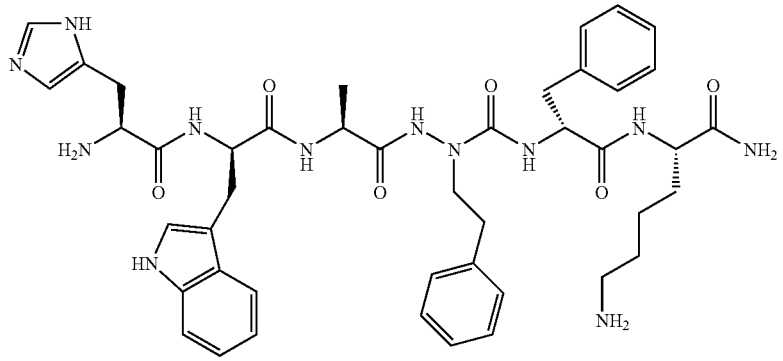<br>His-D-Trp-Ala-azahomoPhe-D-Phe-Lys-NH$_2$ | 849.5 |
| 31 | DBG-253-6 | 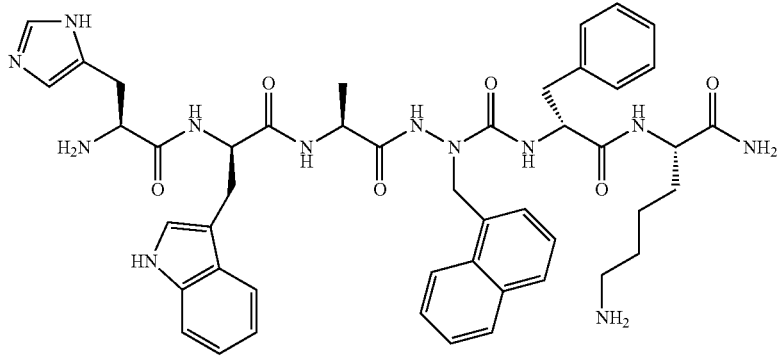<br>His-D-Trp-Ala-azaNal-1-D-Phe-Lys-NH$_2$ | 885.5 |
| 32 | DBG-253-7 | 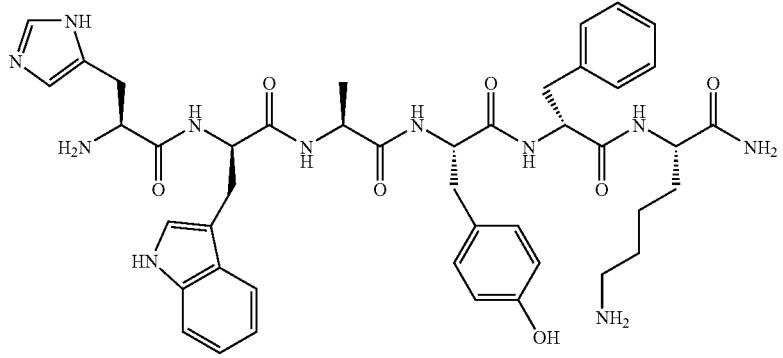<br>His-D-Trp-Ala-Tyr-D-Phe-Lys-NH$_2$ | 850.5 |

TABLE 1-continued
| Entry # | Compound # | Structure | MS (M + 1) |
|---|---|---|---|
| 33 | DBG-253-8 | 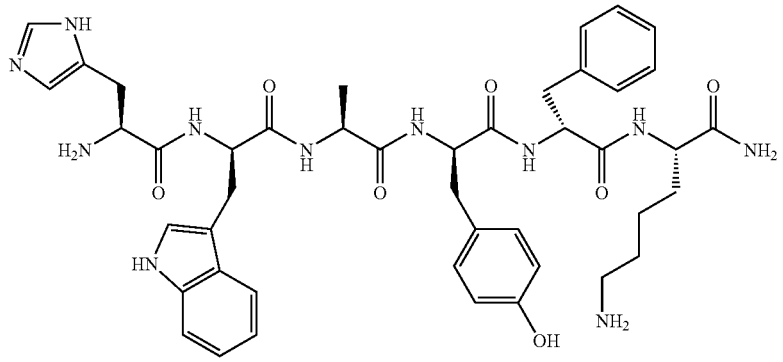 His-D-Trp-Ala-D-Tyr-D-Phe-Lys-NH$_2$ | 850.5 |
| 34 | DBG-253-9 | 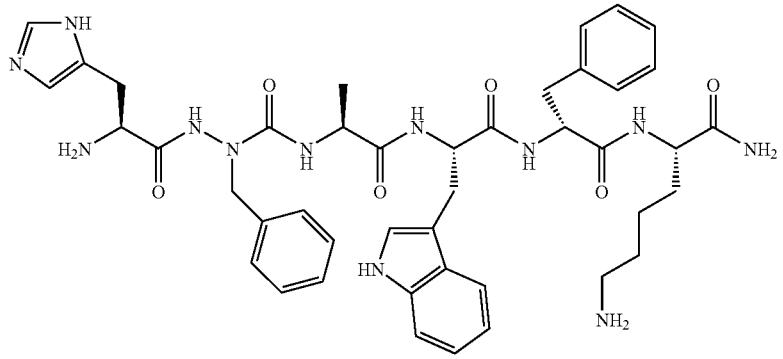 His-azaPhe-Ala-Trp-D-Phe-Lys-NH$_2$ | 835.5 |
| 35 | DBG-253-10 | 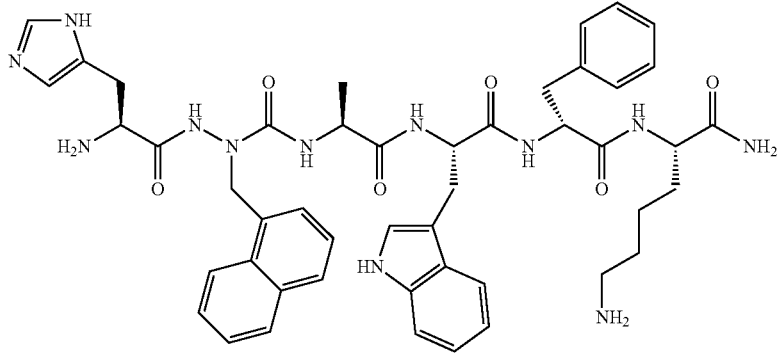 His-azaNal-1-Ala-Trp-D-Phe-Lys-NH$_2$ | 885.5 |

TABLE 1-continued

| Entry # | Compound # | Structure | MS (M + 1) |
|---|---|---|---|
| 36 | DBG-253-11 | His-azahomoPhe-Ala-Trp-D-Phe-Lys-NH₂ | 849.5 |
| 37 | DBG-253-12 | His-azaBip-Ala-Trp-D-Phe-Lys-NH₂ | 911.5 |
| 38 | DBG-253-13 | His-azaCha-Ala-Trp-D-Phe-Lys-NH₂ | 841.5 |

TABLE 1-continued
| Entry # | Compound # | Structure | MS (M + 1) |
|---|---|---|---|
| 39 | CP-1A(i) | 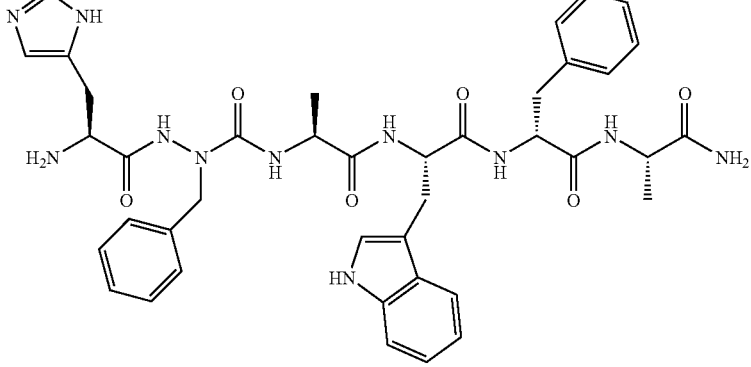
His-azaPhe-Ala-Trp-D-Phe-Ala-NH$_2$ | 778.4 |
| 40 | CP-1A(ii) | 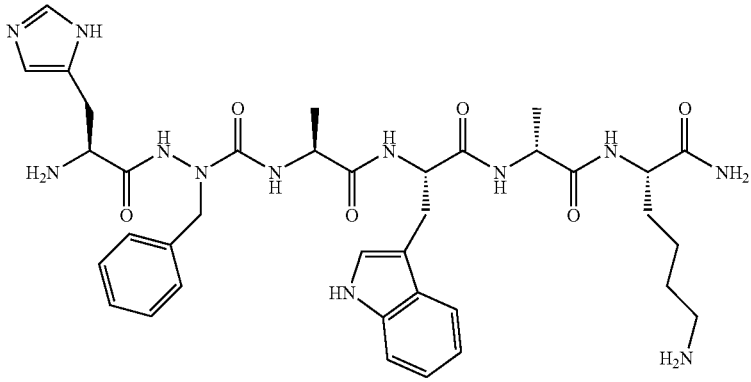
His-azaPhe-Ala-Trp-D-Ala-Lys-NH$_2$ | 759.4 |
| 41 | CP-1A(iii) | 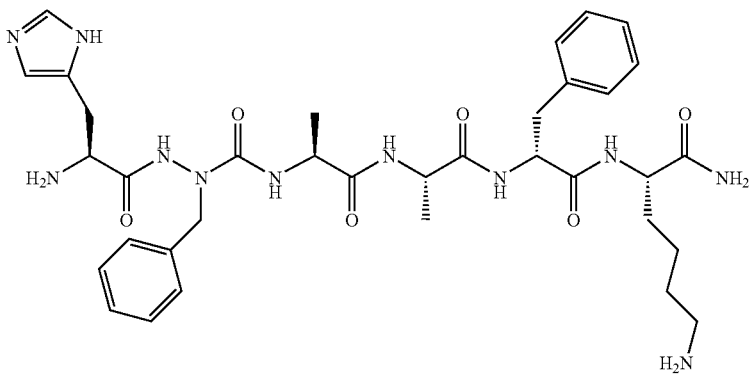
(D/L)His-azaPhe-Ala-Ala-D-Phe-Lys-NH$_2$ | 720.4 |

TABLE 1-continued

| Entry # | Compound # | Structure | MS (M + 1) |
|---|---|---|---|
| 42 | CP-1A(iv) | Ala-azaPhe-Ala-Trp-D-Phe-Lys-NH$_2$ | 769.4 |
| 43 | CP-1B(i) | His-azaTyr-Ala-Trp-D-Phe-Ala-NH$_2$ | 794.4 |
| 44 | CP-1B(ii) | His-azaTyr-Ala-Trp-D-Ala-Lys-NH$_2$ | 775.4 |

TABLE 1-continued
| Entry # | Compound # | Structure | MS (M + 1) |
|---|---|---|---|
| 45 | CP-1B(iii) | 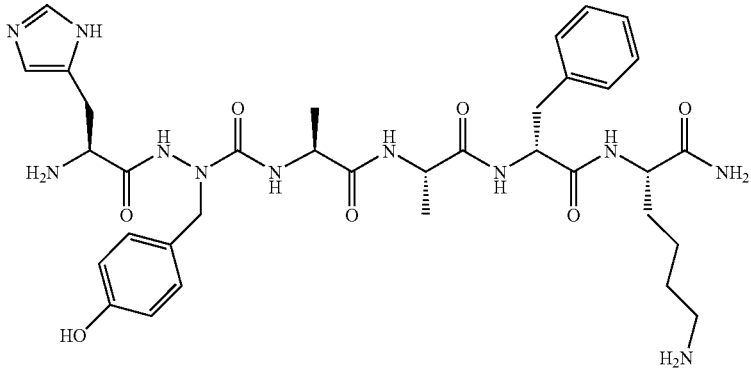<br>(D/L)His-azaTyr-Ala-Ala-D-Phe-Lys-NH$_2$ | 736.4 |
| 46 | CP-1B(iv) | 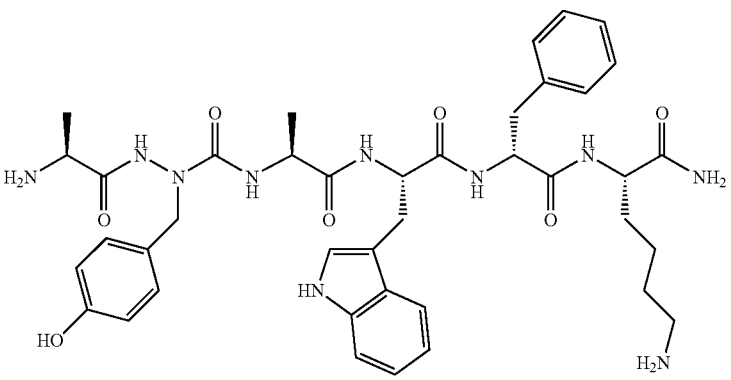<br>Ala-azaTyr-Ala-Trp-D-Phe-Lys-NH$_2$ | 785.4 |
| 47 | CP-2A(i) | 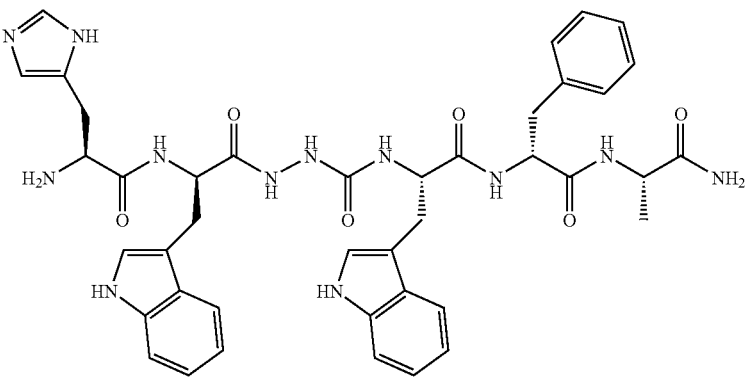<br>His-D-Trp-azaGly-Trp-D-Phe-Ala-NH$_2$ | 803.4 |

TABLE 1-continued

| Entry # | Compound # | Structure | MS (M + 1) |
|---|---|---|---|
| 48 | CP-2A(ii) | His-D-Trp-azaGly-Trp-D-Ala-Lys-NH$_2$ | 784.4 |
| 49 | CP-2A(iii) | His-D-Trp-azaGly-Ala-D-Phe-Lys-NH$_2$ | 745.4 |
| 50 | CP-2A(iv) | His-D-Ala-azaGly-Trp-D-Phe-Lys-NH$_2$ | 745.4 |

TABLE 1-continued

| Entry # | Compound # | Structure | MS (M + 1) |
|---|---|---|---|
| 51 | CP-2A(v) | His-D-Trp-azaGly-Trp-D-Phe-Lys-NH$_2$ | 794.4 |
| 52 | CP-2B(i) | His-D-Trp-azaLeu-Trp-D-Phe-Ala-NH$_2$ | 859.4 |
| 53 | CP-2B(ii) | His-D-Trp-azaLeu-Trp-D-Ala-Lys-NH$_2$ | 840.5 |

TABLE 1-continued

| Entry # | Compound # | Structure | MS (M + 1) |
|---|---|---|---|
| 54 | CP-2B(iii) | His-D-Trp-azaLeu-Ala-D-Phe-Lys-NH₂ | 801.5 |
| 55 | CP-2B(iv) | His-D-Ala-azaLeu-Trp-D-Phe-Lys-NH₂ | 801.5 |
| 56 | CP-2B(v) | Ala-D-Trp-azaLeu-Trp-D-Phe-Lys-NH₂ | 850.5 |

| Entry # | Compound # | Structure | MS (M + 1) |
|---|---|---|---|
| 57 | CP-3(i) | 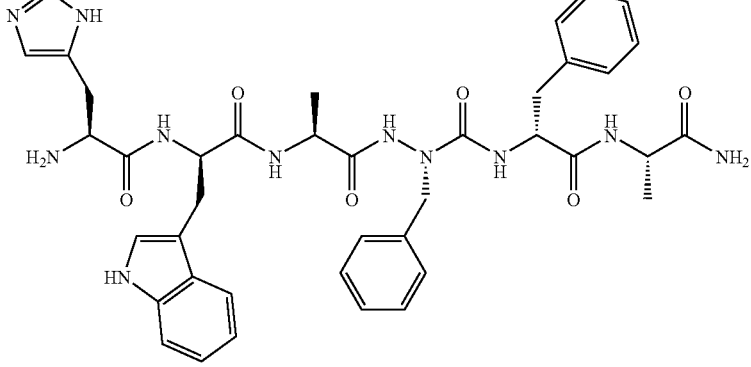<br>His-D-Trp-Ala-azaPhe-D-Phe-Ala-NH$_2$ | 778.4 |
| 58 | CP-3(ii) | 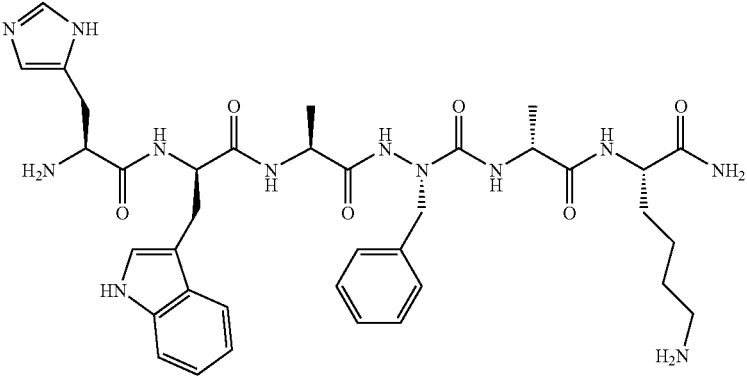<br>His-D-Trp-Ala-azaPhe-D-Ala-Lys-NH$_2$ | 759.4 |
| 59 | CP-3(iii) | 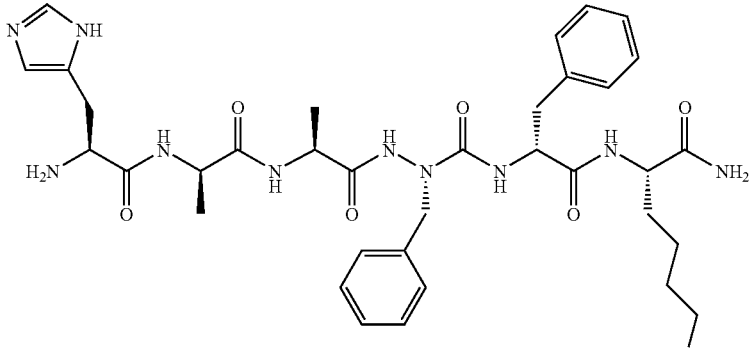<br>His-D-Ala-Ala-azaPhe-D-Phe-Lys-NH$_2$ | 720.4 |

TABLE 1-continued

| Entry # | Compound # | Structure | MS (M + 1) |
|---|---|---|---|
| 60 | CP-3(iv) | Ala-D-Trp-Ala-azaPhe-D-Phe-Lys-NH$_2$ | 769.4 |
| 61 | CP-Azagly_Pro | His-D-Trp-azaGly-Pro-D-Phe-Lys-NH$_2$ | 771.4 |
| 62 | CP-AP-4 | His-D-Trp-azaPro-Trp-D-Phe-Lys-NH$_2$ | 900.5 |

TABLE 1-continued
| Entry # | Compound # | Structure | MS (M + 1) |
|---|---|---|---|
| 63 | CP-AP-3 | 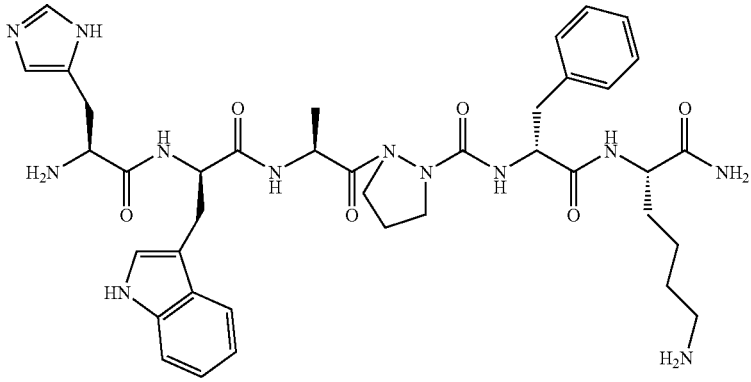 His-D-Trp-Ala-azaPro-D-Phe-Lys-NH$_2$ | 785.4 |
| 64 | CP-AP-2 | 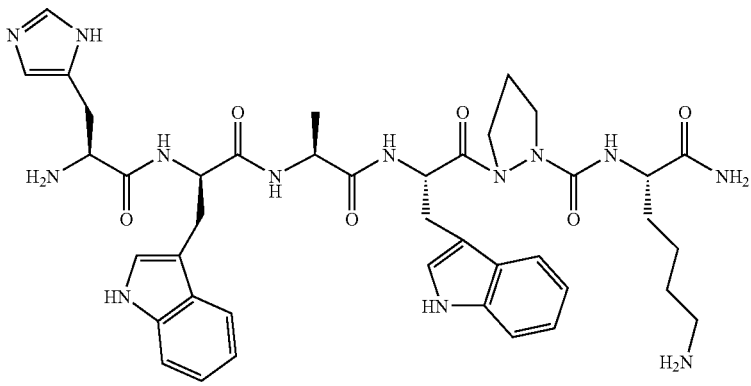 His-D-Trp-Ala-Trp-azaPro-Lys-NH$_2$ | 824.4 |
| 65 | CP-AP-5 | 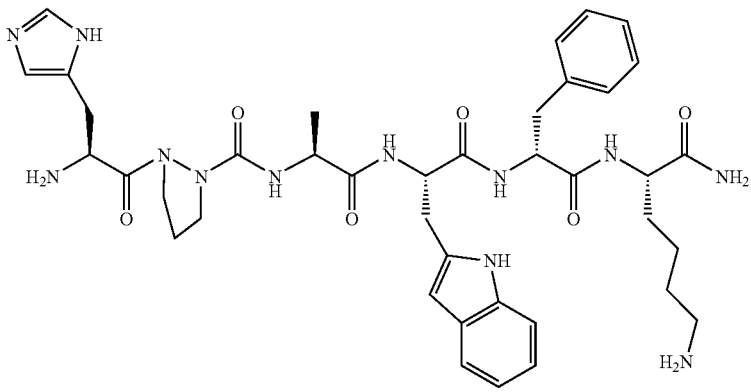 His-azaPro-Ala-Trp-D-Phe-Lys-NH$_2$ | 785.4 |

TABLE 1-continued
| Entry # | Compound # | Structure | MS (M + 1) |
|---|---|---|---|
| 66 | ZS554-F29 | 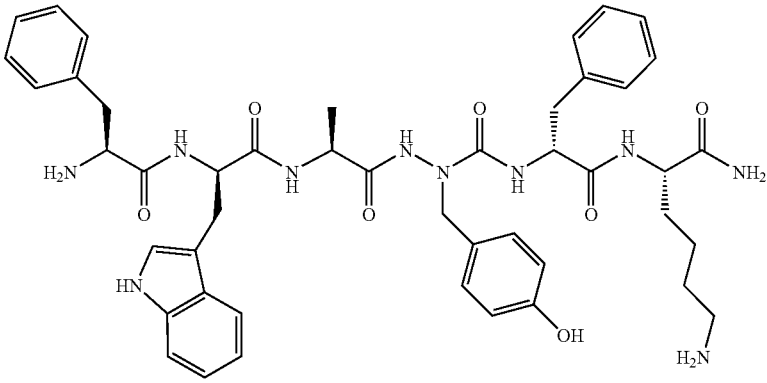<br>Phe-D-Trp-Ala-AzaTyr-D-Phe-Lys-NH$_2$ | 861.3 |
| 67 | ZS555-F40 | 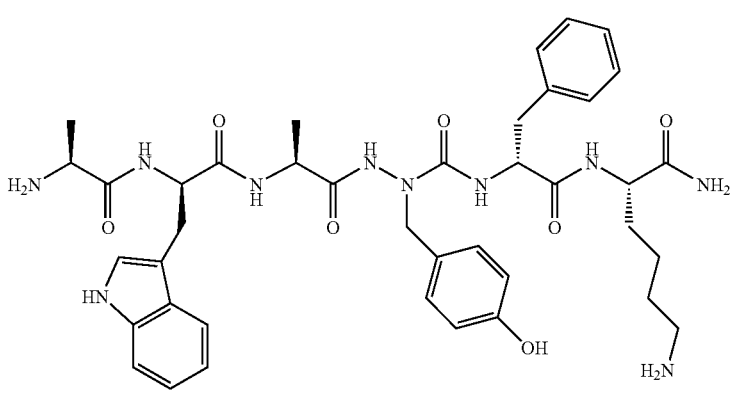<br>Ala-D-Trp-Ala-AzaTyr-D-Phe-Lys-NH$_2$ | 785.3 |
| 68 | ZS556 | 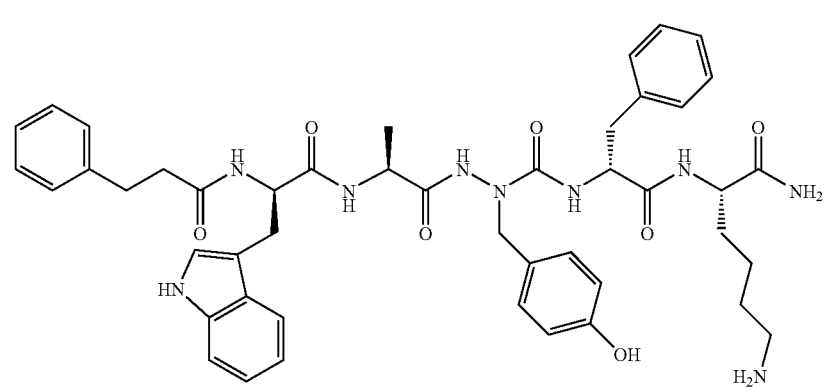<br>Hydrocinnamyl-D-Trp-Ala-AzaPhe-D-Phe-Lys-NH$_2$ | 846.5 |

TABLE 1-continued

| Entry # | Compound # | Structure | MS (M + 1) |
|---|---|---|---|
| 69 | DS85C | His-D-Trp-Ala-aza-(p-bromo)Phe-D-Phe-Lys-NH$_2$ | 913.5 and 916.2 |
| 70 | DS86D | His-D-Trp-aza-(propargyl)Gly-Trp-D-Phe-Lys-NH$_2$ | 900.4 |

[a] Analytical HPLC analyses were performed on a TARGA column from Higgins Analytical, Inc. (4.6 × 250 mm, 5 µm, C$_{18}$) with a flow rate of 1.5 mL/min using a 40 min linear gradient from water (0.1% TFA) to CH$_3$CN (0.1% TFA).
[b] HPLC purity at 214 nm of the crude peptide
[c] HPLC purity at 214 nm of the purified peptide
[d] Crude yield according to manufacturer's reported loading of the rink resin
[e] Yields after purification by RP-HPLC are based on manufacturer's reported loading for Rink resin.

The yields and purities of compounds 39-65 are illustrated in Table 2.

TABLE 2

Yields and Purities of compounds 39-65

| Item/Entry No. | T$_R$ (min) in ACN[a] | T$_R$ (min) in MEOH | HPLC purity at 214 nm[d] | Yield (%)[f] | Expected Mass | Mass[g] |
|---|---|---|---|---|---|---|
| 39 | 15.54 | 11.05 | 96.8% | 4.38 | 778.37108 | 778.37835, 800.36030 |
| 40 | 9.08 | 9.11 | >99% | 1.15 | 759.39763 | 759.40490, 781.38685 |
| 41 | 9.99 | 11.93 | 1:1 mixture, >99%[e] | 3.95 | 720.39400 | 720.39371 |
| 42 | 15.67 | 7.80[c] | 93% | 6.39 | 769.41440 | 769.41370 |
| 43 | 14.89 | 21.34 | 98% | 3.72 | 794.36599 | 794.37327, 816.35521 |
| 44 | 8.79 | 10.79 | 97% | 4.90 | 775.39254 | 775.39982, 797.38176 |
| 45 | 8.13 | 8.18 | 1:3 mixture, >99%[e] | 12.5 | 736.38164 | 736.38892, 758.37086 |
| 46 | 13.19 | 19.02 | >99% | 3.65 | 785.40932 | 785.40858, 807.38983 |
| 47 | 11.01[b] | 18.56[b] | 99% | 4.98 | 803.36633 | 803.37360, 825.35555 |
| 48 | 9.95 | 12.54 | >99% | 1.60 | 784.39288 | 784.40015 |
| 49 | 8.88 | 8.95 | >99% | 6.16 | 745.38198 | 745.38925, 767.37120 |
| 50 | 9.64 | 9.80 | >99% | 4.59 | 745.38198 | 745.38823 |
| 51 | 15.61 | 17.95[b] | 99% | 6.79 | 794.40238 | 794.40965 |
| 52 | 17.54 | 13.64[c] | >99% | 3.83 | 859.42893 | 859.43620, 881.41815 |
| 53 | 11.65 | 11.73 | >99% | 7.22 | 840.45548 | 840.46275, 862.44470 |
| 54 | 14.55 | 12.10 | >99% | 3.57 | 801.45185 | 801.45061 |
| 55 | 11.16 | 10.60[b] | >99% | 3.28 | 801.44458 | 801.45185, 823.43380 |
| 56 | 17.08 | 12.08[c] | >99% | 4.26 | 849.46498 | 850.47226, 872.45420 |

TABLE 2-continued

Yields and Purities of compounds 39-65

| Item/Entry No. | $T_R$ (min) in ACN[a] | $T_R$ (min) in MEOH | HPLC purity at 214 nm[d] | Yield (%)[f] | Expected Mass | Mass[g] |
|---|---|---|---|---|---|---|
| 57 | 16.55 | 11.96 | >99% | 9.19 | 778.37108 | 778.37835, 800.36030 |
| 58 | 10.00 | 10.10 | >99% | 1.72 | 759.39763 | 759.40406, 781.38696 |
| 59 | 8.43 | 9.97 | >99% | 8.50 | 720.39400 | 720.39526, 742.37676 |
| 60 | 15.86 | 10.62[c] | >99% | 6.86 | 769.40713 | 791.39635 |
| 61 | 8.90 | 11.04 | >99% | 2.64 | 771.39763 | 771.40490, 793.38685 |
| 62 | 12.85 | 17.73 | >99% | 2.26 | 900.45548 | 900.46164 |
| 63 | 10.94 | 10.95 | >99% | 2.02 | 785.42055 | 785.42010, 807.39584 |
| 64 | 9.96 | 12.61 | >99% | 1.00 | 824.43145 | 824.43075, 846.41257 |
| 65 | 9.79 | 9.82 | >99%, mixture[e] | 1.00 | 785.42055 | 785.42159, 807.39807 |

[a]Unless otherwise noted, analytical HPLC analyses were performed on a 5 μM 150 mm × 4.6 mm C18 Gemini column with a flow rate of 0.5 ml/min using a 2-40 gradient from water (0.1% FA) to $CH_3CN$ (0.1% FA) or MeOH (0.1% FA).
[b]Analytical HPLC analyses were performed using the same column as in a, with a 10-50 gradient from water (0.1% FA) to $CH_3CN$ (0.1% FA) or MeOH (0.1% FA).
[c]Analytical HPLC analyses were performed using the same column as in a, with a 20-80 gradient from water (0.1% FA) to $CH_3CN$ (0.1% FA) or MeOH (0.1% FA).
[d]HPLC purity at 214 nm of the purified peptide.
[e]Mixture of isomers shows up as two distinct peaks with identical masses.
[f]Yields after purification by HPLC are based on manufacturer's reported loading for Rink resin.
[g]Observed masses corresponding to the $H^+$ and $Na^+$ adducts.

CD36 Receptor Covalent Binding Assay

For the determination of binding affinity of azapeptide derivatives of GHRP-6 towards the scavenger receptor CD36, competition curves were set using rat cardiac membrane preparation as source of CD36 and photoactivatable derivative [$^{125}$I] Tyr-Bpa-Ala-hexarelin as covalent photolabelling tracer as reported previously (45). Azapeptide derivatives (DBG series) were used as competition ligands at concentrations ranging from $10^{-7}$ to $5 \cdot 10^{-5}$ M. The $IC_{50}$s determined from the competition curves for the DBG compounds tested and that of hexarelin, the GHRP prototype reported as ligand of CD36 (38) are compiled in Table 3.

According to the structure-binding activity relationship of the compounds tested, favoring the interaction of two aromatic constituents at the ends of the peptide chain oriented by the curvature of the chain is essential for the selective binding affinity towards CD36. For example, the replacement of the Trp4 residue of GHRP-6 by azaPhe or azaTyr improved the selectivity by reducing the binding affinity for GHS-R1a receptor and maintaining the binding activity to CD36 (DBG253-1 and DBG 178).

Methodology for the CD36 Covalent Photolabelled Binding Assay

Cardiac Membrane Preparation.

The hearts from Sprague Dawley rats (300 g-325 g) from Charles River, used as a source of cardiac membranes, were prepared as follows: the heart was washed with ice-cold saline, and fatty and connective tissue was removed. The tissue was cut into small pieces with scissors and placed in a Sorvall centrifuge tube containing 5 ml/g of fresh tissue of Buffer A (10 mM $NaHCO_3$, 5 mM $NaN_3$, 10 μM Pefabloc, 0.1 μM Aprotinin, 1 μM Pepstatin A, 1 μM Leupeptin, pH 7.0). The suspension was homogenized with a Polytron at low speed, 3×15 sec. The homogenate was centrifuged at 8700×g for 20 min and the supernatant was put on ice. The pellet was resuspended and homogenized with a Glass-teflon Potter by 5 strokes. The homogenate was centrifuged at 8700×g for 10 min and this supernatant was combined with the first supernatant. The supernatant fluid was centrifuged at 35 000×g for 20 min, yielding a second pellet fraction that was suspended thoroughly in a glass homogenizer with a Teflon pestle in 20 ml/g of fresh tissue of Buffer B (20 mM Tris-maleate, 0.6M KCl, pH 6.8). The resulting suspension was centrifuged again at 35 000×g for 60 min. The third pellet fraction was resuspended thoroughly in a glass homogenizer with a Teflon pestle in 20 ml/g of fresh tissue of Buffer C (10 mM Tris/HCl buffer pH 7.4) followed with another centrifugation at 35 000×g for 60 min. The harvested precipitate was then suspended in a small volume (1-2 ml/g of fresh tissue) of 50 mM Tris/HCl buffer pH 7.4) containing 2 mM EGTA. The resulting membrane preparation was frozen at −80° C. Protein concentration was determined with bicinchoninic acid (BCA) method, using BSA as standard.

Radiolabelling of the Tracer

The iodination procedure was performed in the darkness. Tyr-Bpa-Ala-Hexarelin (10 nmol) was mixed with 100 ng of lactoperoxidase and 1 mCi of $Na^{125}I$ in a volume of 30 ul of 0.1N sodium acetate buffer pH 5.6. The reaction was started by adding 5 ul (3 nmol) of $H_2O_2$. The incubation was carried out at 22° C. for 5 min. The addition of $H_2O_2$ was repeated twice with 5 min incubation each time. The reaction was stopped with the addition of 1.4 ml of 0.1% TFA. The iodinated peptide was purified on a reverse-phase Vydac $C_{18}$ column with a 60 min linear gradient (1 ml/min) from 20% to 50% acetonitrile (90%) in 0.1% TFA (10%).

Competition Binding Curves

The receptor binding assays of the photoactivatable ligand were performed as follows: Membranes (200 ug/75 ul) were incubated in the darkness, in 525 ul of 50 mM Tris-HCl pH 7.4 containing 2 mM EGTA (Buffer A) in the presence of a fixed concentration of [$^{125}$I]-Tyr-Bpa-Ala-Hexarelin (750 000 cpm/75 ul) in Buffer B (50 mM Tris-HCl pH 7.4 containing 2 mM EGTA and 0.05% Bacitracin) and of increasing concentrations of DBG derivatives ranging from 0.1 to 50 μM as competition ligands. Nonspecific binding was defined as binding not displaced by 50 μM corresponding peptide. All peptide containing solutions were diluted in Buffer B. Buffer A and B were degassed under vacuum, and used in capped tubes in order to minimize lipid peroxydation. Before the incubation period, all tubes were put under a low flow of nitrogen. All material was kept on ice and the binding assay was performed in darkness. After an incubation period of 60 min at 22° C. (vortexing every 15 min), membranes were submitted to irradiation with UV lamps (365 nm) for 15 min at 4° C. After centrifugation at 12 000×g for 15 minutes, the pellets were resuspended in 150 μl of sample buffer (62 mM Tris-HCl, pH 6.8, 2% SDS, 10% glycerol, 15% 2-mercaptoethanol, and 0.05% bromophenol blue), and boiled for 5 min prior to being subjected to electrophoresis. Proteins (200 μg/100 μl) were separated on 7.5% SDS-PAGE (45 V overnight). The gels resulting from SDS/PAGE were fixed, colored in Coomassie Brilliant Blue R-250, dried, exposed to a storage phosphor intensifying screen (Amersham Biosciences), and analysed by using a Typhoon PhosphorImager (Amersham Biosciences) and ImageQuant 5.0 software to establish competition curves. Protein bands were quantified by densitometry. The covalent binding signal of 87 kDa was analyzed by densitometry using Typhoon Phospholmager™ (Typhoon, Amersham Biosciences) and ImageQuant 5.0™ software to set competition curves.

Specific binding activities were defined as the ratio of the density of the protein band to that of a non-specific band. Results are expressed as the percentage of the density of the pro to that of the total binding band.

GHS-R1a Binding Assay

The binding affinity of the azapeptide derivatives of GHRP-6 towards the ghrelin receptor GHS-R1a was documented by competition binding studies on the membranes of LLCPK-1 overexpressing GHS-R1a source of receptor and [$^{125}$I]-ghrelin (1-28) as radioligand (46). The azapeptide derivatives were used as competition ligands ranging from $10^{-12}$ to $10^{-6}$ M. The $IC_{50}$s of the competition binding curves for these derivatives and that of GHRP-6 and (1-28) ghrelin as natural ligand for GHS-R1a are compiled in Table 3 below. The replacement by aza amino acid residues within the structure of GHRP-6 reduced significantly the binding affinity towards GHS-R1a receptor at least of two decades as compared to that of GHRP-6 and ghrelin which were in the sub-nanomolar to nanomolar ranges.

Methodology for GHS-R1a Binding Assay

Radioiodination of Ghrelin

Rat ghrelin was radioiodinated with Na$^{125}$I using the Iodo-Beads iodination reagent (Pierce #28665). Briefly, an Iodo-bead was incubated with 2 mCi of Na$^{125}$I (Amersham) in 100 μL of 50 mM sodium phosphate buffer, pH 7.0 for 5 min at 22° C. The reaction was started by adding 20 nmol of the peptide (1 mM in 0.1M acetic acid). The tube was incubated for 10 min at 22° C. The iodination was terminated by adding 1 mL of 0.1% TFA. The mono-iodinated peptide was purified by reverse-phase HPLC using a Vydac $C_{18}$ (5 μM) column (30 cm×0.39 cm) in combination with a binary elution system of (A) 0.1% TFA in $H_2O$ and (B) 0.1% TFA, 10% $H_2O$, 90% acetonitrile. Fractions of 0.5 mL were collected and analyzed by its radioactive content.

Expression of Human GHS-R1a in LLC-PK1 Cells

LLC-PK1 cells (ATCC #CL-101) were grown in Dulbecco's modified Eagle's medium (Invitrogen) supplemented with 10% fetal bovine serum (Invitrogen) and 100 units of penicillin/streptomycin (Invitrogen) in a 5% $CO_2$ incubator at 37° C. Cells (1.4×10$^6$) were plated in 100 mm plates and transfected 24 h later with pCDNA3.1-hGHS-R1a (UMR cDNA Resource Center #GHSR0A0000) following the CaHPO$_4$ precipitation method. Briefly, 40 μg of plasmid DNA was diluted in 500 μL of sterile $H_2O$ and added to an equal volume of a 4×CaCl$_2$, pH 7.9 solution (2 mM Tris-HCl, 0.2 mM EDTA, 500 mM CaCl$_2$). The mixture was then added slowly with air bubbles to 1 mL of 2× Hepes-buffered saline, pH 7.1 (50 mM Hepes, 280 mM NaCl, 1.5 mM Na$_2$HPO$_4$). After 30 min at room temperature, 1 mL was distributed evenly over the cells and let overnight. The medium was changed the next morning and the membrane preparation was made two days later.

Membrane Preparation of Transfected LLC-PK1 Cells

Cells were washed twice with PBS and once with ice-cold homogenization buffer (50 mM Tris-HCl, pH 7.3, 5 mM MgCl$_2$, 2.5 mM EDTA, 30 μg/ml bacitracin). Cells were scraped and harvested in 1.5 mL tubes. Cells were then lysed by temperature shock with two freeze/thaw cycles in liquid nitrogen. The tubes were centrifuged at 14000 g for 20 min. Pellets were resuspended in homogenization buffer and stored at −80° C. until used. Total protein concentrations were determined with the BCA protein assay kit (Pierce).

Receptor Binding Assay with $^{125}$I-Ghrelin

Competition experiments were performed by incubating 50 μg of LLC-PK1 membranes expressing human GHS-R1a with 15 fmol of $^{125}$I-Ghrelin and increasing concentrations of unlabeled ghrelin or with increasing concentrations of aza-peptides derivatives in 0.5 mL of binding buffer. Bound radio-labelled ligand was separated from free by filtration on Whatman GF/C filters pretreated with a 1% polyethylenimine solution. Filters were washed with 2×3 mL of washing buffer (50 mM Tris-HCl, pH 7.3, 10 mM MgCl$_2$, 2.5 mM EDTA, 0.015% Triton X-100). Filters were counted in a LKB gamma counter. Curves were analyzed using Prism software (Graph-Pad Software Inc).

Inhibition of Microvascular Sprouting from Aortic Explants

To evaluate the antiangiogenic property of azapeptide derivatives of GHRP-6, a study on the inhibition of vascular sprouting by DBG 178a prototype of azapeptide derivatives at the range concentrations from $10^{-8}$ to $10^{-6}$M were performed on Matrigel-embedded aortic rings collected from CB57BL/6 mice and CD36 null mice on the same background. Sprouting aortic endothelium (Von Willebrand factor positive) expresses CD36 as demonstrated by immunochemistry (FIG. 1). FIG. 1 illustrates disruption of vascular sprouting of aortic endothelium by azapeptide compound DBG178. Sprouting aortic endothelium (Von Willebrand factor positive) expressing CD36 is shown in the upper row of FIG. 1a. Vascular sprouting of aortic rings from C57BL/6 and CD36 null mice in the presence of DBG 178 at 10$^{-7}$M is shown in the lower row of FIG. 1a. Histograms of microvascular sprouts areas (mean±s.e.m) from aortic explants of C57BL/6 and CD36 null mice exposed to DBG concentrations from $10^{-8}$ to $10^{-6}$ M p<0.01 compared with control (Ctl) is shown in FIG. 1b.

DBG 178 significantly inhibited the vascular sprouting of aortic rings from CB57BL/6 mice in a dose dependent manner as shown in FIG. 1. In contrast this inhibitory effect on vascular sprouting of DBG178 was not detected on aortic rings from CD36 null mice. DBG 178 appears to disrupt vascular sprouting in vitro at concentrations ranging from $10^{-7}$ to $10^{-6}$ M and this inhibitory effect is dependent of CD36 expression.

Aortic Rings Preparation and In Vitro Vascular Sprouting Protocol

Aortas were excised from 10-week-old male C57/B16+/+ and CD36−/− mice of C57/B16 background. The fibroadipose tissue was removed and aortas were sectioned into 2-mm-long cross-sections. The +/+ and −/− rings were covered by 50 μl of Matrigel and cultured for 4 days in EGM-2 medium (Clonetics Corp.). Explants were then exposed to vehicle alone or in presence of an azapeptide prototype DBG 178 at the indicated concentrations ($10^{-8}$ to $10^{-6}$M) from day 4 to day 6 of culture in EGM-2 medium. Pictures of each individual explant were taken at day 4 and day 6 and EC growth was measured as the surface covered at day 6 minus the surface covered at day 4. Data were subject to analysis of variance (ANOVA) followed by Dunnet's post test to test for differences among groups. Outgrowing cells were characterized by double-labelling with monoclonal vWF antibody (1:100, Dako) and polyclonal CD36 (1:100, Santa Cruz) after acetone fixation using their respective alexa coupled secondary antibodies.

Inhibition of Choroidal Neovascularisation In Vivo Using the Laser Injury Model

The standard model of choroidal neovascularisation is the laser injury induced neovascularisation (47). In this model, which is applicable to rodents and primates, a laser beam is used to disrupt the RPE and the Bruchs membrane that separates the choroidal vasculature from the subretinal space. The following local inflammatory reaction in deep retina and choroid leads to a localized subretinal neovascularisation in a similar manner as that observed in AMD. This local neovascularisation can be quantified on flatmounts of RPE/choroid/sclera. The antiangiogenic effect of DBG178 on subretinal neovascularisation was tested by injecting intravitreally at effective concentration of $10^{-7}$ to $10^{-6}$M within the eye and compared to that of intravitreal injection of saline used as a control.

FIG. 2 illustrates choroidal vessels detected using FITC-conjugated dextran infusion following laser-induced posterior retinal injury in eyes from 10-week-old male C57BL/6 mice and CD36 deficient mice of the same background with or without intravitreal treatment with DBG178 (FIG. 2a). Histograms of the surfaces of neovascular vessels obtained from C57BL/6 (CD36$_{+/+}$) and CD36 null (CD36–/–) mice with (DBG) or without (Ctl) treatment with DBG178 are illustrated in FIG. 2b.

DBG 178 significantly inhibited the neovascular response by more than 50% as shown in FIG. 2a. In contrast, DBG 178 had no effect on the neovascular response in the eye of CD36 null mice, showing that its antiangiogenic effect is CD36 dependent. The CD36 null mice developed significantly less neovascularisation following laser injury as compared to C57BL/6 mice which contrasted with an expected exaggerated neovascularisation considering its role as the main TSP-1/2 receptor. On the other hand, interference with mechanisms of RPE phagocytosis expected in CD36 deficiency could impede RPE expression of angiogenic mediators such as COX-2 (50) leading to the diminished neovascularisation.

Methodology for Laser Induced Choroidal Neovascularisation

Ten-week old C56/B16+/+ and CD36 null mice of C57B1/6 background were anesthetized by intramuscular injection of ketamine (50 mg/kg) and xylazine (10 mg/kg). Pupils were fully dilated with 1% tropicamide. Coverslips positioned on the mouse cornea were used as a contact glass. Laser-coagulations were performed 1 to 2 disc diameters away from the papillae using an Argon laser (532 nm) mounted on a slit lamp (400 mW, 50 ms and 50 μm). 3 laser impacts were applied to each eye. At day 3 and day 7 1 μl of azapeptide derivative DBG 178 in 0.9% NaCl at $10^{-5}$M was injected into the vitreous using glass capillaries (ca. 60 gauge) and a microinjector. Each treatment group contained a minimum of 4 mice (8 eyes). At day 10 mice were perfused with Fluorescein Dextran at $10^{-6}$ M. Their eyes were enucleated, fixed in 4% PFA for 15 minutes at room temperature, sectioned at the limbus and the cornea and lens were discarded. The retinas were carefully peeled from the RPE/choroid/sclera. Retinas and choroids were fixed for additional 15 minutes in methanol at –20° C. and incubated with TRITC-conjugated *Griffonia simplicifolia* Lectin (Sigma-Aldrich). The RPE/choroids were radially incised, flatmounted and viewed using a fluorescence microscope (BX51; Olympus). CNV were measured on photographs using Scion image analysis software.

Table 3 below shows $IC_{50}$ values obtained from competition curves of azapeptide derivatives in covalent photolabelling receptor assay using rat cardiac membranes as source of CD36 and the photoactivatable hexarelin derivative [$^{125}$I] Tyr-Bpa-Ala-hexarelin as radioligand.

TABLE 3

Binding affinity of aza peptide derivatives towards CD36

| Aza peptide/ Compound No. | Structure | $IC_{50}$ |
|---|---|---|
| Hexareline | His-D-2-Me-Trp-Ala-Trp-D-Phe-Lys-NH$_2$ | $2.97 \times 10^{-6}$M |
| DBG253-1 | His-D-Trp-Ala-azaPhe-D-Phe-Lys-NH$_2$ | $1.34 \times 10^{-6}$M |

TABLE 3-continued

Binding affinity of aza peptide derivatives towards CD36

| Aza peptide/ Compound No. | Structure | $IC_{50}$ |
|---|---|---|
| DBG253-2 | His-D-Trp-Ala-azaLeu-D-Phe-Lys-NH$_2$ | $2.89 \times 10^{-3}$M |
| DBG253-3 | His-D-Trp-Ala-azaBip-D-Phe-Lys-NH$_2$ | $1.35 \times 10^{-5}$M |
| DBG253-4 | His-D-Trp-Ala-azaCha-D-Phe-Lys-NH$_2$ | $2.10 \times 10^{-3}$M |
| DBG253-5 | His-D-Trp-Ala-azahomoPhe-D-Phe-Lys-NH$_2$ | $\gg 10^{-5}$M |
| DBG253-6 | His-D-Trp-Ala-azaNal-1-D-Phe-Lys-NH$_2$ | $3.62 \times 10^{-5}$M |
| DBG253-7 | His-D-Trp-Ala-Tyr-D-Phe-Lys-NH$_2$ | $1.32 \times 10^{-5}$M |
| DBG253-8 | His-D-Trp-Ala-D-Tyr-D-Phe-Lys-NH$_2$ | $1.20 \times 10^{-5}$M |
| DBG253-9 | (D/L)-His-azaPhe-Ala-Trp-D-Phe-Lys-NH$_2$ | $7.24 \times 10^{-5}$M |
| DBG253-10 | (D/L)-His-azaNal-1-Ala-Trp-D-Phe-Lys-NH$_2$ | $1.93 \times 10^{-3}$M |
| DBG253-11 | (D/L)-His-azahomoPhe-Ala-Trp-D-Phe-Lys-NH$_2$ | $3.68 \times 10^{-5}$M |
| DBG253-12 | (D/L)-His-azaBip-Ala-Trp-D-Phe-Lys-NH$_2$ | $2.32 \times 10^{-5}$M |
| DBG253-13 | (D/L)-His-azaCha-Ala-Trp-D-Phe-Lys-NH$_2$ | $\gg 10^{-5}$M |
| DBG201-A | His-D-Trp-azaLeu-Trp-D-Phe-Lys-NH$_2$ | $2.89 \times 10^{-6}$M |
| DBG175p | (D/L)His-azaTyr-Ala-Trp-D-Phe-Lys-NH$_2$ | $1.80 \times 10^{-6}$M |
| DBG178p | His-D-Trp-Ala-azaTyr-D-Phe-Lys-NH$_2$ | $2.80 \times 10^{-5}$M |
| DBG188p | His-D-Trp-azaGly-Trp-D-Phe-Lys-NH2 | $9.61 \times 10^{-6}$M |

Table 4 below shows $IC_{50}$ values obtained from competition curves of azapeptide derivatives of GHRP-6 in GHS-R1a radioreceptor assay using LLCPK-1 membranes overexpressing GSH-R1a and radioiodinated (1-28) rat ghrelin as tracer.

TABLE 4

| Azapeptide | EC50 |
|---|---|
| DBG145 | $8.09 \times 10^{-7}$M |
| DBG168-8 | $5.14 \times 10^{-7}$M |
| DBG175p | $8.53 \times 10^{-6}$M |
| DBG178p | $1.57 \times 10^{-5}$M |
| DBG188p | $8.08 \times 10^{-7}$M |
| DBG253-1 | $2.77 \times 10^{-6}$M |
| DBG253-2 | $1.95 \times 10^{-5}$M |
| DBG253-3 | $1.34 \times 10^{-6}$M |
| DBG253-4 | $4.28 \times 10^{-6}$M |
| DBG253-5 | $3.74 \times 10^{-6}$M |
| DBG253-6 | $7.23 \times 10^{-7}$M |
| DBG253-7 | $7.71 \times 10^{-7}$M |
| DBG253-8 | $3.25 \times 10^{-6}$M |
| DBG253-9 | $1.61 \times 10^{-5}$M |
| DBG253-10 | $4.65 \times 10^{-7}$M |
| DBG253-11 | $7.29 \times 10^{-7}$ |
| DBG253-12 | $1.64 \times 10^{-6}$M |
| DBG253-13 | $5.49 \times 10^{-6}$M |
| DBG201-A | $1.20 \times 10^{-6}$M |
| Ghreline, rat | $2.84 \times 10^{-10}$M |
| GHRP-6 | $3.65 \times 10^{-9}$M |

Tables 5 and 6 show the binding affinity of compound numbers 39-65 towards GS-R1a and CD36. The reference standard is GHRP-6 for the ghrelin receptor R1a and hexarelin which is the methylated form of GHRP 6 with the methyl Trp residue in position 2. The methodology used for the GHS-R1a and CD36 binding studies was as previously described.

TABLE 5

| Entry/Item No. | Cpd No. | Formula | IC$_{50}$ Binding GHS-R1a |
|---|---|---|---|
|  | GHRP-6 | His-D-Trp-Ala-Trp-D-Phe-Lys-NH$_2$ | 6.08 × 10$^{-9}$M |
|  | Hexareline | His-D-2-Me-Trp-Ala-Trp-D-Phe-Lys-NH$_2$ |  |
| 39 | CP-1A (i) |  | 5.10 × 10$^{-5}$M |
| 56 | CP-2B (v) | Ala-D-Trp-azaLeu-Trp-D-Phe-Lys-NH$_2$ | 1.12 × 10$^{-5}$M |
| 41 | CP-1A (iii) | (D/L)His-AzaPhe-Ala-Ala-D-Phe-Lys-NH$_2$ | >>10$^{-5}$M |
| 42 | CP-1A (iv) | Ala-AzaPhe-Ala-Trp-D-Phe-Lys-NH$_2$ | >>10$^{-5}$M |
| 43 | CP-1B (i) | His-AzaTyr-Ala-Trp-D-Phe-Ala-NH$_2$ | >>10$^{-5}$M |
| 44 | CP-1B (ii) | His-AzaTyr-Ala-Trp-D-Ala-Lys-NH$_2$ | >>10$^{-5}$M |
| 46 | CP-1B (iv) | Ala-AzaTyr-Ala-Trp-D-Phe-Lys-NH$_2$ | >>10$^{-5}$M |
| 53 | CP-2B (ii) | His-D-Trp AzaLeu-Trp-Ala-Lys-NH$_2$ | >>10$^{-5}$M |
| 54 | CP-2B (iii) | His-D-Trp-AzaLeu-Ala-D-Phe-Lys-NH$_2$ | >>10$^{-5}$M |
| 52 | CP-2B (i) | His-D-Trp-AzaLeu-Trp-D-Phe-Ala-NH$_2$ | 8.17 × 10$^{-6}$M |
| 55 | CP-2B (iv) | His-D-Ala-AzaLeu-Trp-D-Phe-Lys-NH$_2$ | >>10$^{-5}$M |
| 56 | CP-2B (v) | Ala-D-Trp-AzaLeu-Trp-D-Phe-Lys-NH$_2$ | >>10$^{-5}$M |
| 59 | CP-3 (iii) | His-D-Ala-Ala-AzaPhe-D-Phe-Lys-NH$_2$ | >>10$^{-5}$M |
| 60 | CP-3 (iv) | Ala-D-Trp-Ala-AzaPhe-D-Phe-Lys-NH$_2$ | >>10$^{-5}$M |
| 61 | CP-AzaGly-Pro | His-D-Trp-AzaGly-Pro-D-Phe-Lys-NH$_2$ | >>10$^{-5}$M |
| 62 | CP-AP_4 | His-D-Trp-AzaPro-Trp-D-Ala-Lys-NH$_2$ | >>10$^{-5}$M |
| 39 | CP-1A (i) | His-AzaPhe-Ala-Trp-D-Phe-Ala-NH$_2$ | >>10$^{-5}$M |
| 40 | CP-1A (ii) | His-AzaPhe-Ala-Trp-D-Ala Lys-NH$_2$ | >>10$^{-5}$M |
| 45 | CP-1B (iii) | His-AzaTyr-Ala-Ala-D-Phe-Lys-NH$_2$ | >>10$^{-5}$M |
| 47 | CP-2A (i) | His-D-Trp-AzaGly-Trp-D-Phe-Ala-NH$_2$ | 4.50 × 10$^{-5}$M |
| 48 | CP-2A (ii) | His-D-Trp-AzaGly-Trp-D-Ala-Lys-NH$_2$ | >>10$^{-5}$M |
| 49 | CP-2A (iii) | His-D-Trp-AzaGly-Ala-D-Phe-Lys-NH$_2$ | >>10$^{-5}$M |
| 50 | CP-2A (iv) | His-D-Ala-AzaGly-Trp-D-Phe-Lys-NH$_2$ | >>10$^{-5}$M |
| 51 | CP-2A (v) | His-D-Trp-AzaGly-Trp-D-Phe-Lys-NH$_2$ | 5.68 × 10$^{-7}$M |
| 57 | CP-3 (i) | His-D-Trp-Ala-AzaPhe-D-Phe-Ala-NH$_2$ | >>10$^{-5}$M |
| 58 | CP-3 (ii) | His-D-Trp-Ala-AzaPhe-D-Ala-Lys-NH$_2$ | >>10$^{-5}$M |
| 64 | CP-AP-2 | His-D-Trp-Ala-Trp-AzaPro-Lys-NH$_2$ | >>10$^{-5}$M |
| 63 | CP-AP-3 | His-D-Trp-Ala-AzaPro-D-Phe-Lys-NH$_2$ | >>10$^{-5}$M |
| 65 | CP-AP-5 | His-AzaPro-Ala-Trp-D-Phe-Lys-NH$_2$ | >>10$^{-5}$M |
| 66 | ZS554-F29 | Phe-D-Trp-Ala-AzaTyr-D-Phe-Lys-NH$_2$ | >>10$^{-5}$M |
| 67 | ZS555-F40 | Ala-D-Trp-Ala-AzaTyr-D-Phe-Lys-NH$_2$ | >>10$^{-5}$M |
| 68 | ZS556 | Hydrocinnamic acid-D-Trp-Ala-AzaTyr-D-Phe-Lys-NH$_2$ | >>10$^{-5}$M |

TABLE 6

| Item No./Entry No. | Cpd. No. | Formula | IC$_{50}$ Binding CD36 |
|---|---|---|---|
|  | GHRP-6 | His-D-Trp-Ala-Trp-D-Phe-Lys-NH$_2$ |  |
|  | Hexareline | His-D-2-Me-Trp-Ala-Trp-D-Phe-Lys-NH$_2$ | 3.33 × 10$^{-6}$M |
| 39 | CP-1A (i) |  | >>10$^{-5}$M |
| 56 | CP-2B (v) | Ala-D-Trp-azaLeu-Trp-D-Phe-Lys-NH$_2$ | 3.68 × 10$^{-6}$M |
| 41 | CP-1A (iii) | (D/L)His-AzaPhe-Ala-Ala-D-Phe-Lys-NH$_2$ | 2.76 × 10$^{-5}$M |
| 42 | CP-1A (iv) | Ala-AzaPhe-Ala-Trp-D-Phe-Lys-NH$_2$ | 5.02 × 10$^{-6}$M |
| 43 | CP-1B (i) | His-AzaTyr-Ala-Trp-D-Phe-Ala-NH$_2$ | 7.22 × 10$^{-5}$M |
| 44 | CP-1B (ii) | His-AzaTyr-Ala-Trp-D-Ala-Lys-NH$_2$ | >>10$^{-5}$M |
| 46 | CP-1B (iv) | Ala-AzaTyr-Ala-Trp-D-Phe-Lys-NH$_2$ | 1.74 × 10$^{-5}$M |
| 53 | CP-2B (ii) | His-D-Trp-AzaLeu-Trp-D-Ala-Lys-NH$_2$ | 4.94 × 10$^{-6}$M |
| 54 | CP-2B (iii) | His-D-Trp-AzaLeu-Ala-D-Phe-Lys-NH$_2$ | 9.66 × 10$^{-6}$M |
| 52 | CP-2B (i) | His-D-Trp-AzaLeu-Trp-D-Phe-Ala-NH$_2$ | 9.02 × 10$^{-6}$M |
| 51 | CP-2A (v) | His-D-Trp-AzaGly-Trp-D-Phe-Lys-NH$_2$ | 8.76 × 10$^{-6}$M |
| 64 | CP-AP-2 | His-D-Trp-Ala-Trp-AzaPro-Lys-NH$_2$ | >>10$^{-5}$M |
| 63 | CP-AP-3 | His-D-Trp-Ala-AzaPro-D-Phe-Lys-NH$_2$ | >>10$^{-5}$M |
| 66 | ZS554-F29 | Phe-D-Trp-Ala-AzaTyr-D-Phe-Lys-NH$_2$ | 1.18 × 10$^{-5}$M |
| 67 | ZS555-F40 | Ala-D-Trp-Ala-AzaTyr-D-Phe-Lys-NH$_2$ | 2.95 × 10$^{-6}$M |
| 68 | ZS556 | Hydrocinnamyl-D-Trp-Ala-AzaTyr-D-Phe-Lys-NH$_2$ | 3.25 × 10$^{-5}$M |

For azapeptides CP-2B(v) and CP-1A(iv), the modification of the structure of GHRP-6 decreased drastically the binding affinity towards R1a receptor without major change in the affinity to the CD36 receptor compared with hexarelin, the methylated derivative of GHRP6. The same was observed for CP-2B(ii) and ZS555-F40.

Alternative Azapeptides Synthesis Method

The present invention also extends to an alternative method of synthesizing azapeptides, as described below. A variety of methods have been developed for the introduction of aza-amino acids into peptides by solution-phase synthesis (49). Few strategies have, however, been reported for preparing aza-peptides on solid support and only recently have aza-peptide libraries been synthesized. In preliminary attempts to make aza-peptides, the N-terminal amino group of a resin bound peptide was converted into an isocyanate or active carbamate and subsequently reacted with a suitable N'-alkyl fluoren-9-yl methyl carbazate. This strategy afforded the desired aza-peptide contaminated with significant amounts of hydantoin (50) and to avoid the latter, additional backbone amide protection was required (50b). Solution-made aza-tri or dipeptide fragments have been coupled to the N-terminus of resin-bound peptides (40, 51). Multiple synthetic steps were required to make N-(Boc)aza-dipeptides, that have served as configurationally stable building blocks for Boc/Bzl solid-phase peptide synthesis (40). In the first effective Fmoc-strategy for solid-phase aza-peptide synthesis, the reaction of N-Fmoc protected aza-amino acid chlorides onto the growing chain of a resin-bound peptide has provided access to a variety of aza-peptide analogs (39). This procedure consists of solution-phase synthesis of N'-substituted fluorenylmethyl carbazates by reductive amination, followed by activation to the N-Fmoc-aza-amino acid chloride and coupling to the resin bound peptide.

Aza-amino scanning would constitute an effective means for identifying the importance of turn structure for activity in native peptides. The use of Fmoc-aza-amino acid chlorides has realized itself as a more general and efficient procedure for the solid-phase preparation of aza-peptides and in determining their structure-activity relationships against biological targets (41). However, this methodology has not been without its limitations; in particular, the scope of N'-substituted fluorenylmethyl carbazates is constrained by the prerequisite of a solution-phase synthesis of the N-substituted carbazates. The narrow range of functionalized aldehydes that may be amenable to reductive amination procedures has created a desire for alternative processes for adding the side-chain onto the aza-amino acid residue.

Currently, most synthetic routes to modify peptides incorporate the individually prepared un-natural amino acid residue by conventional solid phase peptide synthesis (SPPS) (52). A more direct and flexible method for the preparation of peptidomimetics would be to build the new side-chains onto the growing peptide strand during the peptide synthesis (53). Aza-peptides possess one or more aza-amino acid residues in which the α-carbon is substituted for a nitrogen atom. In contrast to the enantioselective synthesis of natural amino acid residues, the carbon-nitrogen bond forming reaction for aza-amino acid residues does not require stereo-chemical control. Selective introduction of the side-chain at the α-nitrogen of an aza-peptide does demand chemo-selective alkylation and chain extension reactions at an aza-glycine residue in the growing peptide chain on resin. In the present novel approach, activated aza-glycine residues are incorporated into the peptide chain by treating arylhydrazones with a phosgene equivalent such as p-nitrophenyl chloroformate and acylation of support-bound peptides and amino acids to form the respective N-terminal semicarbazones. Alkylation of the semicarbazone may then be achieved regio-selectively to introduce varying side-chain groups. This regio-selective carbon-nitrogen bond forming sequence for the synthesis of structurally diverse aza-peptides followed a three-step procedure inserted into a conventional solid-phase peptide synthesis (SPPS) cycle: (FIG. 5, reactions in box), activation (A), alkylation (B), and semicarbazone deprotection (C), followed by the normal SPPS sequence involving coupling (D), deprotection and cleavage from the support (E). Following step C in the loop a number of options are possible, including repeating the steps in the synthesis cycle to add another unnatural residue to the growing peptide chain, coupling a natural amino acid or other residue via normal solid-phase methodology, or protecting the free amino group subsequent to other reactions on the resin-bound product.

The present analysis was initiated with conventional SPPS of a known dipeptide [D-Phe-Lys] and tripeptide [Trp-D-Phe-Lys], which constitute the start sequence of a member of the growth hormone releasing peptide family namely, GHRP-6 (His-D-Trp-Ala-Trp-D-Phe-Lys-NH$_2$). This hexapeptide acts at the growth hormone secretagogue and stimulates the release of growth hormones from the pituitary (54, 55). Syntheses were conducted on a hydrophilic NovaPEG Rink Amide Resin™ which displayed excellent swelling properties in polar protic solvents, including water and MeOH (56).

Figure 4:
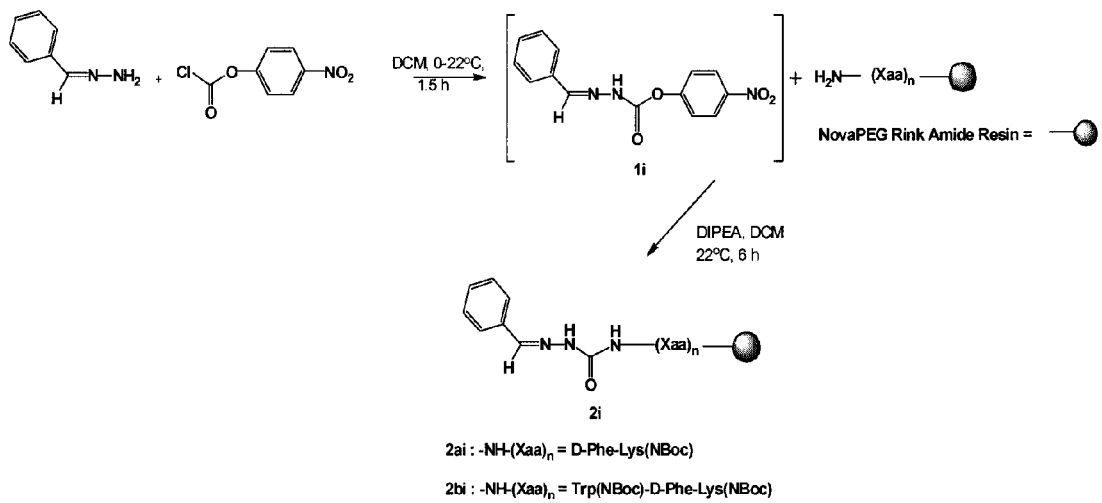
FIG. 4 illustrates a general scheme for the activation and coupling of intermediate 1i to the N-terminus of the peptide bound resin to form semicarbazone 2ai and 2bi, the synthesis being performed on NovaPEG Rink Amide Resin™.

Phenyl hydrazone was prepared on condensation of benzaldehyde and hydrazine hydrate. Treatment of phenyl hydrazone with p-nitrophenyl chloroformate (57), provides the imine protected activated aza-glycine intermediate for coupling to the N-terminus of the peptide bound resin. Other reagents such as phosgene (39) and carbonyldiimidazole (58), which have previously been used in solution for the synthesis of aza-peptides, instead, gave the symmetric urea from reaction with two equivalents of hydrazone. The acylation of the resin-bound peptide was efficiently monitored by LCMS analysis after deprotection and cleavage of peptide from a small aliquot (3 mg) of resin with a freshly made TFA/TES/H$_2$O (95:2.5:2.5, v/v/v) solution. This indicated complete conversion of the starting material to the resin-bound semicarbazone peptide 2i (FIG. 4)

Figure 5:
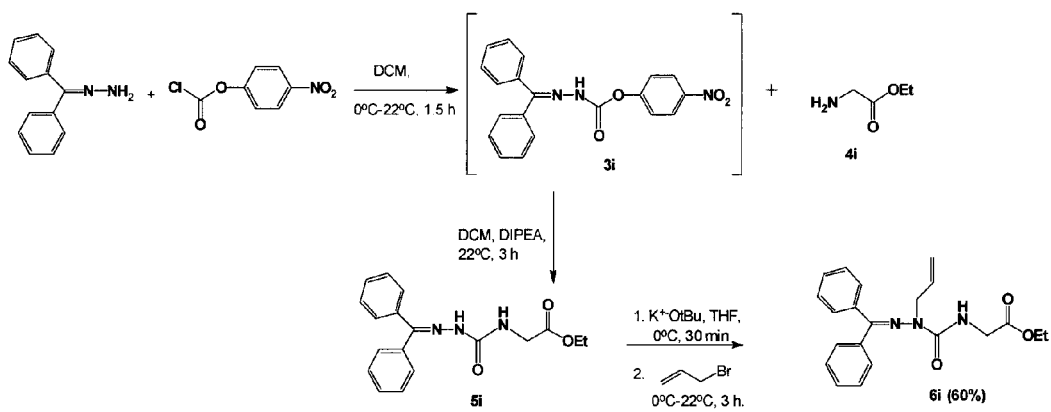
FIG. 5 illustrates a solution-phase synthesis of benzophenone semicarbazone aza-Gly-Gly dipeptide 5i and regio-selective mono-alkylation to yield benzophenone semicarbazone aza-(allyl)Gly-Gly dipeptide 6i.

In analogy to the carbon-nitrogen double bond resonance stabilizing the alpha-carbanion of a glycine Shiff-base in the synthesis of α-substituted amino acid analogs (59), the semicarbazone was expected to favor deprotonation and alkylation of aza-glycine 2i. In semicarbazone 2i, the proton on the hydrazone nitrogen is made sufficiently acidic such that basic conditions may be used to effect regio-selective deprotonation for alkylation reactions (60). The regio-selective deprotonation and alkylation reactions were first tried in-solution using the benzophenone semicarbazone, aza-glycinyl-glycine ethyl ester 5i, which was derived from activation of the hydrazone from bezophenone using p-nitrophenyl chloroformate and acylation of glycine ethyl ester (FIG. 5). Semicarbazone 5i (100 mol %) was treated with potassium t-butoxide (120 mol %) as base and allyl bromide (120 mol %) as electrophile to yield 60% of a single allylated product, benzophenone semicarbazone aza-(allyl)Gly-Gly-OEt 6i, for which the $^1$H-$^1$H COSY NMR spectrum indicated a coupling cross-peak between the amide NH and the glycine methylene protons, as evidence of the regio-selective mono-alkylation reaction.

Figure 6:
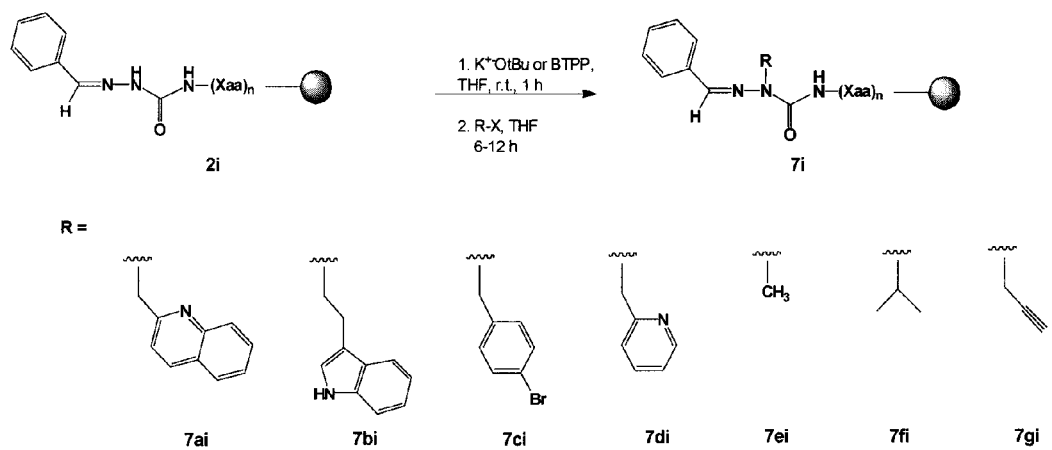
FIG. 6 illustrates a general scheme for the alkylation reaction of FIG. 3.

On solid support, benzaldehyde semicarbazone 2i proved efficient in alkylations using potassium t-butoxide (300 mol %) and various electrophiles (300 mol %) to give monoalkylated products 7ai-7gi (FIG. 6) as characterized by their analytical LCMS traces after cleavage of a small aliquot of peptide from the resin. In the case of 7ai and 7di, the hydrochlorides required an additional equivalent of base in the reaction mixture to effect neutralization of the salt. In the case of product 7bi, the alkylation reaction was found to be sluggish with potassium t-butoxide as base favoring only 20% conversion. However, the stronger organic soluble non-ionic phosphazene (Schwesinger) base (61), tert-butylimino-tri(pyrrolidino)phosphorane (BTPP) gave 85% conversion to the alkylated product 7bi. In the case of the more sterically encumbered secondary alkyl halides, with postassium t-butoxide as base, isopropyl bromide failed to react; however, alkylation proceeded cleanly with isopropyl iodide, resulting in complete conversion to the aza-valine analog 7fi.

Figure 7:
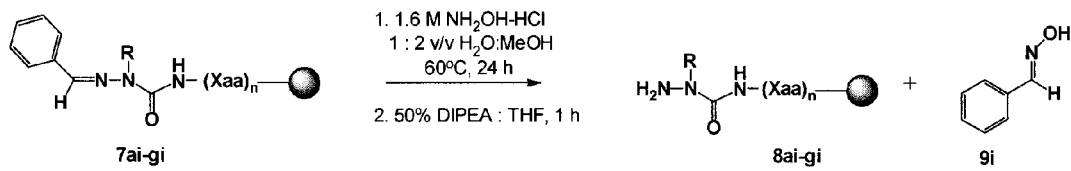
FIG. 7 illustrates a general scheme for the deprotection reaction of FIG. 3.

Hydrazones have been used as chiral auxiliaries in organic processes related to the enantioselective carbonyl group transformations (62). They are easily introduced, chemically robust and tolerant to a high degree of functionality. Their removal has, however, necessitated use of harsh conditions, i.e., strong acid, oxidative and reductive cleavage conditions to release the hydrazide moiety, sometimes in a modified form (63). Some of the milder deprotection conditions associated with acid catalyzed hydrolysis (64) and Lewis-acid promoted dithioketalization (65) favor the release of the free hydrazide moiety. Since Fmoc SPPS methodology is regarded as an acid sensitive strategy, due to the employment of the acid-labile Rink amide linker and side-chain protecting groups, milder methods were developed for the incorporation and removal of the semicarbazone group under essentially neutral conditions. Preliminary trials were conducted on a Rink amide linker polystyrene based resin. Acid catalyzed hydrolysis reactions and Lewis-acid promoted dithioketalization deprotection, both resulted in partial to complete release of the semicarbazone with concomitant removal of side-chain protecting groups from the peptide-bound resin and formation of side-products. Conversely, a mild hydrolysis procedure has been described for the removal of imine-protecting groups from the peptide bound resin (53), employing aqueous NH$_2$OH—HCl, THF, pH=6, followed by free-basing with diisopropylethylamine (DIPEA). In our hands, no solvolysis of semicarbazone 7i was observed to occur under these identical conditions on a hydrophobic polystyrene based resin; however, when the more hydrophilic NovaPEG Rink Amide Resin™ was employed, the resin swelled in the hydrolytic solvent conditions favoring deprotection (66). Complete liberation of semicarbazides 8ai-8gi, from semicarbazones 7ai-7gi, was accomplished using elevated temperatures (60° C., FIG. 7) as determined by their analytical LCMS traces obtained after cleavage of a small aliquot of peptide from the resin. The reaction also produced benzaldehyde oxime (9i) as by-product, indicating that the reaction occurred by imine exchange and not hydrolysis.

Figure 8:
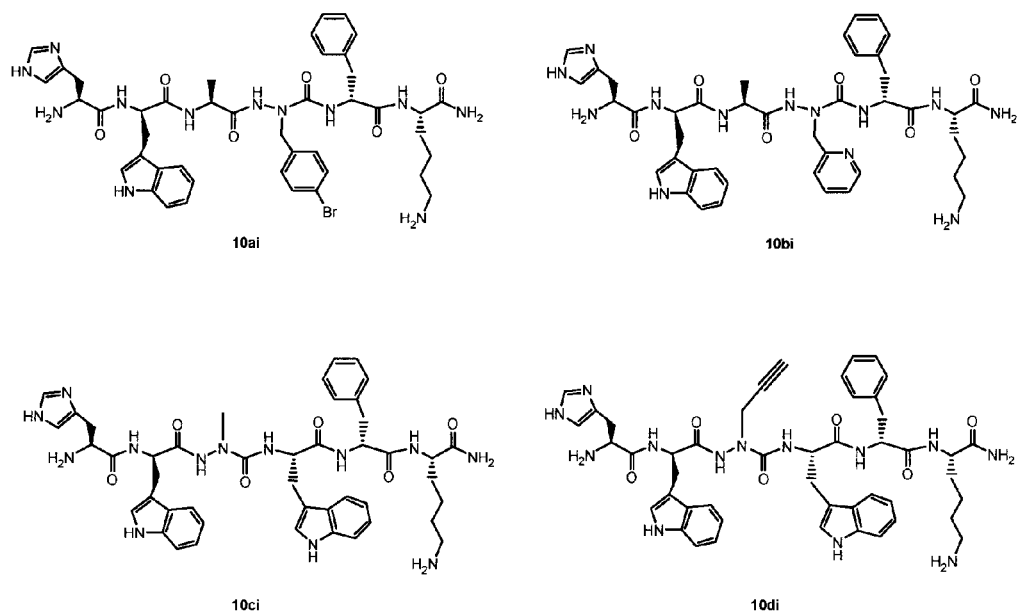
FIG. 8 illustrates an example of the azapeptides synthesized by the method of FIG. 3.

Acylation of the aza-amino acid residue was performed as described in the literature (51), by treatment of the resin swollen in THF with a 6-fold excess of Fmoc-amino acid chloride, generated in situ with bis-(trichloromethyl)-carbonate (BTC) (67) and 2,4,6-collidine. Aza-peptides were analyzed by LCMS, which indicated a crude-purity ranging from 40-60% of the desired acylated products. Aza-peptide syntheses were then continued by the conventional SPPS (68). Final cleavage of aza-peptides from the support and deprotection of side-chain protecting groups were performed by treating the resin with a freshly made TFA/TES/H$_2$O (95:2.5: 2.5, v/v/v) solution. Aza-peptides (Table 6) were isolated after evaporation, dissolved in a 1:1 acetonitrile/H$_2$O solution, and lyophilized to white foams that were directly analyzed by LCMS to assess a crude purity ranging from 8-20%. These were subsequently purified to determine the pure yield recovery (FIG. 8).

TABLE 7

Yields and Purities of isolated Azapeptides.

| Compound | T$_R$ (min) in ACN[a] | T$_R$ (min) in MEOH | HPLC purity at 214 nm[b] | Yield (%)[c] | Expected Mass | Mass[d] |
|---|---|---|---|---|---|---|
| 10ai | 13.76 | 17.38 | 94.8% | 6.53 | 913.86 | 913.5, 916.2[e] |
| 10bi | 10.03 | n/a | 36.2% | 2.62 | 835.95 | 836.4 |
| 10ci | 10.84 | 13.86 | 92.8% | 3.44 | 874 | 874.4 |
| 10di | 9.45 | 10.82 | 95.4% | 3.33 | 898.02 | 900.4 |

[a]Unless otherwise noted, analytical HPLC analyses were performed on a 5 μM 150 mm × 4.6 mm C18 Gemini column with a flow rate of 0.5 ml/min using a 0-40 gradient from water (0.1% FA) to CH$_3$CN (0.1% FA) or MeOH (0.1% FA).
[b]HPLC purity at 214 nm of the purified peptide.
[c]Yields after purification by HPLC are based on manufacturer's reported loading for Rink resin.
[d]Observed masses corresponding to the H$^+$ adducts.
[e]Presence of Br yields 50:50 ratio of M$^+$ and M + 2 isotopes.

These preliminary studies demonstrate that the submonomer approach can be utilized to convert resin-bound amino acids or peptides to unnatural aza-peptide derivatives. The mild reagents and conditions used are compatible with Fmoc based SPPS strategies. A more structurally diverse group of novel aza-peptides are now accessible using this technique. Therefore, this method can be readily applicable to aza-amino scanning and identifying the importance of turn structure for activity in native peptides and in determining their structure-activity relationships against biological targets. Furthermore this method may prove effective for synthesizing libraries of aza-peptides by combinatorial methods such as IRORI kan technology.

General Methods.

NovaPEG™ Rink Amide resin (0.67 mmol/g) was purchased from NovaBiochem® Inc., and the manufacturer's reported loading of the resin was used in the calculation of the yields of the final products. Reagents such as benzaldehyde, p-nitrobenzyl chloroformate, potassium t-butoxide, tert-butylimino-tri(pyrrolidino)phosphorane (BTPP), 2-(chloromethyl)quinoline hydrochloride, 4-bromobenzyl bromide, 2-(chloromethyl)pyridine hydrochloride, iodomethane, 2-iodopropane, 80% propargyl bromide in toluene and hydroxylamine hydrochloride were purchased from Aldrich and used directly. The alkylating reagent, 3-(2-bromoethyl) indole was also purchased from Aldrich, but protected as the N-Boc analogue as described in the literature (69) prior to the alkylation reaction. $^1$H and $^{13}$C NMR spectra were recorded, respectively, at 400 and 100 MHz in CDCl$_3$ as the solvent and tetramethylsilane internal reference. Thin-layer chromatography was performed on silica gel 60 F254 plates from Merck™. Flash chromatography was performed on silica gel 60 (230-400 Mesh ASTM) from Merck™. Commercially available Fmoc amino acids and HBTU were purchased from GL Biochem™ and used as received. Solvents for reactions were dried and distilled prior to use. Analytical LCMS and HPLC analyses were performed on either a 5 μM, 150 or 50 mm×4.6 mm C18 Phenomenex Gemini Column™ with a flow rate of 0.5 ml/min using either a 20-80% or a 0-40% gradient from water (0.1% FA) to CH$_3$CN (0.1% FA) or MeOH (0.1% FA). Aza-peptides 10ai-di were purified on a semi-preparative column (5 μM, 250 mm×21.2 mm, C18 Gemini Column™) using a 2-40% gradient from water (0.1% FA) to CH$_3$CN (0.1% FA) with a flow rate of 10.6 ml/min.

Benzophenone Semicarbazone Aza-Glycinyl-Glycine Ethyl Ester, 5i,

Benzophenone hydrazone (500 mg, 2.5 mmol) in DCM (5 mL) was added dropwise over 15 min to a solution of p-nitrobenzyl chloroformate (600 mg, 3 mmol) in DCM (5 mL) at 0° C. The reaction mixture was stirred at room temperature under argon for an additional 1.5 h, until TLC, [(2:1 Hex: EtOAc), Rf (benzophenone hydrazone): 0.45 and Rf (3i): 0.7] indicated complete consumption of the starting material. To this mixture was added dropwise DIPEA (400 μL, 4.6 mmol) and the suspension was stirred for an additional 3 h at room temperature, (22° C.) under argon. The reaction mixture was diluted in DCM (60 mL) and extracted several times with NaHCO$_3$ (8×30 mL). The organic phase was dried over MgSO$_4$, concentrated in-vacuo and purified by flash chromatography using 2:1 Hexane:EtOAc [Rf (5i): 0.25] to yield a white solid (0.5 g, 60%). $^1$H NMR (CDCl$_3$) δ: 1.19 (t, J=7 Hz, 3H), 4.02 (d, J=5.6 Hz, 2H), 4.13 (q, J=7 Hz, 2H), 6.78 (t, J=5.5 Hz, 1H), 7.1-7.4 (m, 10H), 7.61 (s, 1H); $^{13}$C NMR (CDCl$_3$) δ: 13.8, 41.4, 61.0, 126.8, 127.8, 127.9, 128.1, 129.0, 129.1, 129.36, 129.43, 129.5, 131.4, 136.5, 148.2, 151.0, 154.9, 170.0; LCMS (ESI) Calcd. for C$_{18}$H$_{19}$N$_3$O$_3$, M$^+$: 325.4. Found (M+H)$^+$326.

Benzophenone Semicarbazone Aza-Allylglycinyl-Glycine Ethyl Ester, 6i,

To a solution of semicarbazone 5i, (50 mg, 0.15 mmol) in THF (0.5 mL), potassium t-butoxide (25 mg, 0.18 mmol) was added at 0° C. under argon. The reaction mixture was stirred for 1 h, treated drop-wise with allyl bromide (20 μL, 0.18 mmol), stirred for 3 h at room temperature (22° C.) under argon, diluted in Et$_2$O (5 mL) and extracted with NaHCO$_3$ (2×2 mL) and brine (2×2 mL). The organic phase was dried over MgSO$_4$, concentrated in-vacuo and purified by flash chromatography using 2:1 Hexane:EtOAc [Rf (6i): 0.45] to yield a an oil (35 mg, 60%). $^1$H NMR (CDCl$_3$) δ: 1.23 (t, J=7 Hz, 3H), 3.86 (dd, J=1.6 Hz, 3.8 Hz, 2H), 4.05 (d, J=5.7 Hz, 2H), 4.16 (q, J=7 Hz, 2H), 4.78 (dd, J=1 Hz, 10 Hz, 1H), 4.92 (dd, J=1 Hz, 10 Hz, 1H) 5.33-5.43 (m, 1H), 6.89 (t, J=5.5 Hz, 1H), 7.18-7.42 (m, 10H); $^{13}$C NMR (CDCl$_3$) δ: 13.8, 42.2, 47.9, 60.8, 116.3, 127.8, 128.2, 128.3, 128.7, 129.3, 129.6, 132.4, 135.6, 138.4, 157.7, 158.4, 170.2; LCMS (ESI) Calcd. for C$_{21}$H$_{23}$N$_3$O$_3$, M$^+$: 365.4. Found (M+H)$^+$366.1.

General Procedure for Peptide Synthesis, Fmoc Deprotection and HBTU Couplings.

Peptide syntheses were performed under standard conditions (70) on an automated shaker using NovaPEG™ Rink Amide resin (0.67 mmol/g). Couplings of amino acids (3 equiv) were performed in DMF using HBTU (3 equiv) as coupling reagent and DIPEA (6 equiv). Fmoc deprotections were performed by treating the resin with 20% piperidine in DMF for periods of 10 and 20 min. Resin was washed after each coupling and deprotection step sequentially with DMF (2×10 mL), MeOH (2×10 mL), EtOH (2×10 mL), THF (2×10 mL), Et$_2$O (2×10 mL) and DCM (2×10 mL). The coupling steps were monitored to completion by the Kaiser (70) test.

General Procedure for the Preparation of Benzladehyde Semicarbazone Peptide Resin 2i To a stirred solution of EtOH (1.5 mL) and hydrazine hydrate (60 μL, 1.8 mmol) at 0° C., benzaldehyde (60 μL, 0.6 mmol) was added dropwise to generate the phenyl hydrazone.

The reaction was stirred to completion which was usually after 15 min as indicated by TLC, [(2:1 Hex:EtOAc), Rf (benzaldehyde): 0.7 and Rf (benzaldehyde hydrazone): 0.6], and poured directly into H$_2$O (5 mL) and extracted in DCM (3×5 mL). The organic phase was dried with MgSO$_4$ and concentrated in-vacuo to yield the benzaldehyde hydrazone as a yellow-tinged oil that was employed directly without further purification.

Benzaldehyde hydrazone (70 mg, 0.6 mmol, 3 equiv.) in DCM (1 mL) was added dropwise over 15 min to a solution of p-nitrobenzyl chloroformate (125 mg, 0.61 mmol, 3.2 equiv.) in DCM (1 mL) at 0° C. The reaction mixture was stirred at room temperature under argon for an additional 1.5 h, until TLC, [(2:1 Hexane:EtOAc), Rf (benzaldehyde hydrazone): 0.6 and Rf (1i): 0.75] indicated complete consumption of the starting material. To this mixture was added dropwise DIPEA (210 µL, 1.2 mmol, 6 equiv.) and the suspension was quickly transferred to the resin. The reaction was mixed on an automated shaker for 6 h at room temperature. The resin was filtered and washed under vacuum with DMF (2×10 mL), MeOH (2×10 mL), EtOH (2×10 mL), THF (2×10 mL), Et$_2$O (2×10 mL) and DCM (2×10 mL). The extent of reaction conversion was monitored on an aliquot (3 mg) of resin which was subjected to 1 mL of TFA/TES/H$_2$O (95:2.5:2.5, v/v/v) for resin cleavage and the crude was analyzed by LCMS.

Benzaldehyde semicarbazone
Aza-Gly-D-Phe-Lys-NH$_2$ (2ai)

Tr=3.77 min; LCMS (ESI) calcd for C$_{23}$H$_{30}$N$_6$O$_3$ (M+2H)$^+$, 440.6. Found m/e 441.3 (M+2H)$^+$ Benzaldehyde semicarbazone
Aza-Gly-Trp-D-Phe-Lys-NH$_2$ (2bi)

Tr=4.38 min; LCMS (ESI) calcd for C$_{27}$H$_{36}$N$_8$O$_4$ (M+2H)$^+$, 626.7. Found m/e 627.4 (M+2H)$^+$ General Procedure for the Synthesis of Mono-Alkylated Benzaldehyde Semicarbazone Peptide Resin 7i To the swollen benzaldehyde semicarbazone peptide bound resin 2i (0.1 g, 67 µmol) in THF (2 mL), potassium t-butoxide (25 mg, 0.2 mmol, 3 equiv.) or BTPP (for the synthesis of 7bi, 60 µL, 0.2 mmol, 3 equiv.) was added. The mixture was agitated on an automated shaker for 1 h, treated with the electrophile, R-X (0.2 mmol, 3 equiv.) and agitated on the shaker at room temperature for an additional 12 h. The resin was filtered and washed under vacuum with DMF (2×10 mL), MeOH (2×10 mL), EtOH (2×10 mL), THF (2×10 mL), Et$_2$O (2×10 mL) and DCM (2×10 mL). The extent of reaction was monitored by subjecting an aliquot (3 mg) of resin to cleavage [1 mL, TFA/TES/H$_2$O (95:2.5:2.5, v/v/v)] and analyzing the crude by LCMS.

Benzaldehyde semicarbazone Aza-(2-quinolinyl) Ala-D-Phe-Lys-NH$_2$ (7ai)

Tr=4.59 min; LCMS (ESI) calcd for C$_{33}$H$_{37}$N$_7$O$_3$ (M+H)$^+$, 579.7. Found m/e 580.3 (M+H)$^+$ Benzaldehyde semicarbazone Aza-(N-Boc-3-ethylindolyl)Gly-D-Phe-Lys-NH$_2$ (7bi)

Tr=4.52 min; LCMS (ESI) calcd for C$_{33}$H$_{39}$N$_7$O$_3$ (M+2H)$^+$, 581.8. Found m/e 584.4 (M+2H)$^+$ Benzaldehyde semicarbazone
Aza-(p-bromo)Phe-D-Phe-Lys-NH$_2$ (7ci)

Tr=4.70 min; LCMS (ESI) calcd for C$_{30}$H$_{35}$BrN$_6$O$_3$ (M+H)$^+$, 607.5. Found m/e 609.3 and 611.2 (M+H)$^+$ in a 1:1 ratio due to Br isotopes Benzaldehyde semicarbazone-Aza-(2-pyridyl)Ala-D-Phe-Lys-NH$_2$ (7di)

Tr=3.69 min; LCMS (ESI) calcd for C$_{29}$H$_{35}$N$_7$O$_3$ (M+H)$^+$, 530.6. Found m/e 530.3 (M+H)$^+$ Benzaldehyde semicarbazone-Aza-Ala-Trp-D-Phe-Lys-NH$_2$ (7ei)

Tr=4.56 min; LCMS (ESI) calcd for C$_{35}$H$_{42}$N$_8$O$_4$ (M+2H)$^+$, 640.9. Found m/e 641.4 (M+2H)$^+$ Benzaldehyde semicarbazone
Aza-Val-Trp-D-Phe-Lys-NH$_2$ (7fi)

Tr=4.58 min; LCMS (ESI) calcd for C$_{37}$H$_{46}$N$_8$O$_4$ (M+2H)$^+$, 668.9. Found m/e 669.4 (M+2H)$^+$ Benzaldehyde semicarbazone Aza-(propargyl)Gly-Trp-D-Phe-Lys-NH$_2$ (7gi)

Tr=4.51 min; LCMS (ESI) calcd for C$_{37}$H$_{42}$N$_8$O$_4$ (M+2H)$^+$, 664.9. Found m/e 665.4 (M+2H)$^+$ General Procedure for the Deprotection of the Benzaldehyde Semicarbazone Peptide Resin 7i Synthesis of Semicarbazido Peptide Resin 8ai-8gi Resin-bound semicarbazone 7ai-7gi (0.1 g, 67 µmol) was washed with MeOH and then MeOH:H$_2$O (2:1, 3×1.5-2 mL). A solution of 1.6 M NH$_2$OH—HCl in MeOH:H$_2$O (2:1 v/v) (1 mL) was added to the resin and the suspension was heated in an oil-bath at 60° C. for 24 h. The resin was filtered and washed under vacuum with DMF (2×10 mL), MeOH (2×10 mL), EtOH (2×10 mL), THF (2×10 mL), Et$_2$O (2×10 mL) and DCM (2×10 mL), and then neutralized with 50% DIEA:THF (2 mL) for 1 h. The resin was drained and washed as before and the extent of reaction was monitored by subjecting an aliquot (3 mg) of resin to the cleavage conditions [1 mL, TFA/TES/H$_2$O (95:2.5:2.5, v/v/v)] and analyzing the crude by LCMS.

Aza-(2-quinolinyl)Ala-D-Phe-Lys-NH$_2$ (8ai)

Tr=2.89 min; LCMS (ESI) calcd for C$_{26}$H$_{33}$N$_7$O$_3$ M$^+$, 491.6 and (M+Na)$^+$ 514.6. Found m/e 492.3 M$^+$ and (M+Na)$^+$ 514.4

Aza-(3-ethylindolyl)Gly-D-Phe-Lys-NH$_2$ (8bi)

Tr=3.99 and 2.82 min; LCMS (ESI) calcd for C$_{26}$H$_{35}$N$_7$O$_3$ M$^+$, 493.6. Found m/e 494.3 M$^+$ and 351.2 (M-3-ethylindole)$^+$ Aza-(p-bromo)Phe-D-Phe-Lys-NH$_2$ (8ci)

Tr=4.17 min; LCMS (ESI) calcd for C$_{23}$H$_{31}$BrN$_6$O$_3$M$^+$, 519.4. Found m/e 519.3 and 521.3, M$^+$ in a 1:1 ratio due to Br isotopes Aza-(2-pyridyl)Ala-D-Phe-Lys-NH$_2$ (8di)

Tr=2.88 min; LCMS (ESI) calcd for $C_{22}H_{31}N_7O_3$ M$^+$, 441.5. Found m/e 442.3 M$^+$ Aza-Ala-Trp-D-Phe-Lys-NH$_2$ (8ei)

Tr=3.76 min; LCMS (ESI) calcd for $C_{28}H_{38}N_8O_4$M$^+$, 550.6. Found m/e 551.4 M$^+$ Aza-Val-Trp-D-Phe-Lys-NH$_2$ (8fi)

Tr=4.10 min; LCMS (ESI) calcd for $C_{30}H_{42}N_8O_4$M$^+$, 578.7. Found m/e 579.4 (M+2H)$^+$ Aza-(propargyl)Gly-Trp-D-Phe-Lys-NH$_2$ (8gi)

Tr=3.95 min; LCMS (ESI) calcd for $C_{30}H_{38}N_8O_4$M$^+$, 574.7. Found m/e 575.4 M$^+$ General Procedure for Coupling of the Next Amino Acid to the Semicarbazido Peptide Resin 8i Semicarbazido peptide resin 8ai-8gi (0.1 g, 67 µmol) was swollen in dry THF (1 mL) and treated with a solution of Fmoc-amino acid (0.4 mmol, 6 equiv.) in THF (1 mL), followed sequentially by BTC (0.2 mmol, 3 equiv) and 2,4,6-collidine (2 mmol, 30 equiv.). The resin was filtered and washed under vacuum with DMF (2×10 mL), MeOH (2×10 mL), EtOH (2×10 mL), THF (2×10 mL), Et$_2$O (2×10 mL) and DCM (2×10 mL). The extent of reaction was monitored by subjecting an aliquot (3 mg) of resin to the cleavage conditions [1 mL, TFA/TES/H$_2$O (95:2.5:2.5, v/v/v)] and analyzing the crude by LCMS. The target sequences were completed according to the conventional SPPS.

General Procedure for Side Chain Deprotection and Aza-Peptide Cleavage.

Aza-peptide resin was treated with a freshly made solution of TFA/H$_2$O/TES (95:2.5:2.5, v/v/v, 20 mL/g of aza-peptide resin) for 2 h at room temperature. The cleavage mixture was filtered, and the resin was washed with neat TFA. The filtrate was then concentrated and dissolved in an acetonitrile/H$_2$O (1:1, v/v) solution and lyophilized to yield a light foam or powder. The aza-peptides 10ai-di were purified by preparative RP-HPLC using a semi-preparative column as described in the general section.

His-D-Trp-Ala-aza-(p-bromo)Phe-D-Phe-Lys-NH$_2$ (entry 69 in Table, 10ai in FIG. 8). Tr$_1$=13.76 min; Tr$_2$=17.38 min; LCMS (ESI) calcd for $C_{43}H_{53}BrN_{12}O_6$ M$^+$, 913.9. Found m/e 913.5 and 916.2, M$^+$ in a 1:1 ratio due to Br isotopes His-D-Trp-Ala-aza-(2-pyridyl)Ala-D-Phe-Lys-NH$_2$ (10bi).

Tr=10.03 min; LCMS (ESI) calcd for $C_{42}H_{53}N_{13}O_6$ M$^+$, 836.4. Found m/e 442.3 M$^+$ His-D-Trp-aza-Ala-Trp-D-Phe-Lys-NH$_2$ (entry 12 in Table, 10ci in FIG. 8). Tr$_1$=10.84 min; Tr$_2$=13.86 min; LCMS (ESI) calcd for $C_{45}H_{55}N_{13}O_6$M$^+$, 874. Found m/e 874.4 M$^+$ His-D-Trp-aza-(propargyl)Gly-Trp-D-Phe-Lys-NH$_2$ (entry 70 in Table, 10di such as beta-alanine, beta-homophenylalanine as well as longer chain amino acids such). Tr$_1$=9.45 min; Tr$_2$=10.82 min; LCMS (ESI) calcd for $C_{47}H_{54}N_{13}O_6$ (M+2)$^+$, 900. Found m/e 900.4 (M+2)$^+$.

REFERENCES

1. Klein R. Age related macular degeneration. Berger J W, Fine S L, and Macguir M G ed. 1999; 17-30. Mosby, st louis, Mo.
2. De Jong P. Age related macular degeneration. *New Engl. J. Med.* 2006: 355:1474-1485.
3. Rattner A, Nathans J. Macular degeneration: recent advances and therapeutic opportunities. *Nature Reviews Neuroscienc.* 2006; 7:860-872
4. Sarks S H. Ageing and degeneration in the macular region: a clinico-pathological study. *Brit J opthalmol* 1976; 60:324-341
5. Friedman E. The role of the atherosclerotic process in the pathogenesis of age-related macular degeneration. *Am J Opthalmol* 2000; 130: 658-663.
6. Vingerling J R, Dielemans I, Bots M I et al. Age-related macular degeneration is associated with atherosclerosis. The Rotterdam study. *Am J Epidemiol* 1995; 142: 404-409.
7. Green W R and Key N N. Senile macular degeneration: a histopathologic study. *Trans Am Opthalmol soc* 1977; 75: 180-254.
8. Ambati J, Ambati B K, Yoo S H et al. Age-related macular degeneration: etiology, pathogenesis, and therapeutic strategies. *Sury Opthalmo.* 2003; 48:2572-93
9. Shima D T, Adamis A P, Ferrara N et al. Hypoxic induction of endothelial cell growth factors in retinal cells: identification and characterization of vascular endothelial growth factor (VEGF) as the mitogen. *Mol Med* 1995; 1: 182-193.
10. Roth F, Bindewald A, Holz F G. Keypathophysiologic pathways in age-related macular disease. *Graefes Arch Clin Exp Opthalmo* 2004; 242:710-716
11. Campochiaro P A. Retinal and choroidal neovascularisation. *J cell Physiol* 2000; 97: 10242-10247.
12. Tolentino M J, Brucker A J, Fosnot J et al. Intravitreal injection of vascular endothelial growth factor small interfering RNA inhibits growth and leakage in a non human primate laser-induced model of choroidal neovascularisation. *Retina* 2004; 24:660
13. Shen J, Samul R, Silva R L et al. Suppression of ocular neovascularization with SiRNA targeting VEGF receptor. *Gene ther* 2005; 13:225-234
14. Wheelan J. First clinical data on RNAi. *Drug discov Today* 2005; 10:1014-15
15. Eye study group. Preclinical and phase 1A clinical evaluation of an anti-VEGF pegylated aptamer (EYE001) for the treatment of exudative age-related macular degeneration. *Retina* 2002; 22: 143-152.
16. Krzystolik M G, Afshari M A, Adamis A P et al. Prevention of experimental choroidal neovascularization with intravitreal anti-vascular endothelial growth factor antibody fragments. *Arch Opthalmol* 2002; 120: 338-346.
17. Hood J D, Cheresh D A. Building a better Trap. *Proc Natl Acad. Sci. USA* 2003; 100: 8624-8625.
18. Takeda A, Hata Y, Shiose S et al. Suppression of experimental choroidal neovascularization utilizing KDR selective receptor tyrosine kinase inhibitor. *Graefes Arch. Clin. exp. Opthalmol* 2003; 241:1122-1129.
19. Saishin Y, Silva R L, Callahan K et al. Periocular injection of microspheres containing PKC412 inhibits choroidal neovascularisation in a porcine model. *Invest. Opthalmol. Vis. Sci.* 2003; 44:4989-4993.
20. Ishibashi T, Miki K, Sorgente N et al. Effects of intravitreal administration of steroids on experimental subretinal neovascularization in the subhuman primate. *Arch Opthalmol* 1985; 103: 708-711.

21. Augustin A J, Schmidt Erfurth U. Verteporfin therapy combined with intravitreal triamcinolone in all types of choroidal neovascularisation due to age-related macular degeneration. *Opthalmology* 2006; 113:14-22
22. Jonas J B, Degenring R F, Kreissig I et al. Intraocular pressure elevation after intravitreal triamcinolone acetonide injection. *Opthalmology* 2005; 112: 593-598.
23. Slakter J S. Anecortave acetate as monotherapy for treatment of subfoveal neovascularisation in age-related macular degeneration: twelve-month clinical outcomes. *Opthalmology* 2003; 110:2372-2383.
24. Motohiro K, Kazuhito Y, Noriaki K et al. Scavenger receptors for oxidized lipoprotein in age-related macular degeneration *Invest. Opthalmol. Vis. Sci.* 2007; 48: 1801-1807.
25. Amburad N, Harmon C, Ibrahimi A. Membrane transport of long chain fatty acids: evidence for a facilitated process. *J. lipid Res* 1998; 39: 2309-2318
26. Endemann G, Stanton L W, Madden S et al. CD36 is a receptor for oxidized low density lipoprotein. *J. Biol. Chem.* 1993; 268: 11811-11816.
27. FinnemannSC, Bonilha V L, Marmostein A D et al. Phagocytosis of rod outer segments by retinal pigment pigment epithelium. Proc Natl Acad Sci USA 1997; 94:12932-12937.
28. Jimenez B, Volpert O V, Crawford S E et al. Signals leading to apoptosis-dependent inhibition of neovascularization by thrombospondin1. *Nat med* 2000; 6: 41-48.
29. Murphy J E, Tedbury P R, Horner-Vannasinkam S et al. Biochemistry and cell biology of mammalian scavenger receptors. *Atherosclerosis* 2005; 182:1-15.
30. Pietsch A, weber C, Goretzski M et al. N-3 but not N-6 fatty acids reduce the expression of the combined adhesion and scavenger receptor CD36 in human monocytic cells. *Cell Biochem Funct.* 1995; 13: 211-216.
31. Dithmar S, Curcio C A, Le N A et al. Ultrastructural changes in Bruch's membrane of apolipoprotein E-deficient mice. *Investigative Opthalmology & visual Science* 2000; 41: 2035-2042.
32. Rudolf M, Ivandic B, Winkler J et al. Accumulation of lipid particles in Bruch's membrane of LDL receptor knockout mice as a model of age-related macular degeneration. *Opthalmoloe* 2004; 101:715-719.
33. Bowers C Y. Growth hormone-releasing peptides. *Cell Mol Life Sci.* 1998; 93: 1316-1329.
34. Howard A D, Feighner S D, Cully D F et al. A receptor in pituitary and hypothalamus that functions in growth hormone release. *Science* 1996:273: 974-977.
35. De Gennaro-Colonna V, Rossoni G, Bernareggi M et al. Cardiac ischemia and impairment of vascular endothelium function in hearts from growth hormone-deficient rats: protection by hexarelin. *Eur J. Pharmacol.* 1997; 334: 201-207.
36. Marleau S, Harb D, Bujold K et al. EP 80317, a ligand of the CD36 scavenger receptor, protects apolipoproteinE-deficient mice from developing atherosclerotic lesions. *FASEB J* 2005; 19:1869-1871.
37. Avallone R, Demers A, Rodrigue-Way A et al. A growth hormone-releasing peptide that binds scavenger receptor CD36 and ghrelin receptor upregulates ABC sterol transporters and cholesterol efflux in macrophages through PPARγ-dependent pathway. *Mol. Endocrinol.* 2006;
38. Demers A, Mc Nicoll N, Febbraio M et al. Identification of the growth hormone-releasing peptide binding site in CD36: a photoaffinity cross linking study. *BiochemJ* 2004; 382: 417-24.
39. Boeglin, D.; Lubell, W. D. Aza-Amino Acid Scanning of Secondary Structure Suited for Solid-Phase Peptide Synthesis with Fmoc Chemistry and Aza-Amino Acids with Heteroatomic Side chain. *J. Comb. Chem.* 2005; 7(6); 864-868.
40. Melendez, R. E.; Lubell, W. D. Aza-Amino Acid Scan for Rapid Identification of Secondary Structure Based on N-Boc-Azal-Dipeptides in Peptide Synthesis. *J. Am. Chem. Soc.* 2004; 126: 6759-6764.
41. Boeglin, D.; Xiang, Z.; Sorenson, N. B et al. Aza-scan of the Potent Melanocortin Receptor Agonist. *Chem. Biol. Drug Des.* 2006; 67: 275-283.
42. Rink, H. Solid-phase synthesis of protected peptide fragments using a trialkoxy-diphenyl-methylester resin. *Tetrahedron Lett.* 1987, 28, 3787-390.
43. Chang, C. D.; Meienhofer, J. Solid-phase peptide synthesis using mild base cleavage of N alpha-fluorenylmethyloxycarbonylamino acids, exemplified by a synthesis of dihydrosomatostatin. *Int. J. Pept. Protein Res.* 1978, 11, 246.
44. Gilbson, C.; Goodman S. L.; Hahn, D.; HOlzemann, G.; Kessler, H. Novel Solid-Phase Synthesis of Azapeptides and Azapeptoides via Fmoc-Strategy and Its Application in the Synthesis of RGD-Mimetics. *J. Org. Chem.*, 1999, 64, 7388-7394.
45. Bodart V, Febbraio M, Demers A. et al. CD36 mediates the cardiovascular action of growth hormone-releasing peptides in the heart. *Circ. Res* 2002; 90:844-849.
46. Mousseaux D, Le Gallic, Ryan J et al. Regulation of ERK1/2 activity by ghrelin activated growth hormone secretagogue receptor R1A involves a PLC/PKC epsilon pathway. *Brit J. Pharmacol.* 2006; 148: 350-365.
47. Elizabeth Rakoczy, P., Yu, M. J., Nusinowitz, S., Chang, B., and Heckenlively, J. R. 2006. Mouse models of age-related macular degeneration. *Exp Eye Res* 82:741-752.
48. Ershov A and Bazan N G. Induction of cyclooxygenase-2 gene expression in retinal pigment epithelium cells by photoreceptor rod outer segment phagocytosis and growth factors. *J Neurosci Res;* 1999 58:254-261.
49. Gante, J. Azapeptides. *Synthesis* 1989, 405.
50. (a) Quibell, M.; Turnell, W. G.; Johnson, T. Synthesis of azapeptides by the Fmoc/tert-butyl/polyamide technique. *J. Chem. Soc. Perkin Trans.* 1 1993, 2843-2849. (b) Liley, M.; Johnson, T. Solid-phase synthesis of azapeptides utilizing reversible amide bond protection to prevent hydantoin formation. *Tetrahedron Lett.* 2000, 41, 3983-3985.
51. Gray, C. J.; Quibell, M.; Bagget, N.; Hammerle, T. Incorporation of azaglutamine residues into peptides synthesized by the ultra-high load solid (gel)-phase technique. *Int. J. Pept. Protein Res.* 1992, 40, 351-362.
52. (a) Duthaler, R. O. Recent developments in the stereoselective synthesis of α-amino acids. *Tetrahedron* 1994, 50, 1539-1650. (b) Williams, R. M. in *Advances in Asymmetric Synthesis*; Hassner, A., Ed.; Jai Press Inc.: Greenwich, Conn., 1995; Vol. 1, pp 45-94. (c) Ojima, I. in *Advances in Asymmetric Synthesis*; Hassner, A., Ed.; Jai Press Inc.: Greenwich, Conn., 1995; Vol. 1, pp 95-146.
53. O'Donnell, M. J.; Zhou, Changyou, Z., Scott, W. L. Unnatural Peptide Synthesis. *J. Am. Chem. Soc.* 1996, 118, 6070-6071.
54. Bowers, C. Y.; Momany, F. A.; Reynolds, G. A.; Hong, A.; Newlander, K. On the in vitro and in vivo activity of a new synthetic hexapeptide that acts on the pituitary to specifically release growth hormone. *Endocrinology* 1984, 114, 1537-1545.
55. For a recent review on growth homone secretagogues, see: (a) Korbonits, M.; Goldstone, A. P.; Guerguiev, M.; Grossman, A. B. Ghrelin—a hormone with multiple functions.

*Front Neuroendocrinol.* 2004, 25, 27-68. (b) Fehrentz, J. A.; Martinez, J.; Boeglin, D.; Guerlavais, V.; Deghenghi, R. I. Growth hormone secretagogues: past, present and future. *Drugs* 2002, 5, 804-814.

56. Adams, J. H.; et al. A Reinvestigation of the Preparation, Properties, and Applications of Aminomethyl and 4-Methylbenzhydrylamine Polystyrene Resins. *J. Org. Chem.* 1998, 63, 3706-3716.

57. Torrini, I.; Zecchini, G. P.; Paradisi, M. P.; Mastropietro, G.; Lucente, G.; Gavuzzo, E.; Mazza, F. Topographically constrained aromatic α-aza-amino acids. Part 2. New aza-Tic-containing peptides: synthesis, conformation, and intramolecular NH—N interaction. *Tetrahedron* 1999, 55, 2077-2090.

58. Wieczerzak, E.; Drabik, P.; Lankiewicz, L.; Oldziej, S.; Grzonka, Z.; Abrahamson, M.; Grubb, A.; Bromme, D. Azapeptides Structurally Based upon Inhibitory Sites of Cystatins as Potent and Selective Inhibitors of Cysteine Proteases. *J. Med. Chem.* 2002, 45, 4202-4211.

59. (a) Arrowsmith, J. E.; Cook, M. J.; Hardstone, D. J. Reactions of anions of N-benzylidenebenzylamines and related compounds. A simple route to α-substituted benzylamines. *J. Chem. Soc., Perkin Trans,* 1 1979, 2364-2368. and references cited therein, (b) Asai, T.; Aoyama, T.; Shioiri, T. New methods and reagents in organic synthesis. 7. α-Alkylation of benzylamine under phase-transfer catalyzed conditions. *Synthesis* 1980, 811-812., (c) Bradamante, S.; Ferraccioli, R.; Pagani, G. A. The reaction of sodium 1,3-diphenyl-2-azapropenide with 1,2-epoxycyclohexane. *J. Chem. Soc., Perkin Tram.* 1, 3, 1987, 515-518.

60. O'Donnell, M. J.; et. al. Acidities of glycine Schiff bases and alkylation of their conjugate bases *J. Am. Chem. Soc.* 1998, 110, 8520-8525.

61. O'Donnell, M. J.; Delgado, F.; Hostettler, C.; Schwesinger, R. An efficient homogeneous catalytic enantioselective synthesis of α-amino acid derivatives. *Tetrahedron Lett.* 1998, 39, 8775-8778.

62. (a) Sturino, C. F.; Fallis, A. G. Samarium(II) Iodide Induced Radical Cyclizations of Halo- and Carbonylhydrazones. *J. Am. Chem. Soc.* 1994, 116, 7447-7448. (b) Mino, T.; Yamashita, M. Synthesis of 2-alkyl-2-methyl-3-butenonitriles via alkylation of 2-methyl-2-butenal N,N-dimethylhydrazone. *J. Org. Chem.* 1996, 61, 1159-1160. (c) Nakamura, E.; Kubota, K.; Sakata, G. Addition of Zincated Hydrazone to Vinyl Grignard Reagent. Ketone Synthesis by One-Pot Assembly of Four Components. *J. Am. Chem. Soc.* 1997, 119, 5457-5458.

63. Enders, D.; Wortmann, L.; Peters, R. Recovery of Carbonyl Compounds from N,N-Dialkylhydrazones. *Acc. Chem. Res.* 2000, 33, 157-169.

64. Hart, T. W.; Guillochon, D.; Perrier, G.; Sharp, B. W.; Toft, M. P.; Vacher, B.; Walsh, R. J. A. The synthesis of RP 66471. A potent potassium channel opener. *Tetrahedron Lett.* 1992, 33, 7211-7214.

65. Diez, E.; Lopez, A. M.; Pareja, C.; Martin, E.; Fernandez, R.; Lassaletta, J. M. Direct synthesis of dithioketals from N,N-dialkylhydrazones. *Tetrahedron Lett.* 1998, 39, 7955-7958.

66. Wilson, R. D.; Watson, S. P; Richards, S. A. Solid phase synthesis of 5-aminopyrazoles and derivatives. Part II. *Tetrahedron Lett.* 1998, 39, 2827-2830.

67. Falb, E.; Yechezkel, T.; Salitra, Y.; Gilon, C. In situ generation of Fmoc-amino acid chlorides using bis-(trichloromethyl)carbonate and its utilization for difficult couplings in solid-phase peptide synthesis. *J. Pept. Res.* 1999, 53, 507-517.

68. (a) Meienhofer, J.; Waki, M.; Heimer, E. D.; Lambros, T. J.; Makofske, R. C.; Chang, C. D. Solid phase synthesis without repetitive acidolysis. Preparation of leucyl-alanyl-glycyl-valine using 9-fluorenylmethyloxycarbonylamino acids. *Int. J. Pept. Protein Res.* 1979, 13, 35-42. (b) Lubell, W. D.; Blankenship, J. W.; Fridkin, G.; Kaul, R. Product class 11: Peptides. Science of Synthesis 2005, 21, 713-809.

69. Yang, J.; Song, H.; Xiao, X.; Wang, J.; Qin; Y. Biomimetic approach to perophoramidine and communesin via an intramolecular cyclopropanation reaction. *Org. Lett.* 2006, 8(10), 2187-2190.

70. Kaiser, E.; Colescott, R. L.; Bassinger, C. D.; Cook, P. I. Color test for detection of free terminal amino groups in the solid-phase synthesis of peptides. *Anal. Biochem.* 1970, 34, 595-598.

All literature, patents, published patent applications cited herein are hereby incorporated by reference.

One or more currently preferred embodiments have been described by way of example. It will be apparent to persons skilled in the art that a number of variations and modifications can be made without departing from the scope of the invention as defined in the claims.

The invention claimed is:

1. An azapeptide compound of Formula: Ala-DTrp-Ala-AzaPhe-DPhe-Lys-NH$_2$.

2. The azapeptide compound of claim 1, admixed with one or more of a pharmaceutically acceptable carrier, diluent or excipient.

* * * * *